(12) United States Patent
Lee et al.

(10) Patent No.: US 6,384,061 B1
(45) Date of Patent: May 7, 2002

(54) HYDANTOIN COMPOUNDS AND METHODS RELATED THERETO

(75) Inventors: Jin Ho Lee; Jong Sung Koh; Jong Hyun Kim; Hyun Il Lee; Won Hee Jung; Seong Gu Ro; You Seong Shin; Sang Woong Kim; Ki Won Park; Tae Hwan Kwak; Kyung Duk Moon; Hyun Ho Chung, all of Taejon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/463,551

(22) PCT Filed: Jul. 24, 1998

(86) PCT No.: PCT/KR98/00225

§ 371 Date: Mar. 30, 2000

§ 102(e) Date: Mar. 30, 2000

(87) PCT Pub. No.: WO99/05117

PCT Pub. Date: Feb. 4, 1999

(51) Int. Cl.[7] ............... A61K 31/44; A61K 31/415; C07D 401/00; C07D 403/06; C07D 233/40
(52) U.S. Cl. ............... 514/341; 514/389; 546/210; 546/274.4; 548/314.4; 548/321.1
(58) Field of Search ............... 548/314.4, 321.1; 546/210, 274.4; 514/341, 389

(56) References Cited

U.S. PATENT DOCUMENTS

| | | | | |
|---|---|---|---|---|
| 3,122,583 A | * | 2/1964 | Galloway | 548/314.4 X |
| 3,136,775 A | * | 6/1964 | Hause | 548/314.4 |
| 4,705,864 A | * | 11/1987 | Cesa et al. | 548/314.4 X |
| 5,177,097 A | * | 1/1993 | Poss | 514/386 |
| 5,308,853 A | * | 5/1994 | Hodges et al. | 514/336 |
| 5,861,517 A | * | 1/1999 | Elokdah et al. | 548/321.1 |
| 5,939,556 A | * | 8/1999 | Zoller et al. | 548/320.1 |

FOREIGN PATENT DOCUMENTS

| | | | | |
|---|---|---|---|---|
| DE | 4009506 | * | 9/1991 | |
| DE | 4126277 | * | 2/1993 | |
| JP | 4-164071 | * | 6/1992 | 548/314.4 |
| JP | 4-198173 | * | 7/1992 | 548/314.4 |

* cited by examiner

Primary Examiner—Floyd D. Higel
Assistant Examiner—Ebenezer Sackey
(74) Attorney, Agent, or Firm—Peter F. Corless; Christine C. O'Day; Edwards & Angell, LLP

(57) ABSTRACT

The present invention relates to novel hydantoin compounds represented by formula (I) which shows an inhibitory activity against farnesyl transferase, and thus can be used as an anti-cancer agent, or pharmaceutically acceptable salts thereof, in which $R_1$, $R_2$, $R_3$ and $R_4$ are as defined in the present application. The present invention also relates to a process for preparation of the compound of formula (I), and to an anti-cancer composition comprising the compound of formula (I) as an active ingredient.

5 Claims, No Drawings

HYDANTOIN COMPOUNDS AND METHODS RELATED THERETO

This appln is a 371 of PCT/KR98/00225 filed on Jul. 24, 1998.

TECHNICAL FIELD

The present invention relates to a novel hydantoin derivative represented by the following formula (I) which shows an inhibitory activity against farnesyl transferase, and thus can be used as an effective therapeutic agent against antiproliferative diseases such as resfenosis, Rheumatitis arthrititis and particularly cancer:

[Formula I]

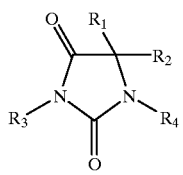

or pharmaceutically acceptable salts thereof, in which $R_1$, $R_2$, $R_3$ and $R_4$ are defined as described below.

The present invention also relates to a process for preparation of the compound of formula (I) and to an anticancer composition comprising the compound of formula (I) as an active ingredient.

BACKGROUND ART

Mammalian Ras proteins act as molecular switches in the signalling events associated with cell growth and differentiation. The ras proto-oncogene family consists of three members, N-, K-, and H-ras, which code for highly homologous four types of proteins; i.e. H-, N-ras proteins of 189 residues and two isomorphic K-ras-4B and K-ras-4A proteins of 188 and 189 residues, respectively. The chemical basis for the switch mechanism involves cycling of the protein between the inactive (off) guanosine diphosphate (GDP) bound state and the active (on) guanosine triphosphate (GTP) bound state (Bourne. H. R.; Sanders, D. A.; McCormick, F.; Nature, 1991, 349,117). Biochemical and structural studies have shown that point mutations of the residues 12, 13, and 61, positioned in the neighborhood of phosphoryl group of GTP, resulting in the decrease of guanosine triphosphatase activity are associated with many human cancers, particularly, pancreatic cancer, urinary bladder carcinoma, colon cancer, etc. (Bos, J. L., Cancel Res., 1989, 49, 4682).

Ras protein is synthesized as a cytosolic precursor that is ultimately localized to the cytoplasmic face of the plasma membrane after a series of posttranslational modification (Gibbs, J. B., Cell 1991, 65, 1). These series of biochemical modifications, by changing the electrical charge state or spacial structure to increase the hydrophobicity allow Ras protein to attach to cell membrane more easily. The first and obligatory step in the series is the addition of a farnesyl moiety to the cysteine residue of the C-terminal CAAX motif (C, cysteine, A, usually aliphatic residue; X, any other amino acid) in a reaction catalyzed by farnesyl protein transferase (FTase). This modifications is essential for Ras function, as demonstrated by the inability of Ras mutants lacking the C-terminal cysteine to be farnesylated, to localize to the plasma, and to transform mammalian cells in culture (Hancock, J. F., Magee, A. I., Child, J. E., Marshall, C. J., Cell 1989, 57, 1167). The subsequent posttranslational modifications, cleavage of the AAX residues, carboxyl methylation of the farnesylated cysteine, and palmitoylation of the cysteines located upstream of the CAAX motif in H-and N-ras proteins are not obligatory for Ras membrane association or cellular transforming activity. Interestingly, K-ras-4B, different from H- and N-ras, has a multiple lysine rich region named polybasic domain, instead of having cysteine required for palmitoylation, thereby facilitating the farnesylated ras protein to bind to anionic lipid layer of cell membrane. The inhibitors of FTase that catalyzes the obligatory modification have therefore been suggested as anticancer agents for tumors in which Ras oncogene contributes to transformation (Buses, J. E. et al., Chemistry & Biology, 1995, 2 787). A number of FTase inhibitors have recently identified demonstrated potent and specific ability to block Ras farnesylation. signalling and transformation in transformed cells and tumor cell lines both in vitro and in animal models (Koh, N. E. et al., Proc. Natl. Acad. Sci. USA, 1994, 91, 914; Kohl, N. E. et al., Nature Medicine. 1995, 1 792). However, most of the inhibitors are related to CAAX motif as Ras substrate mimic and peptidie in nature or contain a sulfhydryl group (U.S. Pat. No. 5.141,851; Kohl, N. E. et al., Science, 1993, 260, 1934; PCT/US95/12224, Graham et al., Sebti, S. M. et al., J. Biol. Chem., 1995, 270, 26802; James, G. L. et al., Science, 1993 260, 1937; Bishop, W. R. et al., J. Biol. Chem., 1995, 270, 3061 1) Recently, a new type of peptidomimetic inhibitor imitating catalytic step of FTase has been reported (Poulter, C. D. et al., J. Am. Chem. Soc., 1996, 118,8761). The chemical basis of the inhibitor design relates to the reaction mechanism. That is, transferring prenyl group by the enzyme is electrophilic displacement and the reaction requires (+) charge in a transition state.

These inhibitors previously described however possess limited activity and selectivity for inhibition of the oncogenic function of Ras proteins, particularly K-ras-4B, which is found to be most common in human cancer. Therefore, new inhibitor having the ability of effectively inhibiting K-ras activity is required.

DISCLOSURE OF INVENTION

The present inventors have performed studies for developing a compound having the structure characteristics imitating transition state of catalytic reaction of farnesyl transferase and as a result, found that hydantoin derivatives according to the present invention can inhibit farnesyl transferase activity by imitating transition state of catalytic reaction of farnesyl transferase.

Therefore, the object of the present invention is to provide a hydantoin derivative of formula (I) which inhibits the activity of farnesyl transferase, process for preparation thereof, and anti-cancer composition comprising the compound of formula (I) as an active component.

BEST MODE FOR CARRYING OUT THE INVENTION

It is the first object of the present invention to provide a hydantoin derivative represented by the following formula (I) and pharmaceutically acceptable salt thereof which inhibit the activity of farnesyl transferase

[Formula I]

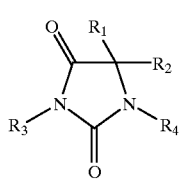

in which

R₁ and R₂ independently of one another represent hydrogen; lower alkyl; monocyclic or bicyclic alkyl group which can be substituted by lower alkyl or halogen; heterocyclic group containing hetero atoms selected from a group consisting of nitrogen and sulfur as ring member; or a radical having the following formula:

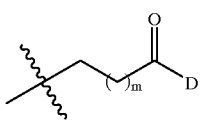

(wherein D represents alkoxy; hydroxy; amino acid residue; morpholine; thiomorpholine; piperazine, alkoxyalkylamine or alkyloxyalkylamine each of which is substituted or unsubstituted by lower alkyl, and m is selected from 0 to 2), R₃ represents amino acid residue, or a radical having the following formula,

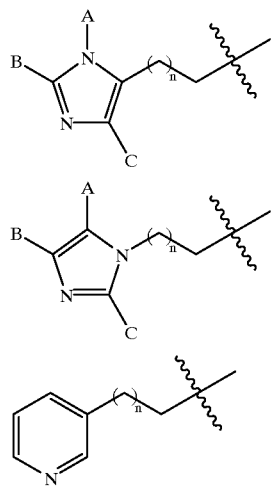

wherein

A represents hydrogen; lower alkyl; aryl group which is substituted by substituents selected from a group consisting of halogen, cyano (CN) nitro(NO₂), carboxy (COOH), amide, thioamide, SR and lower alkyl; heterocyclic group which is substituted by substituents selected from a group consisting, of halogen, cyano, nitro, COOR, amide, thioamide, SR and lower alkyl and which comprises nitrogen or sulfur atom as ring member; lower alkyl substituted by the substituted aryl or heterocyclic group as mentioned above; or a radical having the following formula:

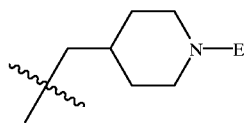

(in the definition for the substituent A, R represents hydrogen or lower alkyl, and E represents hydrogen or —F—G wherein F represents CH₂, C=O, SO₂, and G represents hydrogen; lower alkyl substituted or unsubstituted by phenyl or biphenyl: lower alkoxy; phenyl benzyl; benzyloxy; amine substituted or unsubstituted by lower alkyl, phenyl, benzyl, cycloalkyl or phenoxy alkyl), B and C independently of one another represent hydrogen, halogen or lower alkyl.

n denotes an integer of 0 to 4,

R₄ represents hydrogen; aromatic group substituted or unsubstituted by lower alkyl or halogen; bicyclic aromatic group; heteroaromatic group containing hetero atoms selected from a group consisting of nitrogen and sulfur as ring member; or a radical having the following formula:

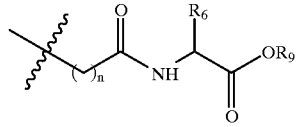

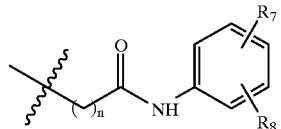

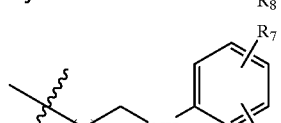

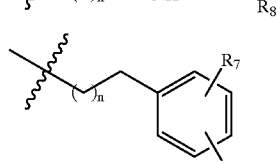

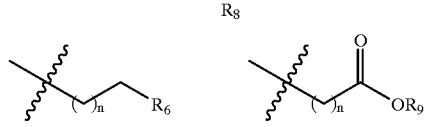

-continued

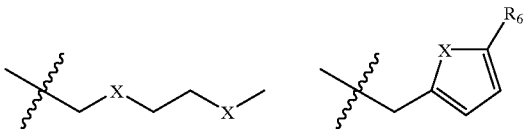

wherein

R₅ represents aryl group substituted by lower alkoxy; or heterocyclic group containing hetero atoms selected from a group consisting of nitrogen, oxygen and sulfur as ring member, R₆ represents hydrogen; lower alkyl; lower alkyl which is substituted by substituents selected from a group consisting of halogen, cyano, hydroxy, COOR, amide, thioamide, SR and SO₂R; lower alkyl substituted by an aryl group which is substituted by substituents selected from a group consisting of halogen, cyano, COOR, amide, thioamide, SR, SO₂R and lower alkyl; heterocyclic group containing hetero atoms selected from a group consisting of nitrogen and sulfur as ring member; heterocyclic group which is substituted by substituents selected from a group consisting of halogen, cyano, COOR, amide, thioamide, SR, SO₂R and lower alkyl and which contains hetero atoms selected from a group consisting of nitrogen and sulfur as ring member, wherein R represents lower alkyl, R₇ and R₈ independently of one another represent hydrogen, halogen, halogenoalkyl, cyano, amide, thioamide, alkoxy or phenoxy, or represent a radical having the following formula,

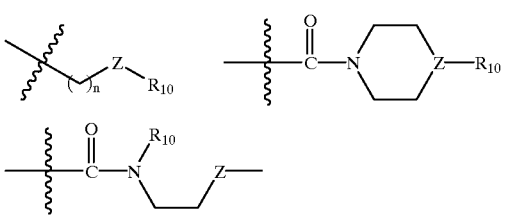

wherein

Z represents CH₂, CO, O, S, SO₂, NR₉, NHSO₂ or NHCOO,

R₁₀ represents hydrogen, lower alkyl, halogenoalkyl, alkoxy, hydroxy, benzyloxycarbonyl or benzyl, R₉ represents hydrogen or lower alkyl, or lower alkyl substituted by aromatic group, X represents CH₂, CO, O, S or SO₂, and n denotes an integer of 0 to 4.

In the definitions for the substituents of the compound of formula (I), the term "lower alkyl" means a straight or branched alkyl having 1 to 4 carbon atoms which includes methyl, ethyl, isopropyl, isobutyl and t-butyl; the term "heterocyclic group containing hetero atoms selected from a group consisting of nitrogen and sulfur as ring member" means mono- or bicyclic aliphatic or aromatic group containing one or two nitrogen or sulfur in the ring as ring member.

The abbreviations for amino acids used in the present specification are consistent with IUPAC-IUB Commission on biochemical nomenclature of amino acid and peptide [*Eur. J. Biochem.*, 1984, 158, 9–31].

Also, the compound of formula (I) according to the present invention can form a pharmaceutically acceptable salt. Such salt includes non-toxic acid addition salt containing pharmaceutically acceptable anion, for example a salt with inorganic acids such as hydrochloric acid, sulfuric acid, nitric acid, phosphoric acid, hydrobromic acid, hydriodic acid, etc., a salt with organic carboxylic acids such as tartaric acid, formic acid, citric acid, acetic acid, trichloroacetic acid, trofluoroacetic acid, gluconic acid, benzoic acid, lactic acid, fumaric acid, maleic acid, etc., or a salt with sulfonic acids such as methanesulfonic acid, benzenesulfonic acid, p-toluenesulfonic acid, naphthalenesulfonic acid, etc.; and metal addition salt for example a salt with alkali metal or alkaline earth metal such as lithium salt. Further, the present invention includes a solvate of the compound of formula (I) such as alcoholate, and hydrate thereof.

Since the compound of formula (I) according to the present invention may have asymmetric carbon atoms depending on the substituents, they can be present in the form of racemate, diastereomer mixture or the individual diastereomers. Thus, the present invention also includes all of these stereoisomers and their mixtures.

Among the compound of formula (I) according to the present invention, the preferred compounds include those wherein R₁ represents hydrogen; monocyclic or bicyclic aryl group which can be substituted by lower alkyl or halogen; or a radical having the following formula:

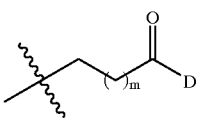

(wherein D represents alkoxy; hydroxy; amino acid residue; morpholine; thiomorpholine; piperazine or alkoxyalkylamine each of which is substituted or unsubstituted by lower alkyl, and m is selected from 0 to 1), R₂ represents hydrogen; lower alkyl; or a radical having the following formula:

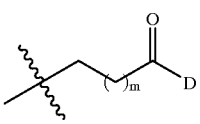

wherein D represents alkoxy; hydroxy; amino acid residue; morpholine; thiomorpholine; piperazine or alkoxyalkylamine each of which is substituted or unsubstituted by lower alkyl, and m is selected from 0 to 1), R₃ represents a radical having the following formula,

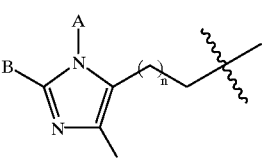

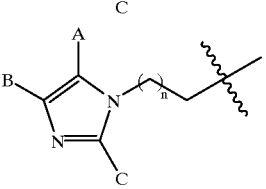

wherein

A represents hydrogen; aryl group which is substituted by substituents selected from a group consisting of halogen, cyano(CN), nitro(NO$_2$), carboxy(COOH), amide, thioamide, SR and lower alkyl; or a radical having the following formula:

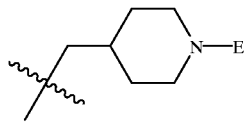

(in the definition for the substituent A, R represents hydrogen or lower alkyl, and E represents hydrogen or —F—G wherein F represents C=O, and G represents benzyloxy, lower alkoxy, or lower alkyl substituted or unsubstituted by phenyl), B and C independently of one another represent hydrogen, n denotes an integer of 1 to 3, R$_4$ represents hydrogen; aromatic group substituted or unsubstituted by halogen; bicyclic aromatic group; heteroaromatic group containing hetero atoms selected from a group consisting of nitrogen and sulfur as ring member; or a radical having the following formula:

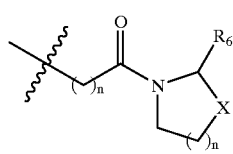

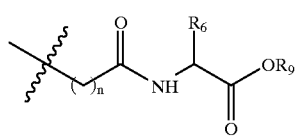

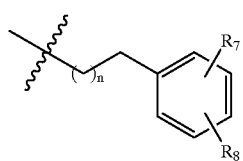

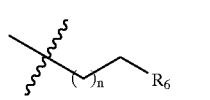 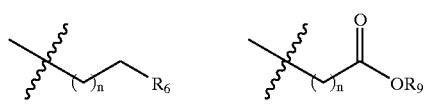

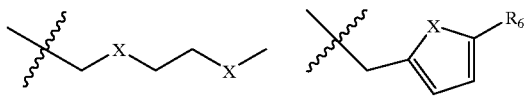

wherein

R$_5$ represents aryl group substituted by lower alkoxy; or heterocyclic group containing hetero atoms selected from a group consisting of nitrogen, oxygen and sulfur as ring, member, R$_6$ represents hydrogen; lower alkyl; lower alkyl which is substituted by substituents selected from a group consisting of halogen, cyano, hydroxy, COOR, amide, thioamide, SR and SO$_2$R; lower alkyl substituted by an aryl group which is substituted by substituents selected from a group consisting of halogen, cyano, COOR, amide, thioamide, SR, SO$_2$R and lower alkyl; or heterocyclic group containing hetero atoms selected from a group consisting, of nitrogen and sulfur as ring member; heterocyclic group which is substituted by substituents selected from a group consisting of halogen, cyano, COOR, amide, thioamide, SR, SO$_2$R and lower alkyl and which contains hetero atoms selected from a group consisting of nitrogen and sulfur as ring member, wherein R represents lower alkyl, R$_7$ and R$_8$ independently of one another represent hydrogen, halogen, halogenoalkyl, cyano or phenoxy, or represent a radical having the following formula,

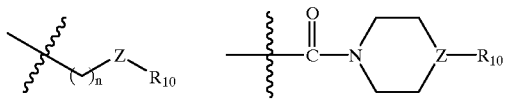

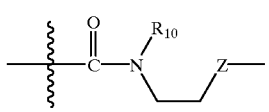

wherein

Z represents O, S, SO$_2$, NR$_9$, NHSO$_2$ or NHCOO,

R$_{10}$ represents hydrogen, lower alkyl, halogenoalkyl, alkoxy, hydroxy or benzyloxycarbonyl, R$_9$ represents or lower alkyl, X represents O, S or SO$_2$, and n denotes an integer of 1 or 3.

Typical examples of the compound of formula (I) according to the present invention are presented in the following Tables 1a to 1v.

TABLE 1A

| COM. NO. | Formula | Nomenclature |
|---|---|---|
| 1 | | 2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid methyl ester |
| 2 | | 2-(2-{3-[3-(1H-imidazol-4-yl)-propyl]-5-methyl-5-naphthalen-1-yl-2,4-dioxo-imidazolin-1-yl}-acetylamino)-4-methylsulfanyl-butyric acid |
| 3 | | 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid methyl ester |
| 4 | | 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid |

TABLE 1B

| COM. NO. | Formula | Nomenclature |
|---|---|---|
| 5 | | 2-{2-[3-(3H-imidazol-4-yl-methyl)-5-methyl-5-naphthalen-1-yl-2,4-dioxo-imidazolidin-1-yl]-acetylamino}-4-methyl-sulfanyl-butyric acid methyl ester |

TABLE 1B-continued

| COM. NO. | Formula | Nomenclature |
|---|---|---|
| 6 | | 2-{2-[3-(3H-imidazol-4-yl-methyl)-5-methyl-5-naphthalen-1-yl-2,4-dioxo-imidazolidin-1-yl]-acetylamino-4-methyl-sulfanyl-butyric acid |
| 7 | | 2-(2-{3-[3-(4-cyano-benzyl)-imidazol-4-yl)-methyl]-5-methyl-5-naphthalen-1-yl-2,4-dioxo-imidazolidin-1-yl}-acetylamino)-4-methylsulfanyl-butyric acid methyl ester |
| 8 | | 2-(2-{3-[3-(4-cyano-benzyl)-imidazol-4-yl)-methyl]-5-methyl-5-naphthalen-1-yl-2,4-dioxo-imidazolidin-1-yl}-acetylamino)-4-methylsulfanyl-butyric acid |

TABLE 1C

| COM. NO. | Formula | Nomenclature |
|---|---|---|
| 9 | | 2-(2-{3-[3-(3H-imidazol-4-yl)-propyl]-5-methyl-5-naphthalen-1-yl-2,4-dioxo-imidazolidin-1-yl}-acetylamino)-3-thiophen-2-yl-propionic acid |

TABLE 1C-continued

| COM. NO. | Formula | Nomenclature |
|---|---|---|
| 10 | | 3-[3-(3H-imidazol-4-yl)-propyl]-5-methyl-5-napthahlen-1-yl-1-(2-oxo-2-thiazolidin-3-yl-ethyl)-imidazolidin-2,4-dione |
| 11 | | 1-[2-(1,1-dioxo-thiazolidin-3-yl)-3-(3H-imidazol-4-yl)-propyl]-5-methyl-5-naphthalen-1-yl-imidazolidin-2,4-dione |
| 12 | | 3-[3-(3H-imidazol-4-yl)-propyl]-5-methyl-1-{2-[2-(2-methyl-sulfanyl-ethyl)-thiazolidin-3-yl]-2-oxo-ethyl}-5-naphthalen-1-yl-imidazolidin-2,4-dione |

TABLE 1D

| COM. NO. | Formula | Nomenclature |
|---|---|---|
| 13 | | 2-(2-{3-[3-(3H-imidazol-4-yl)-propyl]-5-methyl-5-naphthalen-1-yl-2,4-dioxo-imidazolidin-1-yl}-acetylamino)-4-methylsulfonyl-butyric acid |
| 14 | | 2-{2-[3-(3-imidazol-1-yl-propyl)-5-methyl-5-naphthalen-1-yl-2,4-dioxo-imidazolidin-1-yl]-acetylamino}-4-methylsulfanyl-butyric acid |

TABLE 1D-continued

| COM. NO. | Formula | Nomenclature |
|---|---|---|
| 15 | | 2-{2-[3-(2-imidazol-1-yl-ethyl)-5-methyl-5-naphthalen-1-yl-2,4-dioxo-imidazolidin-1-yl]-acetylamino}-4-methylsulfanyl-butyric acid |
| 16 | | 1-benzyl-3-(3-imidazol-1-yl-propyl)-5-methyl-5-naphthalen-1-yl-imidazolidin-2,4-dione |

TABLE 1E

| COM. NO. | Formula | Nomenclature |
|---|---|---|
| 17 | | 1-(pentafluoro-benzyl)-3-(3-imidazol-1-yl-propyl)-5-methyl-5-naphthalen-1-yl-imidazolidin-2,4-dione |
| 18 | | 1-(3-pyridylmethyl)-3-(3-imidazol-1-yl-propyl)-5-methyl-5-naphthalen-1-yl-imidazolidin-2,4-dione |

TABLE 1E-continued

| COM. NO. | Formula | Nomenclature |
|---|---|---|
| 19 | | 1-(3-chloro-benzyl)-3-(3-imidazol-1-yl-propyl)-5-methyl-5-naphthalen-1-yl-imidazolidin-2,4-dione |
| 20 | | 1-(3-bromo-benzyl)-3-(3-imidazol-1-yl-propyl)-5-methyl-5-naphthalen-1-yl-imidazolidin-2,4-dione |

TABLE 1F

| COM. NO. | Formula | Nomenclature |
|---|---|---|
| 21 | | 1-(4-bromo-benzyl)-3-(3-imidazol-1-yl-propyl)-5-methyl-5-naphthalen-1-yl-imidazolidin-2,4-dione |
| 22 | | 1-(3-trifluoromethyl-benzyl)-3-(3-imidazol-1-yl-propyl)-5-methyl-5-naphthalen-1-yl-imidazolidin-2,4-dione |
| 23 | | 1-(3-trifluoromethoxy-benzyl)-3-(3-imidazol-1-yl-propyl)-5-methyl-5-naphthalen-1-yl-imidazolidin-2,4-dione |

TABLE 1F-continued

| COM. NO. | Formula | Nomenclature |
|---|---|---|
| 24 | | 3-(3-imidazol-1-yl-propyl)-5-methyl-5-naphthalen-1-yl-1-(4-phenoxy-benzyl)-imidazolidin-2,4-dione |

TABLE 1G

| COM. NO. | Formula | Nomenclature |
|---|---|---|
| 25 | | 3-(3-imidazol-1-yl-propyl)-5-methyl-5-naphthalen-1-yl-1-(3-phenoxy-benzyl)-imidazolidin-2,4-dione |
| 26 | | 3-(3-imidazol-1-yl-propyl)-1-(4-methylsulfanyl-benzyl)-5-methyl-5-naphthalen-1-yl-imidazolidin-2,4-dione |
| 27 | | 3-(3-imidazol-1-yl-propyl)-5-methyl-1-(4-methylsulfanyl-methyl-benzyl)-5-naphthalen-1-yl-imidazolidin-2,4-dione |

TABLE 1G-continued

| COM. NO. | Formula | Nomenclature |
|---|---|---|
| 28 | | 3-(3-imidazol-1-yl-propyl)-5-methyl-1-(4-methylsulfonyl-benzyl)-5-naphthalen-1-yl-imidazolidin-2,4-dione |

TABLE 1H

| COM. NO. | Formula | Nomenclature |
|---|---|---|
| 29 | | 5-[3-(3-imidazol-1-yl-propyl)-5-methyl-5-naphthalen-1-yl-2,4-dioxo-imidazolidin-1-ylmethyl]-2-methylsulfanyl-benzonitrile |
| 30 | | 5-[3-(3-imidazol-1-yl-propyl)-5-methyl-5-naphthalen-1-yl-2,4-dioxo-imidazolidin-1-ylmethyl]-2-methylsulfonyl-benzonitrile |
| 31 | | 2-[3-(3-imidazol-1-yl-propyl)-5-methyl-5-naphthalen-1-yl-2,4-dioxo-imidazolidin-1-ylmethyl]-benzonitrile |

TABLE 1H-continued

| COM. NO. | Formula | Nomenclature |
|---|---|---|
| 32 | | 3-[3-(3-imidazol-1-yl-propyl)-5-methyl-5-naphthalen-1-yl-2,4-dioxo-imidazolidin-1-ylmethyl]-benzonitrile |

TABLE 1I

| COM. NO. | Formula | Nomenclature |
|---|---|---|
| 33 | | 4-[3-(3-imidazol-1-yl-propyl)-5-methyl-5-naphthalen-1-yl-2,4-dioxo-imidazolidin-1-ylmethyl]-benzonitrile |
| 34 | | 1-(4-aminomethyl-benzyl)-3-(3-imidazol-1-yl-propyl)-5-methyl-5-naphthalen-1-yl-imidazolidin-2,4-dione |
| 35 | | N-{2-[3-(3-imidazol-1-yl-propyl)-5-methyl-5-naphthalen-1-yl-2,4-dioxo-imidazolidin-1-ylmethyl]-benzyl}-methane-sulfonamide |

TABLE 1I-continued

| COM. NO. | Formula | Nomenclature |
| --- | --- | --- |
| 36 | | N-{3-[3-(3-imidazol-1-yl-propyl)-5-methyl-5-naphthalen-1-yl-2,4-dioxo-imidazolidin-1-ylmethyl]-benzyl}-methane-sulfonamide |

TABLE 1J

| COM. NO. | Formula | Nomenclature |
| --- | --- | --- |
| 37 | | N-{4-[3-(3-imidazol-1-yl-propyl)-5-methyl-naphthalen-1-yl-2,4-dioxo-imidazolidin-1-ylmethyl]-benzyl}-methane-sulfonamide |
| 38 | | 4-[3-(3-imidazol-1-yl-propyl)-5-methyl-5-naphthalen-1-yl-2,4-dioxo-imidazolidin-1-ylmethyl]-benzoic acid methyl ester |
| 39 | | 4-[3-(3-imidazol-1-yl-propyl)-5-methyl-5-naphthalen-1-yl-2,4-dioxo-imidazolidin-1-ylmethyl]-benzoic acid |

TABLE 1J-continued

| COM. NO. | Formula | Nomenclature |
|---|---|---|
| 40 | | 3-(3-imidazol-1-yl-propyl)-1-[3-(morpholine-4-carbonyl)-benzyl]-5-methyl-5-naphthalen-1-yl-imidazolidin-2,4-dione |

TABLE 1K

| COM. NO. | Formula | Nomenclature |
|---|---|---|
| 41 | | 4-[3-(3-imidazol-1-yl-propyl)-5-methyl-5-naphthalen-1-yl-2,4-dioxo-imidazolidin-1-ylmethyl]-N-(2-methoxy-ethyl)-benzamide |
| 42 | | 4-[3-(3-imidazol-1-yl-propyl)-5-methyl-5-naphthalen-1-yl-2,4-dioxo-imidazolidin-1-ylmethyl]-N-(2-methoxy-ethyl)-N-methyl-benzamide |
| 43 | | 4-{4-[3-(3-imidazol-1-yl-propyl)-5-methyl-5-naphthalen-1-yl-2,4-dioxo-imidazolidin-1-ylmethyl]-benzoyl}-piperazine-1-carboxylic acid benzyl ester |

TABLE 1K-continued

| COM. NO. | Formula | Nomenclature |
|---|---|---|
| 44 | | 3-(3-imidazol-1-yl-propyl)-1-[3-(thiomorpholine-4-carbonyl)-benzyl]-5-methyl-5-naphthalen-1-yl-imidazolidin-2,4-dione |

TABLE IL

| COM. NO. | Formula | Nomenclature |
|---|---|---|
| 45 | | 4-{5-[3-(4-methyl-4-naphthalen-1-yl-2,5-dioxo-imidazolidin-1-yl)-propyl]-imidazol-1-ylmethyl}-benzonitrile |
| 46 | | 4-{5-[3-(3-methyl-4-methyl-4-naphthalen-1-yl-2,5-dioxo-imidazolidin-1-yl)-propyl]-imidazol-1-ylmethyl}-benzonitrile |
| 47 | | 4-{5-[3-(3-ethyl-4-methyl-4-naphthalen-1-yl-2,5-dioxo-imidazolidin-1-yl)-propyl]-imidazol-1-ylmethyl}-benzonitrile |

TABLE IL-continued

| COM. NO. | Formula | Nomenclature |
|---|---|---|
| 48 | | 4-{5-[3-(3-propyl-4-methyl-4-naphthalen-1-yl-2,5-dioxo-imidazolidin-1-yl)-propyl]-imidazol-1-ylmethyl}-benzonitrile |

TABLE 1M

| COM. NO. | Formula | Nomenclature |
|---|---|---|
| 49 | | 4-{5-[3-(3-butyl-4-methyl-4-naphthalen-1-yl-2,5-dioxo-imidazolidin-1-yl)-propyl]-imidazol-1-ylmethyl}-benzonitrile |
| 50 | | 4-(5-{3-[3-(2-methoxy-ethoxy-methyl)-4-methyl-4-naphthalen-1-yl-2,5-dioxo-imidazolidin-1-yl]-propyl}-imidazol-1-ylmethyl)-benzonitrile |
| 51 | | (3-{3-[3-(4-cyanobenzyl)-3H-imidazol-4-yl]-propyl}-5-methyl-5-naphthalen-1-yl-2,4-dioxo-imidazolidin-1-yl)-acetic acid ethyl ester |

TABLE 1M-continued

| COM. NO. | Formula | Nomenclature |
|---|---|---|
| 52 | | (3-{3-[3-(4-cyanobenzyl)-3H-imidazol-4-yl]-propyl}-5-methyl-5-naphthalen-1-yl-2,4-dioxo-imidazolidin-1-yl)-acetic acid |

TABLE 1N

| COM. NO. | Formula | Nomenclature |
|---|---|---|
| 53 | | 4-(5-{3-[3-benzyl-4-methyl-4-naphthalen-1-yl-2,5-dioxo-imidazolidin-1-yl]-propyl}-imidazol-1-ylmethyl)-benzonitrile |
| 54 | | 4-(5-{3-[3-(3-cyano-benzyl)-4-methyl-4-naphthalen-1-yl-2,5-dioxo-imidazolidin-1-yl]-propyl}-imidazol-1-ylmethyl)-benzonitrile |

TABLE 1N-continued

| COM. NO. | Formula | Nomenclature |
|---|---|---|
| 55 | | 4-{5-[3-(3-furan-2-ylmethyl-4-methyl-4-naphthalen-1-yl-2,5-dioxo-imidazolidin-1-yl)-propyl]-imidazol-1-ylmethyl}-benzonitrile |

TABLE 1O

| COM. NO. | Formula | Nomenclature |
|---|---|---|
| 56 | | 4-(5-{3-[3-(furan-2-carbonyl)-4-methyl-4-naphthalen-1-yl-2,5-dioxo-imidazolidin-1-yl]-propyl}-imidazol-1-ylmethyl)-benzonitrile |
| 57 | | 2-[2-(3-{3-[3-(4-cyano-benzyl)-3H-imidazol-4-yl]-propyl}-5-methyl-5-naphthalen-1-yl-2,4-dioxo-imidazolidin-1-yl)-acetylamino]-4-methylsulfanyl-butyric acid methyl ester |
| 58 | | 2-[2-(3-{3-[3-(4-cyano-benzyl)-3H-imidazol-4-yl]-propyl}-5-methyl-5-naphthalen-1-yl-2,4-dioxo-imidazolidin-1-yl)-acetylamino]-4-methylsulfanyl-butyric acid |

TABLE 1O-continued

| COM. NO. | Formula | Nomenclature |
|---|---|---|
| 59 | | 4-[5-(4-methyl-4-naphthalen-1-yl-2,5-dioxo-imidazolidin-1-ylmethyl)-imidazol-1-ylmethyl]-benzonitrile |

TABLE 1P

| COM. NO. | Formula | Nomenclature |
|---|---|---|
| 60 | | 4-[5-(3-methyl-4-methyl-4-naphthalen-1-yl-2,5-dioxo-imidazolidin-1-ylmethyl)-imidazol-1-ylmethyl]-benzonitrile |
| 61 | | 4-[5-(3-ethyl-4-methyl-4-napthalen-1-yl-2,5-dioxo-imidazolidin-ylmethyl)-imidazol-1-ylmethyl]-bentonitrile |

TABLE 1P-continued

| COM. NO. | Formula | Nomenclature |
|---|---|---|
| 62 | | {3-[3-(4-cyano-benzyl)-3H-imidazol-4-ylmethyl]-5-methyl-5-naphthalen-1-yl-2,4-dioxo-imidazolidin-1-yl}-acetic acid ethyl ester |
| 63 | | 4-{5-[3-(3-cyanobenzyl)-4-methyl-4-naphthalen-1-yl-2,5-dioxo-imidazolidin-1-ylmethyl]-imidazol-1-ylmethyl}-benzonitrile |

TABLE 1Q

| COM. NO. | Formula | Nomenclature |
|---|---|---|
| 64 | | 3-(3-imidazol-1-yl-propyl)-1-(4-methoxy-benzyl)-5-methyl-5-naphthalen-1-yl-imidazolidin-2,4-dione |
| 65 | | 3-(3-imidazol-1-yl-propyl)-5-methyl-1-(morpholine-4-carbonyl)-5-naphthalen-1-yl-imidazolidin-2,4-dione |

TABLE 1Q-continued

| COM. NO. | Formula | Nomenclature |
|---|---|---|
| 66 | | 3-(3-imidazol-1-yl-propyl)-5-methyl-5-naphthalen-1-yl-2,4-dioxo-imidazolidine-1-carboxylic acid (3-cyano-phenyl)-amide |
| 67 | | N-(4-cyano-tetrahydropyran-4-yl)-2-[3-(3-imidazol-1-yl-propyl)-5-methyl-5-naphthalen-1-yl-2,4-dioxo-imidazolidin-1-yl]-acetamide |

TABLE 1R

| COM. NO. | Formula | Nomenclature |
|---|---|---|
| 68 | | 3-{3-[3-(4-bromo-benzyl)-3H-imidazol-4-yl]-propyl}-5-methyl-5-naphthalen-1-yl-imidazolidin-2,4-dione |
| 69 | | 3-{3-[3-(4-bromo-benzyl)-3H-imidazol-4-yl]-propyl}-1,5-dimethyl-5-naphthalen-1-yl-imidazolidin-2,4-dione |

TABLE 1R-continued

| COM. NO. | Formula | Nomenclature |
|---|---|---|
| 70 | | (3-{3-[3-(4-bromo-benzyl)-3 H-imidazol-4-yl]-propyl}-5-methyl-5-naphthalen-1-yl-2,4-dioxo-imidazolidin-1-yl) acetic acid ethyl ester |
| 71 | | 3-[3-(3-imidazol-1-yl-propyl)-5-methyl-5-phenyl-2,4-dioxo-imidazolidin-1-ylmethyl]-benzonitrile |

TABLE 1S

| COM. NO. | Formula | Nomenclature |
|---|---|---|
| 72 | | 4-[5-(3-naphthalen-1-yl-2,5-dioxo-imidazolidin-1-ylmethyl)-imidazol-1-ylmethyl]-benzonitrile |
| 73 | | 3-[3-(4-chloro-benzyl)-3H-imidazol-4-ylmethyl]-1-naphthalen-1-yl-imidazolidin-2,4-dione |

TABLE 1S-continued

| COM. NO. | Formula | Nomenclature |
| --- | --- | --- |
| 74 | | 4-[5-(3-naphthalen-1-yl-2,5-dioxo-imidazolidin-1-ylmethyl)-imidazol-1-ylmethyl]-piperidine-1-carboxylic acid benzyl ester |
| 75 | | 4-[5-(3-naphthalen-1-ylmethyl-2,5-dioxo-imidazolidin-1-ylmethyl)-imidazol-1-ylmethyl]-benzonitrile |

TABLE 1T

| COM. NO. | Formula | Nomenclature |
| --- | --- | --- |
| 76 | | 4-[5-(3-naphthalen-1-ylmethyl-2,4-dioxo-imidazolidin-1-ylmethyl)-imidazol-1-ylmethyl]-piperidine-1-carboxylic acid benzyl ester |

TABLE 1T-continued

| COM. NO. | Formula | Nomenclature |
|---|---|---|
| 77 | | {1-[3-(4-cyano-benzyl)-3H-imidazol-4-ylmethyl]-3-naphthalen-1-ylmethyl-2,5-dioxo-imidazolidin-4-yl}-acetic acid ethyl ester |
| 78 | | {1-[3-(4-cyano-benzyl)-3H-imidazol-4-ylmethyl]-3-naphthalen-1-ylmethyl-2,5-dioxo-imidazolidin-4-yl}-acetic acid |
| 79 | | {1-[3-(4-cyano-benzyl)-3H-imidazol-4-ylmethyl]-3-naphthalen-1-ylmethyl-2,5-dioxo-imidazolidin-(4S)-yl}-acetic acid methyl ester |

TABLE 1U

| COM. NO. | Formula | Nomenclature |
|---|---|---|
| 80 | | 4-{5-[4-(2-morpholin-4-yl-2-oxo-ethyl)-3-naphthalen-1-ylmethyl-2,5-dioxo-imidazolidin-1-ylmethyl]-imidazol-1-ylmethyl}-benzonitrile |

TABLE 1U-continued

| COM. NO. | Formula | Nomenclature |
|---|---|---|
| 81 | | 4-{(5S)-[4-(2-morpholin-4-yl-2-oxo-ethyl)-3-naphthalen-1-ylmethyl-2,5-dioxo-imidazolidin-1-ylmethyl]-imidazol-1-ylmethyl}-benzonitrile |
| 82 | | 2-{1-[3-(4-cyano-benzyl)-3H-imidazol-4-ylmethyl]-3-naphthalen-1-ylmethyl-2,5-dioxo-imidazolidin-4-yl}-N-(2-(N,N-dimethylamino)-ethyl)-acetamide |
| 83 | | 2-{1-[3-(4-bromo-benzyl)-3H-imidazol-4-ylmethyl]-3-naphthalen-1-ylmethyl-2,5-dioxo-imidazolidin-4-yl}-N-(2-methoxy-ethyl)-N-methyl-acetamide |

TABLE 1V

| COM. NO. | Formula | Nomenclature |
|---|---|---|
| 84 | | 4-((5S)-{4-[2-(4-methyl-piperazin-1-yl)-2-oxo-ethyl]-3-naphthalen-1-ylmethyl-2,5-dioxo-imidazolidin-1-ylmethyl}-imidazol-1-ylmethyl)-benzonitrile |

TABLE 1V-continued

| COM. NO. | Formula | Nomenclature |
|---|---|---|
| 85 | | (2S)-(2-{1-[3-(4-cyano-benzyl)-3H-imidazol-4-ylmethyl]-3-naphthalen-1-ylmethyl-2,5-dioxo-imidazolidin-4-yl}-acetylamino)-4-methylsulfanyl-butyric acid methyl ester |
| 86 | | (2S)-(2-{1-[3-(4-cyano-benzyl)-3H-imidazol-4-ylmethyl]-3-naphthalen-1-ylmethyl-2,5-dioxo-imidazolidin-4-yl}-acetylamino)-4-methylsulfanyl-butyric acid |
| 87 | | 3-(3-imidazol-1-yl-propyl)-1-naphthalen-1-yl-imidazolidin-2,4-dione |

It is another object of the present invention to provide a process for preparing the hydantoin derivative of formula (I) as defined above.

According to the present invention, the hydantoin derivative of formula (I) can be prepared by a process characterized in that 1) a compound represented by the following formula (II):

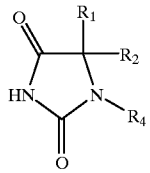

[Formula II]

wherein $R_1$, $R_2$ and $R_4$ are defined as previously described, is reacted under Mitsunobu reaction condition with an alcohol derivative represented by the following formula (III):

 [Formula III]

wherein $R_3$ is defined as previously described, or 2) a compound represented by the following formula (IIa):

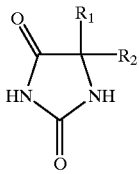

[Formula IIa]

wherein $R_1$ and $R_2$ are defined as previously described, is reacted with the alcohol derivative of formula (III) under Mitsunobu reaction condition to produce a compound represented by the following formula (Ia):

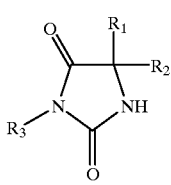

[Formula Ia]

wherein $R_1$, $R_2$ and $R_3$ are defined as previously described, then substituent $R_4'$ is introduced into the resulting compound of formula (Ia) to produce a compound represented by the following formula (Ib):

[Formula Ib]

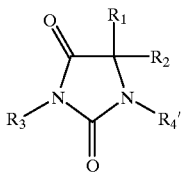

wherein $R_1$, $R_2$ and $R_3$ are defined as previously described and $R_4'$ is the same as $R_4$ except that $R_4'$ is not hydrogen.

While, the starting compounds used in the above reaction may be prepared according to the processes depicted in the following Schemes 1 to 9. First, the compound of formula (IIa) can be synthesized by condensing a ketone compound with potassium cyanide and ammonium carbonate as represented in the following Reaction Scheme 1:

[Reaction Scheme 1]

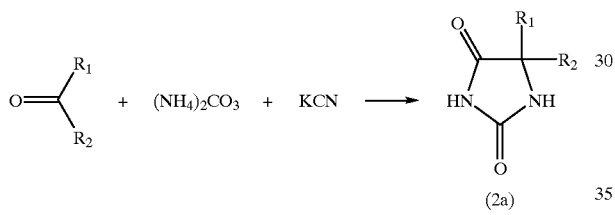

As represented in the following Reaction Scheme 2, the compound of formula (II) can be prepared from ethyl bromoacetate by alkylation of amine compound and cyclization:

[Reaction Scheme 2]

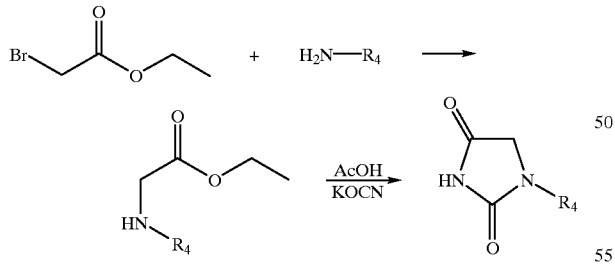

Further, the compound of formula (II) may be obtained by processes represented in the following Reaction Schemes 3 and 4. Specifically, a racemate can be obtained through the alkylation of an amine compound using fumarate and then cyclization as Reaction Scheme 3, and a stereospecific isomer can be obtained through the reductive amination of an aspartic acid having ester protecting group with an aldehyde compound and then cyclization as Reaction Scheme 4:

[Reaction Scheme 3]

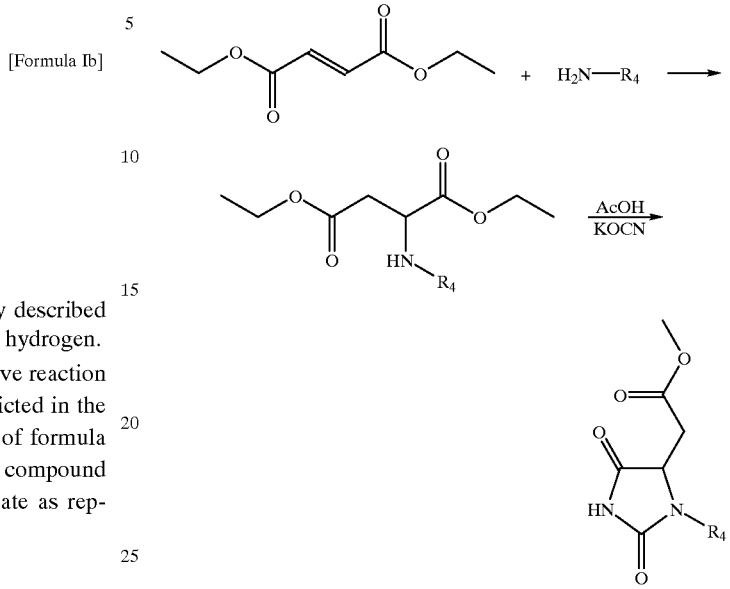

[Reaction Scheme 4]

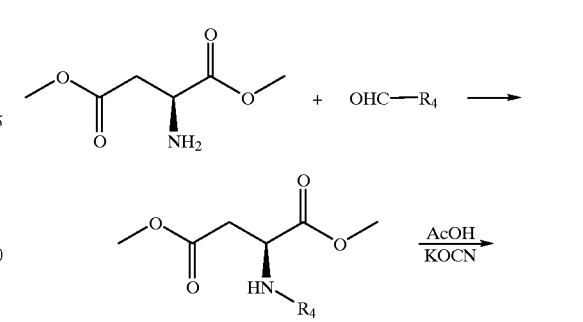

The alcohol compound of formula (III) may be prepared by processes described in the following Reaction Schemes 5 to 9. That is, the compound 3 can be synthesized by forming imidazole moiety using dihydroxy acetone as Reaction Schemes 5 and 6, or by alkylating the existing imidazole methanol compound as Reaction Scheme 7. Also, the compound of formula (III) may be prepared by processes described in the following Reaction Schemes 8 and 9.

[Reaction Scheme 5]

[Reaction Scheme 6]

[Reaction Scheme 7]

[Reaction Scheme 8]

[Reaction Scheme 9]

In the above Reaction Schemes, AcOH represents acetic acid, Cbz-Cl represents benzyloxycarbonyl chloride, Trt-Cl represents chlorotriphenylmethane and TFA represents trifluoroacetic acid. The process for preparing the compound of formula (I), particularly the synthetic methods as described above will be more specifically explained by the following Preparations and Examples.

As the coupling agent used in the above amidation reaction for preparing the compound of formula (I), a mixture of carbodiimides such as dicyclohexylcarbodiimide (DCC), 1-ethyl-3-(3-dimethylaminopropyl)carbodiimide (EDC), 1,1'-dicarbonyldiimidazole(CDI), etc., and 1-hydroxybenzotrizole can be mentioned.

Reaction conditions including the amount of reactants, temperature, reaction time, etc. can be easily determined by the person having ordinary skill in the art depending on the reactant used.

Also, the free compound of formula (I) produced in the aforementioned reaction may be easily converted into a salt form thereof according to the conventionally known methods in this art.

After the reaction is completed, the resulting product may be further separated and purified by usual work-up processes, such as for example, chromatography, recrystallization, etc.

The compound of formula (I) shows an inhibitory, activity against farnesyl transferase, and thus can be effectively used as an anti-cancer agent.

Therefore, the present invention also provides an anti-cancer agent comprising the novel compound of formula (I), as defined above, or a pharmaceutically acceptable salt thereof as an active ingredient together with a pharmaceutically acceptable carrier.

When the active compound according to the present invention is used for clinical purpose, it is preferably administered in an amount ranging from 10 mg to 40 mg per kg of body weight a day. The total daily dosage may be administered in one time or over several times. However, the specific administration dosage for the patient can be varied with the specific compound used, body weight of the subject patient, sex, hygienic condition, diet, time or method of administration, excretion rate, mixing ratio of the agent, severity of the disease, to be treated, etc.

The compound of the present invention may be administered in the form of injections or oral preparations. Injections, for example, sterilized aqueous or oily suspension for injection, can be prepared according to the known procedure using suitable dispersing agent, wetting agent, or suspending agent. Solvents which can be used for preparing injections include water, Ringer's fluid and NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (I) according to the present invention with at least one carrier selected from a group consisting of inactive diluents such as sucrose, lactose, starch, etc., lubricants such as magnesium stearate, disintegrating agent and binding agent.

The present invention will be more specifically explained in the following examples. However, it should be understood that the following examples are intended to illustrate the present invention but not in any manner to limit the scope of the present invention. Processes for preparing the starting substances used for obtaining the compound of formula (I) will be explained in the following Preparations.

Preparation 1

Synthesis of 5-methyl-5-naphthalen-1-yl-imidazolidin-2,4-dione 30 g(0.18 mol) of 1'-acetonaphthone and 23 g(0.35 mol) of potassium cyanide[KCN] were dissolved in 900 ml of methanol. Then, 169 g(1.8 mol) of ammonium carbonate [$(NH_4)_2CO_3$] in 900 ml of distilled water were added thereto and the resulting solution was stirred for 12 hours at 70° C. The reaction solution was distilled under reduced pressure to remove methanol and the residue was extracted with ethyl acetate(500 ml×4). The extract was distilled under reduced pressure to remove ethyl acetate and 38.2 g (Yield: 90%) of title compound was obtained.

$^1$H NMR($CDCl_3$) δ(ppm) 2.15(3H, s), 6.35(1H, s), 7.44 (1H, t), 7.53(2H, m), 7.70(1H, d), 7.89(1H, d), 7.93(1H, d), 7.99(1H, d), 8.52(1H, br)

FAB Mass(M+H): 241

Preparation 2

Synthesis of 1-naphthalen-1-yl-imidazolidin-2,4-dione 2-1) Synthesis of (naphthalen-1-yl-amino)-acetic acid ethyl ester 19.3 g(139 mmol) of potassium carbonate was added to 200 ml of dimethylformamide, and then the solution was heated to dissolve potassium carbonate. After cooling to room temperature, 8 ml(70 mmol) of ethyl bromoacetate and 10 g(70 mmol) of 1-naphthylamine were added to the solution, which was then stirred for 48 hours. DMF was removed under reduced pressure and ethyl acetate was added to the residue. The ethyl acetate layer was washed with water 4 times and saturated sodium chloride solution. Ethyl acetate was removed under reduced pressure, and then column chromatography was performed using a mixed solution(9:1) of hexane and ethyl acetate as an eluent to obtain 12 g of the title compound(Yield 75%, MW 229).

$^1$H NMR($CDCl_3$) δ(ppm) 1.33(3H, t), 4.07(2H, s), 4.30 (2H, q), 6.24(1H, d), 7.30(1H, d), 7.34(1H, t), 7.47(2H, m), 7.80(1H, m), 7.95(1H, m)

FAB (M+H) 230 2-2) Synthesis of 1-naphthalen-1-yl-imidazolidin-2,4-dione 8.68 g(37.9 mmol) of the compound prepared in Preparation 2-1) and 6.34 g(75.8 mmol) of potassium isocyanate were added to 100 ml of acetic acid and the solution was stirred for 24 hours at 110° C. Acetic acid was removed under reduced pressure and then ethyl acetate was added to the residue. The resulting, solution was washed with water 3 times, 1N HCl solution, saturated sodium bicarbonate solution, and saturated sodium chloride solution, respectively. The solution was recrystallized from ethyl acetate to obtain 6.8 g of the title compound(Yield 80%, MW 226).

$^1$H NMR($CD_3OD$) δ(ppm) 4.49(2H, s), 7.52–7.61(4H, m), 7.89–7.98(3H, m)

FAB (M+H) 227

Preparation 3

Synthesis of 1-(naphthalen-1-ylmethyl)-2,4-dioxo-imidazolidin-5-yl]acetic acid ethyl ester 3-1) Synthesis of 2-[(naphthalen-1-ylmethyl)-amino]succinic acid diethyl ester 3.12 ml(19.0 mmol) of diethyl fumarate and 3.0 g(19 mmol) of 1-aminomethyl naphthalene were added to acetonitrile, and then the solution was refluxed for 12 hours. Acetonitrile was removed under reduced pressure and column chromatography was performed using a mixed solution of hexane and ethyl acetate(3:1) as an eluent to obtain 4.57 g of the title compound(Yield 73%, MW 329).

$^1$H NMR (CDCl$_3$) δ(ppm) 1.19(3H, t), 1.30(3H, t), 2.18(1H, br), 2.70 (2H, 2dd), 3.79(1H, dd), 4.03–4.13(2H, m) 4.15(1H, d), 4.23(2H, q), 4.35 (1H, d), 7.41(1H t), 7.45–7.55(3H, m), 7.77(1H, d), 7.85(1H, d), 8.20(1H, d)

FAB (M+H) 330

3-2) Synthesis of [1-(naphthalen-1-ylmethyl)-2,4-dioxo-imidazolidin-5-yl]acetic acid ethyl ester 4.57 g(13.9 mmol) of the compound prepared in Preparation 3-1) and 3.38 g(41.7 mmol) of potassium isocyanate were added to 150 ml of acetic acid and the solution was stirred for 24 hours at 110° C. Acetic acid was removed under reduced pressure and ethyl acetate was added to the residue. The resulting solution was washed with water 3 times, 1N HCl solution, saturated sodium bicarbonate solution and saturated sodium chloride solution, respectively. Ethyl acetate was removed under reduced pressure and then column chromatography was performed using a mixed solution of hexane and ethyl acetate(1:1) as an eluent to obtain 3.85 g of the title compound(Yield 85%, MW 326).

$^1$H NMR (CDCl$_3$) δ(ppm) 1.08(3H, t), 2.70(2H, 2dd), 3.80(1H, m), 3.90(2H, m), 4.80(1H, d), 5.30(1H, d), 7.38–7.46(2H, m), 7.51(1H, t), 7.57(1H, m), 7.83(1H, m), 7.87(1H, d), 8.10(1H, d), 9.27(1H, s)

FAB (M+H) 327

Preparation 4

Synthesis of [1-(naphthalen-1-ylmethyl)-2,4-dioxo-imidazolidin-(5S)-yl]acetic acid methyl ester 4-1) Synthesis of (2S)-[(naphthalen-1-ylmethyl)-amino]succinic acid diethyl ester 2.22 g(11.2 mmol) of (S)-dimethyl aspartate hydrochloride and 1.6 ml(11.2 mmol) of 1-naphthyl aldehyde were added to 50 ml of dimethylformamide, and then the solution was stirred for 1 hour. 5.0 g(22.4 mmol) of sodium triacetoxy borohydride was added to the solution and the resulting solution was stirred for 4 hours. Then, DMF was removed in vacuo and then ethyl acetate was added thereto. The solution was washed with water and saturated sodium chloride solution. Ethyl acetate was removed under reduced pressure and column chromatography was performed on the residue using a mixed solution of hexane and ethylacetate (3:1) as an eluent to obtain 3.00 g of the title compound (Yield 89%, MW 301).

$^1$H NMR (CDCl$_3$) δ(ppm) 2.23(1H, br), 2.74(2H, 2dd), 3.60(3H, s), 3.77 (3H, s), 3.81(1H, dd), 4.15(1H, d), 4.34 (1H, d), 7.41(1H, t), 7.44–7.55(3H, m), 7.77(1H, d), 7.84 (11H d), 8.18(1H, d)

FAB (M+H) 302

4-2) Synthesis of [1-(naphthalen-1-ylmethyl)-2,4-dioxo-imidazolidin-(5S)-yl]acetic acid methyl ester 3.00 g(9.96 mmol) of the compound prepared in Preparation 4-1) and 2.2 g (26 mmol) of potassium isocyanate were added to 50 ml of acetic acid and then the solution was stirred for 30 minutes at 110° C. Acetic acid was removed under reduced pressure and ethyl acetate was added to the residue. The resulting solution was washed with water 3 times, 1N HCl solution, saturated sodium bicarbonate solution and saturated sodium hydroxide solution, respectively. Ethyl acetate was removed under reduced pressure to obtain 2.87 g of the title compound(Yield 92%, MW 312).

$^1$H NMR (CD$_3$OD+CDCl$_3$) δ(ppm) 2.45(2H, 2dd), 3.09 (3H, s), 3.75(1H, t), 4.79(2H, dd), 7.20(1H, m), 7.27–7.37 (2H, m), 7.63(1H, d), 7.66(1H, d), 7.90 (1H, d)

FAB (M+H) 313

Preparation 5

Synthesis of 4-(5-hydroxymethyl-imidazol-1-ylmethyl)-piperidine-1-carboxylic acid benzyl ester 5-1) Synthesis of 4-aminomethyl-piperidine-1-carboxylic acid benzyl ester 22.2 g(0.2 mol) of 4-aminomethyl piperidine was dissolved in 250 ml of toluene and 21.2 g(0.2 mol) of benzaldehyde was added thereto. The reaction mixture was heated to reflux for 3 hours with Dean-stack and then cooled down to 0° C. 34.2 g(0.2 mol) of benzyl chloroformate was added dropwise while stirring. The reactants were stirred for 3 hours and 220 ml of 1N KHSO$_4$ was added at room temperature. The reaction solution was extracted with 200 ml of diethylether 3 times and the aqueous layer was basified with sodium hydroxide. After the aqueous solution was treated with saturated sodium chloride solution, it was extracted with 100 ml of dichloromethane 3 times. and the organic layer was dried over magnesium sulfate. Removal of dichloromethane under reduced pressure provided 38 g of the title compound(Yield 91%, MW 248).

$^1$H NMR(CDCl$_3$) δ(ppm) 1.11(2H, s), 1.49(3H, s), 1.70 (2H, d), 2.57(2H, d), 2.78(2H, s), 4.20(2H, s), 5.12(2H, s), 7.34–7.35(5H, m)

FAB (M+H) 249

5-2) Synthesis of 4-(5-hydroxymethyl-2-mercapto-imidazol-1-ylmethyl)-piperidine-1-carboxylic acid benzyl ester 24.8 g(0.1 mol) of the compound prepared in Preparation 5-1) was dissolved in 50 ml of n-butanol with 6.0 g(0.1 mol) of acetic acid. Above solution was added to 50 ml of n-butanol solution in which 12.6 g(0.13 mol) of potassium thiocyanate, 15.2 g(0.1 mol) of 1,3-dihydroxyacetone dimer and 10.0 g(0.17 mol) of acetic acid were dissolved, and then the resulting solution was stirred for 48 hours. After stirring, the solvent was removed under the reduced pressure and 200 ml of ethyl acetate was added thereto. The resulting solution was washed with 100 ml of water 3 times and the organic layer was dried over magnesium sulfate. The solvent was removed under reduced pressure to obtain 27 g of the title compound(Yield 75%, MW 361).

$^1$H NMR(CDCl$_3$) δ(ppm) 1.22(2H, d), 1.57(2H, d), 2.30 (1H, s), 2.72(2H, s), 3.96(2H, s), 4.15(2H, d), 4.46(2H, s), 5.10(2H, s), 6.62(1H, s), 7.26–7.37(5H, m)

FAB (M+H) 362

5-3) Synthesis of 4-(5-hydroxymethyl-imidazol-1-ylmethyl)-piperidine-1-carboxylic acid benzyl ester 18.05 g(50 mmol) of the compound prepared in Preparation 5-2) was added to a mixed solution of 100 ml of 10% nitric acid solution and 10 ml of ethyl acetate at 0° C. It was stirred for 3 hours at room temperature. The reaction solution was basified with 4N aqueous sodium hydroxide solution and then extracted with 100 ml of ethyl acetate twice.

The extracted organic solution was dried over magnesium sulfate. The solvent was removed under reduced pressure to give 12.3 g of the title compound(Yield 75%, MW 329).

$^1$H NMR(CDCl$_3$) δ(ppm) 1.16(2H, d), 1.56(2H, d), 1.98 (1H, s), 2.70(2H, s), 3.88(2H, d), 4.18(2H, s), 4.49(1H, s), 4.56(3H, s), 5.10(2H, s), 6.82 (1H, s), 7.27–7.40(5H, m)

FAB (M+H) 330

Preparation 6

Synthesis of 1-(4-bromobenzyl)-5-hydroxymethyl-imidazole 8.9 g(40 mmol) of 4-bromobenzylamine hydrochloride and 4 ml of acetic acid were dissolved in 85 ml of n-butanol. 5.19 g(50 mmol) of potassium thiocyanate and 3.21 g(20 mmol) of 1,3-dihydroxyacetone dimer were added to the solution. The resulting solution was stirred for 4 days and then filtered under reduced pressure to separate the precipitated solid, which was then washed with water and diethylether. The solid thus obtained was added to 10% nitric acid solution, and then the mixture was stirred for 3 hours, filtered under reduced pressure to remove the insoluble impurities. Then, the solution was basified with 4N sodium hydroxide solution to precipitate a solid product. This solid product was washed with water several times and dried under vacuum to give 6.7 g of the title compound(Yield 60%, MW 266).

$^1$H NMR(CDCl$_3$) δ(ppm) 4.45(2H, s), 5.20(2H, s), 6.94 (1H, s), 7.03(2H, d), 7.18(4H, m)

FAB Mass (M+H) 267

Preparation 7

Synthesis of 4-(5-hydroxymethyl-imidazol-1-ylmethyl)-benzonitrile 7-1) Synthesis of 1-trityl-4-hydroxymethyl-imidazole 7.98 g(59.2 mmol) of hydroxymethyl imidazole hydrochloride was dissolved in a solvent mixture of 60 ml of dimethylformamide and 20 ml of triethylamine. 200 ml of dimethylformamide solution containing 18.7 g (67 mmol) of triphenylmethyl chloride was added slowly thereto. After 2 hours, 1000 ml of ice water was added thereto to obtain a solid. This solid was recrystallized from dioxane to give 17.6 g of the title compound(Yield 87%, MW 340).

mp 227–229° C.

7-2) Synthesis of 1-trityl-4-hydroxymethyl-imidazole acetate 10.0 g(29.4 mmol) of the compound prepared in Preparation 7-1) was added to 200 ml of pyridine and then, 3.30 g((32.4 mmol) of acetic anhydride was added. After stirring for 24 hous at room temperature pyridine was removed under reduced pressure. The residue was dissolved in 400 ml of ethylacetate, and then washed with 200 ml of saturated sodium chloride solution. After removal of ethyl acetate under reduced pressure, chromatography was performed on the residue using dichloromethane/methanol(95:5) as an eluent to obtain 10.44 g of the title compound(Yield 93%, MW 382).

$^1$H NMR(CDCl$_3$) δ(ppm) 2.01(3H, s), 4.95(2H, s), 6.88 (1H, s), 7.08(5H, s), 7.27(10H, s), 7.45(1H, s)

FAB (M+H) 383

7-3) Synthesis of 1-trityl-3-(4-cyanobenzyl)-imidazol-4-ylmethyl acetate bromide 10.0 g(26.2 mmol) of the compound prepared in Preparation 7-2) was dissolved in 40 ml of dichloromethane and 5.64 g(28.8 mmol) of 4-cyanobenzyl bromide was added thereto. The resulting solution was stirred for 60 hours at room temperature and dichloromethane was removed under reduced pressure. Column chromatography was performed with the residue using dichloromethane/methanol(95:5) as an eluent to obtain 10.62 g of the title compound(Yield 70%, MW 578).

$^1$H NMR(CDCl$_3$/CD$_3$OD) δ(ppm) 1.95(3H, s), 4.95(2H, s), 5.45(2H, s), 7.11–7.40(18H, m), 7.65(2H, d), 8.21(1H, s)

FAB (M+H) 579

7-4) Synthesis of 1-(4-cyanobenzyl)-imidazol-5-ylmethyl acetate 9.10 g(15.7 mmol) of the compound prepared in Preparation 7-3) was dissolved in 500 ml of dichloromethane and 6.06 ml (78.7 mmol) of trifluoroacetic acid and 12.5 ml (78.7 mmol) of triethylsilane were added slowly thereto at 0° C. The resulting solution was stirred for 1 hour at room temperature. After removal of dichloromethane under reduced pressure, pH was adjusted to pH 10 using saturated potassium carbonate solution. This solution was extracted with 300 ml of ethyl acetate and ethyl acetate was removed under reduced pressure. Column chromatography was performed with the residue using ethyl acetate as an eluent to obtain 3.60 g of the title compound(Yield 90%, MW 255).

$^1$H NMR(CDCl$_3$) δ(ppm) 1.90(3H, s), 4.97(2H, s), 5.25 (2H, s), 7.14(2H, d), 7.21(1H, d), 7.67(1H, s), 7.75(2H, d)

FAB (M+H) 256

7-5) Synthesis of 4-(5-hydroxymethyl-imidazol-1-ylmethyl)-benzonitrile 3.36 g(13.2 mmol) of the compound prepared in Preparation 7-4) was dissolved in 160 ml of methanol and 3.60 g(26.3 mmol) of K$_2$CO$_3$ was added thereto. After stirring for 20 minutes at room temperature, methanol was removed under reduced pressure and product was extracted with 250 ml of ethyl acetate. Column chromatography was performed using dichloromethane/methanol(95:5) as an eluent to obtain 2.55 g, of the title compound(Yield 91%, 0%, MW 213).

$^1$H NMR (CDCl$_3$/CD$_3$OD) δ(ppm) 4.28(2H, s), 5.18(2H, s), 6.84(1H, s), 7.12(2H, d), 7.42(1H, s), 7.55(2H, d)

FAB (M+H) 213

Preparation 8

Synthesis of 3-imidazol-1-yl-propanol 8-1) Synthesis of methyl 3-imidazol-1-yl-propionate 5.0 g(73.4 mmol) of imidazole and 12.6 g(148.6 mmol) of methyl acrylate were dissolved in 100 ml of acetonitrile, and then refluxed for 8 hours. Acetonitrile and the excess methyl acrylate was removed under reduced pressure. Then, 200 ml of ethyl acetate was added to the residue and the solution thus obtained was washed with saturated sodium chloride solution. Removal of ethyl acetate under reduced pressure provided 11.1 g(Yield: 90%) of the title compound.

$^1$H NMR(CDCl$_3$) δ(ppm) 2.75(2H, t), 3.46(3H, s), 4.24 (2H, t), 6.89(1H, s), 7.00(1H, s), 7.46(1H, s)

FAB Mass(M+H): 169

8-2) Synthesis of 3-imidazol-1-yl-propanol

To the 1.1 g(6.6 mmol) of the compound prepared in Preparation 8-1) in 50 ml of tetrahydrofuran was added 0.26 g(6.6 mmol) of lithium aluminum hydride[LiAlH$_4$] and then the resulting mixture was refluxed for one hour. Then, 20 ml of 1N sodium hydroxide solution was added to the reaction mixture which was then extracted with ethyl acetate. Removal of the organic solvent under reduced pressure provided 0.77 g(Yield: 93%) of the title compound was obtained.

$^1$H NMR(CDCl$_3$) δ(ppm) 1.67(2H, m), 3.26(2H, t), 3.78 (2H, t), 6.60(1H, s), 6.75(1H, s), 7.14(1H, s)

FAB Mass(M+H): 127

Preparation 9

Synthesis of 2-imidazol-1-yl-ethanol 9-1) Synthesis of 2-imidazol-1-yl-acetic acid ethyl ester 5.0 g (73.4 mmol) of imidazole and 3.36 ml(29.4 mmol) of ethyl bromoacetate were dissolved in 50 ml of dimethylformamide and stirred for 4 hours. Dimethylformamide was removed in vacuo. Then, 100 ml of ethyl acetate was added to the residue and it was washed with saturated sodium chloride solution. Removal of the organic solvent under reduced pressure provided 0.77 g(Yield: 17%) of the title compound.

$^1$H NMR(CDCl$_3$) δ(ppm) 1.29(3H, t), 4.25(2H, q), 4.70 (2H, s), 6.95(1H, s), 7.10(1H, s), 7.49(1H, s)

FAB Mass(M+H): 155

9-2) Synthesis of 2-imidazol-1-yl-ethanol

To the 20 ml of tetrahydrofuran solution of 0.77 g(5.0 mmol) of the compound prepared in Preparation 9-1) was added 0.2 g(5.0 mmol) of lithium aluminum hydride and then the resulting mixture was refluxed for one hour. Then, 10 ml of 1N sodium hydroxide solution was added to the reaction mixture, and it was extracted with ethyl acetate. The organic solvent was removed under reduced pressure and the residue was subjected to chromatography using a solvent mixture of methanol-methylene chloride(5:95) as the eluent to obtain 0.51 g(Yield: 91%) of the title compound.

$^1$NMR(CDCl$_3$) δ(ppm) 3.78(2H, t), 3.98(2H, t), 6.85(1H, s), 6.94(1H, s), 7.3(1H, s)

FAB Mass(M+H): 113

EXAMPLE 1

Synthesis of 2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid methyl ester(Compound 1)

1-1) Synthesis of 3-[3-(1-triphenylmethyl-imidazol-4-yl)-propyl]-5-methyl-5-naphthalen-1-yl-imidazolidin-2,4-dione 0.60 g(2.5 mmol) of 5-methyl-5-naphthalen-1-yl-imidazolidin-2,4-dione prepared in Preparation 1, 1.02 g(2.76 mmol) of 3-(1-triphenylmethyl-imidazol-4-yl)-propanol and 0.87 g(3.3 mmol) of triphenylphosphine (Ph$_3$P) were dissolved in 50 ml of tetrahydrofuran. 0.52 ml(3.3 mmol) of diethylazodicarboxylate[DEAD] was added thereto and the resulting solution was stirred for 24 hours. Tetrahydrofuran was removed under reduced pressure and the residue was subjected to chromatography using ethyl acetate the eluent to obtain 1.17 g(Yield: 80%) of the title compound.

$^1$H NMR(CDCl$_3$) δ(ppm) 2.04(5H, m), 2.60(2H, t), 3.67 (2H, t), 6.59(1H, s), 7.05(1H, s), 7.15(6H, m), 7.32(9H, m), 7.37(1H, t), 7.44(2H, d), 7.63(1H, d), 7.79(1H, d), 7.86(1H, d), 7.91(1H, d)

FAB Mass(M+H): 591

1-2) Synthesis of 2-{3-[3-(1-triphenylmethyl-imidazol-4-yl)-propyl]-5-methyl-5-naphthalen-1-yl-2,4-dioxo-imidazolidin-1-yl}-acetic acid ethyl ester 0.082 g(0.14 mmol) of 3-[3-(1-triphenylmethyl-imidazol-4-yl)-propyl]-5-methyl-5-naphthalen-1-yl-imidazolidin-2,4-dione prepared in Example 1-1) and 0.023 ml(0.21 mmol) of ethyl bromoacetate were dissolved in 5 ml of dimethylformamide. 0.017 g(0.21 mmol) of sodium hydride [NaH] was added thereto and the resulting solution was stirred for one hour. Dimethylformamide was removed under reduced pressure and the residue was dissolved in ethyl acetate and then washed with saturated sodium chloride solution. Removal of ethyl acetate under reduced pressure provided 0.092 g(Yield: 99%) of title compound.

1H NMR(CDCl$_3$) δ(ppm) 1.10(3H, t), 2.02(3H, s), 2.15 (2H, m), 2.70(2H, t), 3.80(2H, t), 4.02(2H, m), 4.10(2H, q), 6.60(1H, s), 7.13(6H, m), 7.33(11H, m), 7.46(3H, m), 7.69 (1H, d), 7.89(2H, m)

FAB Mass(M+H): 677

1-3) Synthesis of 2-(2-{3-[3-(1-triphenylmethyl-imidazol-4-yl)-propyl]-5-methyl-5-naphthalen-1-yl-2,4-dioxo-imidazolidin-1-yl}-acetylamino)-4-methyl sulfanyl-butyric acid methyl ester 0.092 g(0.14 mmol) of 2-{3-[3-(1-triphenylmethyl-imidazol-4-yl)-propyl]-5-methyl-5-naphthalen-1-yl-2,4-dioxo-imidazolidin-1-yl}-acetic acid ethyl ester prepared in Example 1-2) was dissolved in 4 ml of a solvent mixture of tetrahydrofuran- distilled water(3:1). 0.0058 g(0.14 mmol) of lithium hydroxide[LiOH] was added thereto and the resulting solution was stirred for one hour. The solvents were removed under reduced pressure and the residue was thoroughly dried under vacuum. The residue thus produced was dissolved in 5 ml of dimethylformamide. Then, 0.041 g (0.21 mmol) of methionine methyl ester, 0.037 g(0.28 mmol) of N-hydroxy benzotriazole and 0.04 g(0.28 mmol) of 3-ethyl-(dimethyl amino)-propylcarbodiimide hydrochloride were added to the resulting solution and stirred for 12 hours at room temperature. After removal of dimethylformamide under reduced pressure, 30 ml of ethyl acetate was added. The resulting solution was washed twice with 10 ml of saturated potassium carbonate solution and 10 ml of saturated sodium chloride solution, sequentially. Then, chromatography using a solvent mixture of ethyl acetate-hexane (1:1) as the eluent was carried out to obtain 0.11 g(0.13 mmol, Yield: 95%) of the title compound.

$^1$H NMR(CDCl$_3$) δ(ppm) 1.84(2H, m), 1.98(6H, m), 2.14(2H, m), 2.40(2H, t), 2.71(2H, t), 3.38(1H, dd), 3.62 (3H, s), 3.80(2H, m), 4.46(1H, m), 6.64(1H, d), 6.75(1H, dd), 7.14(6H, m), 7.24–7.53(13H, m), 7.72(1H, d), 7.89(2H, m)

FAB Mass(M+H): 794

1-4) Synthesis of 2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid methyl ester 0.11 g(0.13 mmol) of 2-(2-{3-[3-(1-triphenylmethyl-imidazol-4-yl)-propyl]-5-methyl-5-naphthalen-1-yl-2,4- dioxo-imidazolidin-1-yl}-acetylamino)-4-methylsulfanyl-butyric acid methyl ester prepared in Example 1-3) and 0.053 ml(0.26 mmol) of triisopropylsilane were dissolved in 5 ml of methylene chloride. Then, 5 ml of trifluoroacetic acid was added thereto and the resulting solution was stirred for one hour at room temperature. The organic solvent was removed under reduced pressure and saturated potassium carbonate[$K_2CO_3$] solution was added. The solution was extracted with 10 of ethyl acetate and the solvent was removed under reduced pressure. The residue was subjected to chromatography using a solvent mixture of methanol-methylene chloride(5:95) as the eluent to obtain 0.068 g(Yield: 95%) of the title compound.

$^1$H NMR(CDCl$_3$) δ(ppm) 1.88(2H, m), 2.00(3H, s), 2.06 (3H, s), 2.14(2H, m), 2.45(2H, t), 2.76(2H, m), 3.38(1H, dd), 3.69(3H, d), 3.82(2H, m), 4.54(1H, m), 6.87(1H, d), 7.60–7.40(5H, m), 7.72(1H, d), 7.91(2H, m)

FAB Mass(M+H): 552

EXAMPLE 2

Synthesis of 2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid (Compound 2) lithium salt 0.068 g(0.12 mmol) of 2-(2-{3-[3-(1H-imidazol-4-yl)-propyl]-5-methyl-5-naphthalen-1-yl-2,4-dioxo-imidazolidin-1-yl}-acetylamino)-4-methyl sulfanyl-butyric acid methyl ester prepared in Example 1 was dissolved in 4 ml of a solvent mixture of tetrahydrofuran-distilled water (3:1). 0.005 g (0.12 mmol) of lithium hydroxide was added thereto and stirred for one hour. After solvents were removed under reduced pressure, the residue was thoroughly dried under vacuum to obtain 0.06 g(Yield 95%) of the title compound.

ESI Mass(M+Li$^+$): 538

EXAMPLE 3

Synthesis of 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid methyl ester(Compound 3)

0.032 g of the title compound was prepared according to the same procedure as Example 1 except that 2-(1-triphenylmethyl-imidazol-4-yl)-ethanol was used instead of 3-(1-triphenylmethyl-imidazol-4-yl)-propanol in Example 1-1).

$^1$H NMR(CDCl$_3$) δ(ppm) 1.88(2H, m), 2.01(3H, s), 2.08 (3H, s), 2.20(1H, t), 2.45(1H, t), 3.20(2H, m), 3.37(1H, dd), 3.70(3H, d), 4.05(2H, m), 4.54(1H, m), 6.97(1H, s), 7.71–7.30(6H, m), 7.90(2H, m)

FAB Mass(M+H): 538

EXAMPLE 4

Synthesis of 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid (Compound 4) lithium salt 0.02 g of the title compound was prepared according to the same procedure as Example 2 using 0.03 g(0.056 mmol) of 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid methyl ester prepared in Example 3.

ESI Mass(M–Li$^+$+2H): 524

EXAMPLE 5

Synthesis of 2-{2-[3-(3H-imidazol-4-yl-methyl)-5-methyl-5-naphthaten-1-yl-2,4-dioxo-imidazolidin-1-yl]-acetylamino}-4-methylsulfanyl-butyric acid methyl ester(Compound 5)

0.025 g of the title compound was prepared according to the same procedure as Example 1 except that (3-triphenylmethyl-imidazol-4-yl)-methanol was used instead of 3-(1-triphenylmethyl-imidazol-4-yl)-propanol in Example 1-1).

$^1$H NMR(CDCl$_3$) δ(ppm) 1.80(2H m), 1.98(3H, s), 2.00 (3H, s), 2.08(1H, t), 2.38(1H, t), 3.38(1H, dd), 3.67(3H, d), 4.45(1H, m), 4.88(2H, d), 6.80(1H, m), 7.08(3H, m), 7.34 (1H, m), 7.45(1H, m), 7.68(1H, d), 7.82(2H, m)

FAB Mass(M+1): 524

EXAMPLE 6

Synthesis of 2-{2-[3-(3H-imidazol-4-yl-methyl)-5-methyl-5-naphthalen-1-yl-2,4-dioxo-imidazolidin-1-yl]-acetylamino}-4-methylsulfanyl-butyric acid (Compound 6) lithium salt 0.015 g, of the title compound was prepared according to the same procedure as Example 2 using 0.02 g(0.038 mmol) of 2-{2-[3-(3H-imidazol-4-yl-methyl)-5-methyl-5-naphthalen-1-yl-2,4-dioxo-imidazolidin-1-yl]-acetylamino}-4-methylsulfanyl-butyric acid methyl ester prepared in Example 5.

ESI Mass(M–Li$^+$+2H): 510

EXAMPLE 7

Synthesis of 2-(2-{3-[3-(4-cyano-benzyl)-imidazol-4-yl-methyl]-5-methyl-5-naphthalen-1-yl-2,4-dioxo-imidazolidin-1-yl}-acetylamino)-4-methylsulfanyl-butyric acid methyl ester(Compound 7)

0.04 g of the title compound was prepared according to the same procedure as Example 1 except that 1-(4-cyanobenzyl)-5-hydroxymethyl imidazole prepared in Preparation 7 was used instead of 3-(1-triphenylmethyl-imidazol-4-yl)-propanol in Example 1-1).

$^1$H NMR(CDCl$_3$) δ(ppm) 1.85(2H, m), 2.00(3H, s), 2.06 (4H, m), 2.45(1H, t), 3.36(1H, dd), 3.71(3H, d), 4.50(1H, m), 4.71(2H, m), 5.48(2H, dd), 6.90(1H, m), 7.08(1H, m), 7.14(2H, m), 7.39–7.75(7H, m), 7.91(2H, m)

FAB Mass(M+H): 639

EXAMPLE 8

Synthesis of 2-(2-{3-[3-(4-cyano-benzyl)-imidazol-4-yl-methyl]-5-methyl-5-naphthalen-1-yl-2,4-dioxo-imidazolidin-1-yl}-acetylamino)-4-methylsulfanyl-butyric acid(Compound 8) lithium salt 0.025 g of the title compound was prepared according to the same procedure as Example 2 using 0.03 g(0.047 mmol) of 2-(2-{3-[3-(4-cyano-benzyl)-imidazol-4-yl-methyl]-5-methyl-5-naphthalen-1-yl-2,4-dioxo-imidazolidin-1-yl}-acetylamino)-4-methylsulfanyl-butyric acid methyl ester prepared in Example 7.

FAB Mass(M+H): 631

EXAMPLE 9

Synthesis of 2-(2-{3-[3-(3H-imidazol-4-yl)-propyl]-5-methyl-5-naphthalen-1-yl-2,4-dioxo-imidazolidin-1-yl}-acetamino)-3-thiophen-2-yl-propionic acid (Compound 9) lithium salt 0.025 g of the title compound was prepared according to the same procedure as Example 1 and Example 2 except that 3-thiophen-2-yl-propionic acid methyl ester was used instead of methionine methyl ester in Example 1-3).

1H NMR(CD$_3$OD) δ(ppm) 1.95(3H, d), 2.10(2H, m), 2.74(2H, m), 3.20(2H, m), 3.78(2H, t), 4.00(1H, dd), 4.71 (1H, m), 6.68–6.90(3H, m), 7.12(1H, m), 7.34–7.54(5H, m), 7.59(1H, t), 7.99(2H, q)

ESI Mass(M–Li$^+$+2H): 560

EXAMPLE 10

Synthesis of 3-[3-(3H-imidazol-4-yl)-propyl]-5-methyl-5-naphthalen-1-yl-1-(2-oxo-2-thiazolidin-3-yl-ethyl)-imidazolidin-2,4-dione(Compound 10)

0.06 g of the title compound was prepared according to the same procedure as Example 1 except that thiazolidine was used instead of methionine methyl ester in Example 1-3).

$^1$H NMR(CDCl$_3$) δ(ppm) 2.02(3H, s), 2.15(2H, m), 2.70 (2H, t), 3.00(2H, br), 3.75(2H, t), 3.80(2H, t), 4.02(2H, m), 4.50(2H, t), 6.60(1H, s), 7.13(6H, m), 7.33(11H, m), 7.46 (3H, m), 7.69(1H, d), 7.89(2H, m)

FAB Mass(M+H): 478

EXAMPLE 11

Synthesis of 1-[2-(1,1-dioxo-thiazolidin-3-yl)-3-(3H-imidazol-4-yl)-propyl]-5-methyl-5-naphthalen-1-yl-imidazolidin-2,4-dione(Compound 11)

0.05 g of the title compound was prepared according to the same procedure as Example 1 except that 1,1-dioxo-thiazolidine was used instead of methionine methyl ester in Example 1-3).

$^1$H NMR(CDCl$_3$) δ(ppm) 2.02(3H, s), 2.15(2H, m), 2.70 (2H, t), 3.24(2H, t), 3.80(2H, t), 4.02(4H, m), 4.40(2H, br), 6.60(1H, s), 7.13(6H, m), 7.33(11H, m), 7.46(3H, m), 7.69 (1H, d), 7.89(2H, m)

FAB Mass(M+H): 510

EXAMPLE 12

Synthesis of 3-[3-(3H-imidazol-4-yl)-propyl]-5-methyl-1-{2-[2-(2-methylsulfanyl-ethyl)-thiazolidin-3-yl]-2-oxo-ethyl}-5-naphthalen-1-yl-imidazolidin-2,4-dione(Compound 12)

0.055 g of the title compound was prepared according to the same procedure as Example 1 except that 2-(2-methylsulfanyl-ethyl)-thiazolidine was used instead of methionine methyl ester in Example 1-3).

$^1$H NMR(CDCl$_3$) δ(ppm) 1.90(1H, m), 2.05(4H, m), 2.15(2H, m), 2.57(2H, m), 2.70(2H, t), 2.85(2H, m), 2.96 (1H, m), 3.32(1H, m), 3.80(2H, t), 4.02(2H, m), 4.52(1H, t), 6.60(1H, s), 7.13(6H, m), 7.33(11H, m), 7.46(3H, m), 7.69 (1H, d), 7.89(2H, m)

FAB Mass(M+H): 552

EXAMPLE 13

Synthesis of 2-(2-{3-[3-(3H-imidazol-4-yl)-propyl]-5-methyl-5-naphthalen-1-yl-2,4-dioxo-imidazolidin-1-yl}-acetylamino)-4-methylsulfonyl-butyric acid (Compound 13) lithium salt The same procedure as Example 1 was carried out except that 4-methyl sulfonyl-butyric acid methyl ester was used instead of methionine methyl ester in Example 1-3), and then the resulting product was treated according to the same procedure as Example 2 to obtain 0.024 g of the title compound.

FAB Mass(M+H): 576

EXAMPLE 14

Synthesis of 2-{2-[3-(3-imidazol-1-yl-propyl)-5-methyl-5-naphthalen-1-yl-2,4-dioxo-imidazolidin-1-yl]-acetylamino}-4-methylsulfanyl-butyric acid (Compound 14) lithium salt The same procedure as Example 1 was carried out except that 3-(imidazol-1-yl)-propanol prepared in Preparation 8 was used instead of 3-(1-triphenylmethyl-imidazol-4-yl)-propanol in Example 1-1), and then the resulting product was treated according to the same procedure as Example 2 to obtain 0.024 g of the title compound ESI Mass(M–Li$^+$+2H): 552

EXAMPLE 15

Synthesis of 2-{2-[3-(2-imidazol -1-yl-ethyl)-5-methyl-5-naphthalen-1-yl-2,4-dioxo-imidazolidin-1-yl]-acetylamino}-4-methylsulfanyl-butyric acid (Compound 15) lithium salt The same procedure as Example 1-1) to 1-3) was carried out except that 2-(imidazol-1-yl)-ethanol prepared in Preparation 9 was used instead of 3-(1-triphenylmethyl-imidazol-4-yl)-propanol in Example 1-1), and then the resulting product was treated according to the same procedure as Example 2 to obtain 0.02 7 g of the title compound.

ESI Mass(M–Li$^+$+2H): 558

EXAMPLE 16

Synthesis of 1-benzyl-3-(3-imidazol-1-yl-propyl)-5-methyl-5-naphthalen-1-yl-imidazolidin-2,4-dione (Compound 16)

The title compound was prepared in a yield of 80% according to the same procedure as Example 1-1) to 1-2) except that 3-(imidazol-1-yl)-propanol was used instead of 3-(1-triphenylmethyl-imidazol-4-yl)-propanol in Example 1-1) ad that benzyl bromide was used instead of ethyl bromoacetate in Example 1-2).

$^1$H NMR(CDCl$_3$) δ(ppm) 1.86(3H, s), 2.27(2H, m), 3.77 (2H, t), 4.07–4.20(3H, m), 4.31(1H, d), 6.78–6.85(2H, m), 6.87(1H, s), 7.03(1H, s), 7.09(3H, m), 7.21(1H, d), 7.32(1H, m), 7.42(1H, t), 7.48(1H, t), 7.57(1H, s), 7.63(1H, d), 7.82(1H, d), 7.87(1H, d)

FAB Mass(M+H): 439

EXAMPLE 17

Synthesis of 1-(pentafluoro-benzyl)-3-(3-imidazol-1-yl-propyl)-5-methyl-5-naphthalen-1-yl-imidazolidin-2,4-dione(Compound 17)

The title compound was prepared in a yield of 87% according to the same procedure as Example 1 except that 3-(imidazol-1-yl)-propanol prepared in Preparation 8 was used instead of 3-(1-triphenylmethyl-imidazol-4-yl)-propanol in Example 1-1) and that pentafluoro-benzyl bromide was used instead of ethyl bromoacetate in Example 1-2).

$^1$H NMR(CDCl$_3$) δ(ppm) 2.10(3H, s), 2.30(2H, m), 3.82 (2H, t), 4.07–4.20(3H, m), 5.11(1H, d), 7.06(1H, s), 7.12

(1H, s), 7.20(1H, d), 7.35–7.50(3H, m), 7.66(1H, d), 7.68–7.80(3H, m)

FAB Mass(M+H): 529

EXAMPLE 18

Synthesis of 1-(3-pyridylmethyl)-3-(3-imidazol-1-yl-propyl)-5-methyl-5-naphthalen-1-yl-imidazolidin-2,4-dione(Compound 18)

The title compound was prepared in a yield of 60% according to the same procedure as Example 1 except that 3-(imidazol-1-yl)-propanol prepared in Preparation 8 was used instead of 3-(1-triphenylmethyl-imidazol-4-yl)-propanol in Example 1-1) and that 3-pyridylmethyl chloride was used instead of ethyl bromoacetate in Example 1-2).

$^1$H NMR(CDCl$_3$) δ(ppm) 1.89(3H, s) 2.30(2H, m), 3.81 (2H, m), 4.15(3H, m), 4.35(1H, d), 6.85(1H, m), 7.08–7.52 (7H, m), 7.65(1H, d), 7.85(3H, m), 7.98(1H, s), 8.21(1H, d)

FAB Mass(M+H): 440

EXAMPLE 19

Synthesis of 1-(3-chloro-benzyl)-3-(3-imidazol-1-yl-propyl)-5-methyl-5-naphthalen-1-yl-imidazolidin-2,4-dione(Compound 19)

The title compound was prepared in a yield of 90% according to the same procedure as Example 1 except that 3-(imidazol-1-yl)-propanol prepared in Preparation 8 was used instead of 3-(1-triphenylmethyl-imidazol-4-yl)-propanol in Example 1-1) and that 3-chlorobenzyl bromide was used instead of ethyl bromoacetate in Example 1-2).

$^1$H NMR(CDCl$_3$) δ(ppm) 1.86(3H, s), 2.27(2H, m), 3.77 (2H, t), 4.02(1H, d), 4.10(2H, t), 4.35(1H, d), 6.76(2H, m), 6.90(1H, t), 6.97(1H, d), 7.06(1H, s), 7.11(1H, s), 7.21(1H, d), 7.32(1H, t), 7.42(1H, t), 7.50(1H, t), 7.63(1H, d), 7.68 (1H, s), 7.82(1H, d), 7.88(1H, d)

FAB Mass(M+H): 473

EXAMPLE 20

Synthesis of 1-(3-bromo-benzyl)-3-(3-imidazol-1-yl-propyl)-5-methyl-5-naphthalen-1-yl-imidazolidin-2,4-dione(Compound 20)

The title compound was prepared in a yield of 90% according to the same procedure as Example 1 except that 3-(imidazol-1-yl)-propanol prepared in Preparation 8 was used instead of 3-(1-triphenylmethyl-imidazol-4-yl)-propanol in Example 1-1) and that 3-bromo-benzyl bromide was used instead of ethyl bromoacetate in Example 1-2).

$^1$H NMR(CDCl$_3$) δ(ppm) 1.86(3H, s), 2.27(2H, m), 3.77 (2H, t), 4.07–4.20(3H, m), 4.31(1H, d), 6.78–6.85(2H, m) 6.87(1H, s), 7.03(1H, s), 7.09(2H, m), 7.21(1H, d), 7.32(1H, m), 7.42(1H, t), 7.48(1H, t), 7.57(1H, s), 7.63(1H, d), 7.82(1H, d), 7.87(1H, d)

FAB Mass(M+H): 517

EXAMPLE 21

Synthesis of 1-(4-bromo-benzyl)-3-(3-imidazol-1-yl-propyl)-5-methyl-5-naphthalen-1-yl-imidazolidin-2,4-dione(Compound 21)

The title compound was prepared in a yield of 95% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 4-bromo-benzyl bromide was used instead of ethyl bromoacetate in Example 1-2).

$^1$H NMR(CDCl$_3$) δ(ppm) 1.86(3H, s), 2.27(2H, m), 3.77 (2H, t), 3.97(1H, d), 4.09(2H, t), 4.31 (1H, d), 6.72(2H, d), 7.05(1H, s), 7.10(3H, m), 7.23(1H, d), 7.32(1H, t), 7.41–7.55(2H, m), 7.57–7.68(2H, m), 7.86(1H, d), 7.89(1H, d)

FAB Mass(M+H): 517

EXAMPLE 22

Synthesis of 1-(3-trifluoromethyl-benzyl)-3-(3-imidazol-1-yl-propyl)-5-methyl-5-naphthalen-1-yl-imidazolidin-2,4-dione(Compound 22)

The title compound was prepared in a yield of 92% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 3-trifluoromethyl-benzyl bromide was used instead of ethyl bromoacetate in Example 1-2).

$^1$H NMR(CDCl$_3$) δ(ppm) 1.86(3H, s), 2.30(2H, m), 3.80 (2H, m), 4.10(2H, t), 4.30(2H, s), 6.94(1H, s), 7.00–7.15 (4H, m), 7.20(1H, t), 7.29(1H, t), 7.40(1H, t), 7.48(1H, t), 7.62(1H, d), 7.72(1H, s), 7.78(1H, d), 7.85(1H, d)

FAB Mass(M+H): 507

EXAMPLE 23

Synthesis of 1-(3-trifluoromethoxy-benzyl)-3-(3-imidazol-1-yl-propyl)-5-methyl-5-naphthalen-1-yl-imidazolidin-2,4-dione(Compound 23)

The title compound was prepared in a yield of 80% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 3-trifluoromethoxy-benzyl bromide was used instead of ethyl bromoacetate in Example 1-2).

$^1$H NMR(CDCl$_3$) δ(ppm) 1.80(3H, s), 2.30(2H, m), 3.80 (2H, m), 4.00(1H, d), 4.10(2H, t), 4.44(1H, d), 6.72(1H, s), 6.79(1H, s), 6.89(1H, d), 7.00(1H, t), 7.06(1H, s), 7.10(1H, s), 7.22(1H, d), 7.33(1H, t), 7.43(1H, t), 7.49(1H, t), 7.62 (1H, d) 7.67(1H, s), 7.83(1H, d), 7.88(1H, d)

FAB Mass(M+H): 523

EXAMPLE 24

Synthesis of 3-(3-imidazol-1-yl-propyl)-5-methyl-5-naphthalen-1-yl-1-(4-phenoxy-benzyl)-imidazolidin-2,4-dione(Compound 24)

The title compound was prepared in a yield of 70% according to the same procedure as Example 1-1) to 1–2) except that 3-(imidazol-1-yl)-propanol prepared in Preparation 8 was used instead of 3-(1-triphenylmethyl-imidazol-4-yl)-propanol in Example 1-1) and that 4-phenoxy-benzyl bromide was used instead of ethyl bromoacetate in Example 1-2).

$^1$H NMR(CDCl$_3$) δ(ppm) 1.86(3H, s), 2.27(2H, m), 3.73–3.85(3H, m), 4.09(2H, t), 4.57(1H, d), 6.61(1H, s), 6.73(2H, t), 6.88(2H, d), 7.04(2H, m), 7.10(2H, m), 7.25–7.40(4H, m), 7.43–7.50(2H, m), 7.56–7.63(2H, m), 7.89(2H, t)

FAB Mass(M+H): 531

EXAMPLE 25

Synthesis of 3-(3-imidazol-1-yl-propyl)-5-methyl-5-naphthalen-1-yl-1-(3-phenoxy-benzyl)-imidazolidin-2,4-dione(Compound 25)

The title compound was prepared in a yield of 73% according to the same procedure as Example 1-1) to 1-2) except that (imidazol-1-yl)-propanol prepared in Preparation 8 was used instead of 3-(1-triphenylmethyl-imidazol-4-yl)-propanol in Example 1-1) and that 3)-phenoxy-benzyl bromide was used instead of ethyl bromoacetate in Example 1-2).

$^1$H NMR(CDCl$_3$) δ(ppm) 1.86(3H, s), 2.27(2H, m), 3.73–3.85(3H, m), 4.09(2H, t), 4.57(1H, d), 6.60(1H, s), 6.72(2H, t), 6.88(2H, d), 7.00–7.12(4H, m), 7.25–7.40(4H, m), 7.43–7.50(2H, m), 7.57(1H, s), 7.60(1H, d), 7.89(2H, t)

FAB Mass(M+H): 531

EXAMPLE 26

Synthesis of 3-(3-imidazol-1-yl-propyl)-1-(4-methylsulfanyl-benzyl)-5-methyl-5-naphthalen-1-yl-imidazolidin-2,4-dione(Compound 26)

The title compound was prepared in a yield of 85% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 4-methylsulfanyl-benzyl bromide was used instead of ethyl bromoacetate in Example 1-2).

$^1$H NMR(CDCl$_3$) δ(ppm) 1.86(3H, s), 2.27(2H, m), 3.73–3.85(3H, m), 4.09(2H, t), 4.57(1H, d), 6.88(2H, d), 6.99(2H, d), 7.04(1H, s), 7.08(1H, s), 7.29(1H, d), 7.34(1H, t), 7.45(1H, t), 7.51(1H, t), 7.58(1H, s), 7.62(1H, d), 7.86 (1H, d), 7.90(1H, d)

FAB Mass(M+H): 485

EXAMPLE 27

Synthesis of 3-(3-imidazol-1-yl-propyl)-1-(4-methylsulfanylmethyl-benzyl)-5-methyl-5-naphthalen-1-yl-imidazolidin-2,4-dione(Compound 27)

The title compound was prepared in a yield of 65% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 4-methylsulfanylmethyl-benzyl bromide was used instead of ethyl bromoacetate in Example 1-2).

$^1$H NMR(CDCl$_3$) δ(ppm) 1.86(3H, s), 2.27(2H, m), 3.55 (2H, s), 3.7–3.85(3H, m), 4.09(2H, t), 4.57(1H, d), 6.88(2H, d), 6.99(2H, d), 7.04(1H, s), 7.08(1H, s), 7.29(1H, d), 7.45(1H, t), 7.45(1H, t), 7.51(1H, t), 7.58(1H, s), 7.62(1H, d), 7.86(1H, d), 7.90(1H, d)

FAB Mass(M+H): 499

EXAMPLE 28

Synthesis of 3-(3-imidazol-1-yl-propyl)-1-(4-methylsulfonyl-benzyl)-5-methyl-5-naphthalen-1-yl-imidazolidin-2,4-dione(Compound 28)

The title compound was prepared in a yield of 70% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 4-methylsulfonyl-benzyl bromide was used instead of ethyl bromoacetate in Example 1-2).

$^1$NMR(CDCl$_3$) δ(ppm) 1.86(3H, s), 2.27(2H, m), 2.87 (3H, s), 3.80(2H t) 4.09(2H, t), 4.25(1H, d), 4.40(1H, d), 6.95(2H, d), 7.04(1H, s), 7.08(1H, s), 7.18(1H, d), 7.28(1H, t), 7.37–7.45(4H, m), 7.59(1H, s), 7.64(1H, d), 7.77(1H, d), 7.83(1H, d)

FAB Mass(M+H): 517

EXAMPLE 29

Synthesis of 5-[3-(3-imidazol-1-yl-propyl)-5-methyl-5-naphthalen-1-yl-2,4-dioxo-imidazolidin-1-ylmethyl]-2-methylsulfanyl-benzonitrile(Compound 29)

The title compound was prepared in a yield of 50% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 5-bromomethyl-2-methylsulfanyl-benzonitrile was used instead of ethyl bromoacetate in Example 1-2).

$^1$H NMR(CDCl$_3$) δ(ppm) 1.86(3H, s), 2.27(2H, m), 2.40 (1H, s), 3.80(2H, t), 4.00(1H, d), 4.09(2H, t), 4.48(1H, d), 6.66(1H, d), 6.69(1H, d), 6.95(1H, dd), 7.04(1H, s), 7.05–7.12(2H, m), 7.45(1H, d), 7.40(1H, t), 7.49(1H, t), 7.59(1H, s), 7.64(1H, d), 7.78(1H, d), 7.87(1H, d)

FAB Mass(M+H): 510

EXAMPLE 30

Synthesis of 5-[3-(3-imidazol-1-yl-propyl)-5-methyl-5-naphthalen-1-yl-2,4-dioxo-imidazolidin-1-ylmethyl]-2-methylsulfonyl-benzonitrile(Compound 30)

The title compound was prepared in a yield of 72% according to the same procedure as Example 1-1) to 1-2) except that 3)-(imidazol-1-yl)-propanol prepared in Preparation 8 was used instead of 3(1-triphenylmethyl-imidazol-4-yl)-propanol in Example 1-1) and that 5bromomethyl-2-methylsulfonyl-benzonitrile was used instead of ethyl bromoacetate in Example 1-2).

$^1$H NMR(CDCl$_3$) δ(ppm) 2.10(3H, s), 2.32(2H, m), 3.08 (3H, s), 3.83(2H, m), 3.95(1H, d), 4.15(2H, t), 4.85(1H, d), 6.92(1H, s), 7.04–7.06(2H, m), 7.10–7.14(2H, m), 7.28(1H, d), 7.41(1H, t), 7.49(1H, d), 7.52(1H, d), 7.61(1H, s), 7.69(1H, d), 7.77(1H, d), 7.86(1H, d)

FAB Mass(M+H): 542

EXAMPLE 31

Synthesis of 2-[3-(3-imidazol-1-yl-propyl)-5-methyl-5-naphthalen-1-yl-2,4-dioxo-imidazolidin-1-ylmethyl]-benzonitrile(Compound 31)

The title compound was prepared in a yield of 90% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 2-bromomethyl-benzonitrile was used instead of ethyl bromoacetate in Example 1-2).

$^1$H NMR(CDCl$_3$) δ(ppm) 1.86(3H, s), 2.30(2H, m), 3.80 (2H, m), 4.09(2H, t), 4.43(1H, d), 4.73(1H, d), 6.89(1H, m), 6.95(1H, m), 7.03–7.10(4H, m), 7.22(1H, d), 7.30(1H, m), 7.36(1H, m), 7.43(11H, t), 7.59(1H, s), 7.67(1H, d), 7.70 (2H, d)

FAB Mass(M+H): 464

EXAMPLE 32

Synthesis of 3-[3-(3-imidazol-1-yl-propyl)-5-methyl-5naphthalen-1-yl-2,4-dioxo-imidazolidin-1-ylmethyl]-benzonitrile(Compound 32)

The title compound was prepared in a yield of 80% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 3-bromomethyl-benzonitrile was used instead of ethyl bromoacetate in Example 1-2).

$^1$H NMR(CDCl$_3$) δ(ppm) 1.86(3H, s), 2.30(2H, m), 3.80 (2H, t), 4.05–4.20(3H, m), 4.42(1H, d), 6.84(1H, s), 6.97 (1H, t), 7.04(1H, s), 7.06–7.19(4H, m), 7.29(1H, m), 7.41 (1H, t), 7.51(1H, t), 7.59(1H, s), 7.67(1H, d), 7.80(1H, d), 7.89(1H, d)

FAB Mass(M+H): 464

EXAMPLE 33

Synthesis of 4-[3-(3-imidazol-1-yl-propyl)-5-methyl-5-naphthalen-1-yl-2,4-dioxo-imidazolidin-1-ylmethyl]-benzonitrile(Compound 33)

The title compound was prepared in a yield of 77% according to the same procedure as Example 1-1) to 1-2) except that 3-(imidazol-1-yl)-propanol prepared in Preparation 8 was used instead of 3-(1-triphenylmethyl-imidazol-4-yl)-propanol in Example 1-1) and that 4-bromomethyl-benzonitrile was used instead of ethyl bromoacetate in Example 1-2).

$^1$H NMR(CDCl$_3$) δ(ppm) 2.10(3H, s), 2.32(2H, m), 3.08 (3H, s), 3.83(2H, m), 3.95(1H, d), 4.15(2H, t), 4.85(1H, d), 6.92(1H, s), 7.02–7.06(2H, m), 7.10–7.14(2H, m), 7.28(1H, t), 7.41(1H, t), 7.49(1H, d), 7.52(1H, d), 7.61(1H, s), 7.69 (1H, d), 7.77(1H, d), 7.86(1H, d)

FAB Mass(M+H): 542

EXAMPLE 34

Synthesis of 1-(4-aminomethyl-benzyl)-3-(3-imidazol-1-yl-propyl)-5-methyl-5-naphthalen-1-yl-imidazolidin-2,4-dione(Compound 34)

The title compound was prepared in a yield of 80% according to the same procedure as Example 1 except that 3-(imidazol-1-yl)-propanol prepared in Preparation 8 was used instead of 3-(1-triphenylmethyl -imidazol-4-yl)-propanol in Example 1-1) and that 4-[N-(t-butyloxycarbonyl)-aminomethyl]-benzyl bromide was used instead of ethyl bromoacetate in Example 1-2).

$^1$H NMR(CDCl$_3$) δ(ppm) 1.88(3H, s), 2.29(2H, m), 2.80 (3H, s), 3.58(2H, s), 3.79(2H, m), 3.91(1H, d), 4.09(2H, t), 4.44(1H, d), 6.86(2H, d), 6.98(2H, s), 7.06(2H, m), 7.25(1H, t), 7.33(1H, t), 7.44(1H, t), 7.48(1H, t), 7.57(1H, s), 7.60(1H, d), 7.83(1H, d), 7.88(1H, d)

FAB Mass(M+H): 468

EXAMPLE 35

Synthesis of N-{2-[3-(3-imidazol-1-yl-propyl)-5-methyl-5-naphthalen-1-yl-2,4-dioxo-imidazolidin-1-ylmethyl]-benzyl}-methanesulfonamide(Compound 35)

35-1) Synthesis of 1-(2-aminomethyl-benzyl)-3-(3-imidazol-1-yl-propyl)-5-methyl-5-naphthalen-1-yl-imidazolidin-2,4-dione The title compound was prepared in a yield of 83% according to the same procedure as Example 34 except that 2-[N-(t-butyloxycarbonyl)-aminomethyl]-benzylbromide was used instead of 4-[N-(t-butyloxycarbonyl)-aminomethyl]-benzylbromide.

35-2) Synthesis of N-[2-{3-(3-imidazol-1-yl-propyl)-5-methyl-5-naphthalen-1-yl-2,4-dioxo-imidazolidin-1-ylmethyl}-benzyl]-methanesulfonamide 0.02 ml (0.24 mmol) of methansulfonyl chloride was added to 10 ml dichloromethane solution of 0.06 ml (0.4 mmol) of triethylamine and 0.10 g (0.2 mmol) of 1-(2-aminomethyl-benzyl)-3-(3-imidazol-1-yl-propyl)-5-methyl-5-naphthalen-1-yl-imidazolidin-2,4-dione prepared in Example 35-1) at 0° C. After stirring for 1 hour at room temperature, it was washed with saturated potassium carbonate solution and saturated sodium chloride solution sequentially. After removal of dichloromethane, chromatography using a solvent mixture of methanol-dichloromethane (7:93) as the eluent was carried out to obtain 0.1 g (0.18 mmol, Yield: 87%) of the title compound.

$^1$H NMR(CDCl$_3$) δ(ppm) 1.76(3H, s), 2.29(2H, m), 2.78 (3H, s), 3.79(2H, t), 4.04(1H, d), 4.10(2H, t), 4.16(2H, s), 4.67(1H, d), 6.55(1H, d), 6.95(1H, t), 7.04–7.18(4H, m), 7.25(1H, m), 7.40(1H, t), 7.44–7.55(2H, m), 7.60(2H, m), 7.85(1H, d), 7.90(1H, d)

FAB Mass(M+H): 546

EXAMPLE 36

Synthesis of N-{3-[3-(3-imidazol-1-yl-propyl)-5-methyl-5-naphthalen-1-yl-2,4-dioxo-imidazolidin-1-ylmethyl]-benzyl}-methanesulfonamide(Compound 36)

The title compound was prepared in a yield of 78% according to the same procedure as Example 35 except that 3-[N-(t-butyloxycarbonyl)-aminomethyl]-benzylbromide was used instead of 4-[N-(t-butyloxycarbonyl)-aminomethyl]-benzylbromide.

$^1$H NMR(CDCl$_3$) δ(ppm) 1.63(3H, s), 2.23–2.43(2H, m), 2.85(3H, s), 3.85–3.93(3H, m), 4.02–4.21(4H, m), 4.50(1H, d), 6.78(1H, d), 6.99(2H, d), 7.06(3H, m), 7.18(1H, m), 7.37(1H, m), 7.46(1H, t), 7.50(1H, t), 7.58(1H, d), 7.63(1H, s), 7.87(1H, d), 7.89(1H, d)

FAB Mass(M+H): 546

EXAMPLE 37

Synthesis of N-{4-[3-(3-imidazol-1-yl-propyl)-5-methyl-5-naphthalen-1-yl-2,4-dioxo-imidazolidin-1-ylmethyl]-benzyl}-methanesulfonamide(Compound 37)

The title compound was prepared in a yield of 83% according to the same procedure as Example 35-2) except that 1-(4-aminomethyl-benzyl)-3-(3-imidazol-1-yl-propyl)-5-methyl-5-naphthalen-1 -yl-imidazolidin-2,4-dione prepared in Example 34 was used instead of 1-(2-aminomethyl-benzyl)-3-(3-imidazol-1-yl-propyl)-5-methyl-5-naphthalen-1-yl-imidazolidin-2,4-dione.

$^1$H NMR(CDCl$_3$) δ(ppm) 1.88(3H, s), 2.29(2H, m), 2.80 (3H, s), 3.79(2H, m), 3.91(1H, d), 4.05–4.15(4H, m), 4.44 (1H, d), 6.86(2H, d), 6.98(2H, s), 7.06(2H, m), 7.25(1H, t), 7.33(1H, t), 7.44(1H, t), 7.48(1H, t), 7.57(1H, s), 7.60(1H, d), 7.83(1H, d), 7.88(1H, d)

FAB Mass(M+H): 546

EXAMPLE 38

Synthesis of 4-[3-(3-imidazol-1-yl-propyl)-5-methyl-5-naphthalen-1-yl-2,4-dioxo-imidazolidin-1-ylmethyl]-benzoic acid methyl ester(Compound 38)

The title compound was prepared in a yield of 71% according to the same procedure as Example 1-1) to 1-2)

except that 3-(imidazol-1-yl)-propanol prepared in Preparation 8 was used instead of 3-(1-triphenylmethyl-imidazol-4-yl)-propanol in Example 1-1) and that 4-bromomethyl-benzoic acid methyl ester was used instead of ethyl bromoacetate in Example 1-2).

$^1$H NMR(CDCl$_3$) δ(ppm) 1.80(3H, s), 2.28(2H, m), 2.72 (2H, m), 3.79(3H, s), 3.95(1H, d), 4.08(2H, m), 4.48(1H, d), 6.94(2H, d), 7.03(1H, s), 7.10(1H, m), 7.25(1H, d), 7.35(1H, t), 7.45(2H, m), 7.60(1H, d), 7.65(1H, s), 7.68(2H, d), 7.82(1H, d), 7.88(1H, d)

FAB Mass(M+H): 497

EXAMPLE 39

Synthesis of 4-[3-(3-imidazol-1-yl-propyl)-5-methyl-5-naphthalen-1-yl-2,4-dioxo-imidazolidin-1-ylmethyl]-benzoic acid(Compound 39)

The title compound was prepared in a yield of 93% according to the same procedure as Example 2 using 4-[3-(3-imidazol-1-yl-propyl)-5-methyl-5-naphthalen-1-yl-2,4-dioxo-imidazolidin-1-ylmethyl]-benzoic acid methyl ester prepared in Example 38.

$^1$H NMR(CDCl$_3$) δ(ppm) 483

EXAMPLE 40

Synthesis of 3-(3-imidazol-1-yl-propyl)-1-[3-(morpholine-4-carbonyl)benzyl]-5-methyl-naphthalen-1-yl-imidazolidin-2,4-dione(Compound 40)

The title compound was prepared in a yield of 90% from compound 38 according to the same procedure as Example 1-3) except that morpholine was used instead of methionine methyl ester.

$^1$H NMR(CDCl$_3$) δ(ppm) 1.89(3H, s), 2.38(2H, m), 3.20–3.88(10H, br), 4.13(1H, d), 4.45(1H, d), 6.92(2H, d), 7.30(2H, d), 7.33(1H, d), 7.35(3H, m), 7.41(1H, t), 7.50(1H, t), 7.65(1H, d), 7.82(1H, d), 7.88(1H, d), 9.30(1H, s)

FAB Mass(M+H): 552

EXAMPLE 41

Synthesis of 4-[3-(3-imidazol-1-yl-propyl)-5-methyl-5-naphthalen-1-yl-2,4-dioxo-imidazolidin-1-ylmethyl]-N-(2-methoxy-ethyl)-benzamide (Compound 41)

The title compound was prepared in a yield of 80% from compound 38 according to the same procedure as Example 1-3) except that 2-methoxyethylamine was used instead of methionine methyl ester.

$^1$H NMR(CDCl$_3$) δ(ppm) 1.85(3H, s), 2.35(2H, m), 3.40 (3H, s), 3.61(4H, m), 3.80(2H, m), 4.01(1H, d), 4.35(2H, m), 4.52(1H, d), 6.40(1H, s), 6.93(2H, d), 7.21(1H, d), 7.30–7.53(7H, m), 7.62(1H, d), 7.84(1H, d), 7.89(1H, d), 8.92(1H, s)

FAB Mass(M+H): 540

EXAMPLE 42

Synthesis of 4[3-(3-imidazol-1-yl-propyl)-5-methyl-5-naphthalen-1-yl-2,4-dioxo-imidazolidin-1-ylmethyl]-N-(2-methoxy-ethyl)-N-methyl-benzamide (Compound 42)

The title compound was prepared in a yield of 90% from compound 39 according to the same procedure as Example 1-3) except that 2-methoxy-ethylmethylamine was used instead of methionine methyl ester.

$^1$H NMR(CDCl$_3$) δ(ppm) 1.80(3H, s), 2.35(2H, m), 2.85 (2H, s), 3.05(1H, s), 3.35(5H, m), 3.55–4.05(5H, m), 4.28 (2H, m), 4.50(1H, m), 6.93(4H, d), 7.10(2H, m), 7.28(3H, m), 7.36(1H, t), 7.45(1H, m), 7.51(1H, t), 7.63(1H, d), 7.89(2H, m), 8.75(1H, s)

FAB Mass(M+H): 554

EXAMPLE 43

Synthesis of 4-{4-[3-(3-imidazol-1-yl-propyl)-5-methyl-5-naphthalen-1-yl-2,4-dioxo-imidazolidin-1-ylmethyl]-benzoyl}-piperazine-1-carboxylic acid benzyl ester(Compound 43)

The title compound was prepared in a yield of 70% from compound 38 according to the same procedure as Example 1-3) except that piperazine 1-carboxylic acid benzyl ester was used instead of methionine methyl ester.

$^1$H NMR(CDCl$_3$) δ(ppm) 1.89(3H, s), 2.35(2H, m), 3.10–3.75(8H, br), 3.80(2H, m), 4.19(3H, m), 4.40(1H, d), 5.17(2H, s), 6.92(2H, d), 7.01(2H, d), 7.18(2H, d), 7.24(1H, d), 7.28–7.44(7H, m), 7.49(1H, t), 7.63(1H, d), 7.82(1H, d), 7.89(1H, d), 8.20(1H, s)

FAB Mass(M+H): 685

EXAMPLE 44

Synthesis of 3-(3-imidazol-1-yl-propyl)-1-[3-(thiomorpholine-4-carbonyl)-benzyl]-5-methyl-5-naphthalen-1-yl-imidazolidin-2,4-dione(Compound 44)

The title compound was prepared in a yield of 86% from 3-[3-(3-imidazol-1-yl-propyl)-5-methyl-5-naphthalen-1-yl-2,4-dioxo-imidazolidin-1-ylmethyl]-benzoic acid methyl ester according to the same procedure as Example 1-3) except that thiomorpholine was used instead of methionine methyl ester.

$^1$H NMR(CDCl$_3$) δ(ppm) 1.82(3H, s), 2.35(2H, m), 2.55 (4H, br), 3.45(2H, br), 3.80(5H, m), 4.26(2H, m), 4.54(1H, d), 7.00(2H, m), 7.09(2H, d), 7.25(3H, m), 7.63(1H, d), 7.89(2H, t), 8.51(1H, s)

FAB Mass(M+H): 568

EXAMPLE 45

Synthesis of 4-{5-[3-(4-methyl-4-naphthalen-1-yl-2,5-dioxo-imidazolidin-1-yl)-propyl]-imidazol-1-ylmethyl}benzonitrile(Compound 45)

The title compound was prepared in a yield of 60% according to the same procedure as Example 1-1) except that 4-[5-(3-hydroxy-propyl)-imidazol-1-ylmethyl]-benzonitrile was used instead of 3-(1-triphenylmethyl-imidazol-4-yl)-propanol.

$^1$H NMR(CDCl$_3$) δ(ppm) 1.95(2H, m), 1.98(3H, s), 2.36 (2H, t), 3.63(2H, t), 5.00(2H, s), 6.87(1H, s), 6.94(2H, d), 7.39(2H, t), 7.45(3H, m), 7.53(1H, s), 7.63(1H, d), 7.83(1H, d), 7.88(1H, d), 7.90(1H, d)

FAB Mass(M+H): 464

EXAMPLE 46

Synthesis of 4-{5-[3-(3-methyl-4-methyl-4-naphthalen-1-yl-2,5-dioxo-imidazolidin-1-yl)-propyl]-imidazol-1-ylmethyl}-benzonitrile (Compound 46)

The title compound was prepared in a yield of 75% according to the same procedure as Example 1-1) to 1-2)

except that 4-[5-(3-hydroxy-propyl)-imidazol-1-ylmethyl]-benzonitrile was used instead of 3-(1-triphenylmethyl-imidazol-4-yl)-propanol in Example 1-1) and that methyl iodide was used instead of ethyl bromoacetate in Example 1-2).

$^1$H NMR(CDCl$_3$) δ(ppm) 1.95(3H, s), 2.05(2H, t), 2.47 (2H, t), 2.62(3H, s), 3.74(2H, m), 5.16(2H, dd), 7.03(1H, s), 7.06(2H, d), 7.23(1H, t), 7.35(1H, d), 7.43(1H, t), 7.47(1H, d), 7.52(1H, t), 7.66(1H, d), 7.90(2H, m), 8.24(1H, s)

FAB Mass(M+H): 478

EXAMPLE 47

Synthesis of 4-{5-[3-(3-ethyl-4-methyl-4-naphthalen-1-yl-2,5-dioxo-imidazolidin-1-yl)-propyl]-imidazol-1-ylmethyl}benzonitrile
(Compound 47)

The title compound was prepared in a yield of 78% according to the same procedure as Example 46 except that ethyl iodide was used instead of methyl iodide.

$^1$H NMR(CDCl$_3$) δ(ppm) 0.83(3H, t), 1.95(3H, s), 2.07 (2H, t), 2.51(2H, t), 3.11(2H, m), 3.76(2H, m), 5.28(2H, dd), 7.13(3H, d), 7.20(1H, t), 7.32(1H, d), 7.42(1H, t), 7.47(2H, d), 7.53(1H, t), 7.70(1H, d), 7.90(1H, d), 7.92(1H, d), 9.04(1H, s)

FAB Mass(M+H): 492

EXAMPLE 48

Synthesis of 4-{5-[3-(3-propyl-4-methyl-4-naphthalen-1-yl-2,5-dioxo-imidazolidin-1-yl)-propyl]-imidazol-1-ylmethyl}benzonitrile
(Compound 48)

The title compound was prepared in a yield of 62% according to the same procedure as Example 46 except that propyl iodide was used instead of methyl iodide.

$^1$H NMR(CDCl$_3$) δ(ppm) 0.61(3H, t), 1.25(2H, m), 1.93 (3H, s), 2.07(2H, t), 2.47(2H, t), 2.96(2H, m), 3.73(2H, m), 5.13(2H, dd), 7.00(1H, s), 7.04(2H, d), 7.22(1H, t), 7.32(1H, d), 7.41(1H, t), 7.68(1H, d), 7.90(2H, m), 7.99(1H, s)

FAB Mass(M+H): 506

EXAMPLE 49

Synthesis of 4-{5-[3-(3-butyl-4-methyl-4-naphthalen-1-yl-2,5-dioxo-imidazolidin-1-yl)-propyl]-imidazol-1-ylmethyl}benzonitrile
(Compound 49)

The title compound was prepared in a yield of 61% according to the same procedure as Example 46 except that butyl iodide was used instead of methyl iodide.

$^1$H NMR(CDCl$_3$) δ(ppm) 0.61(3H, t), 1.03(2H, m), 1.24 (2H, m), 1.93(3H, s), 2.07(2H, m), 2.47(2H, t), 2.99(2H, m), 3.72(2H, m), 5.09(2H, dd), 7.00(1H, s), 7.03(2H, d), 7.22 (1H, t), 7.32(1H, d), 7.42(1H, t), 7.48–7.53(3H, m), 7.68 (1H, d), 7.83(1H, s), 7.88(1H, d), 7.91(1H, d)

FAB Mass(M+H): 520

EXAMPLE 50

Synthesis of 4-(5-{3-[3-(2-methoxy-ethoxymethyl)-4-methyl-4-naphthalen-1-yl-2,5-dioxo-imidazolidin-1-yl]-propyl}-imidazol-1-ylmethyl)-benzonitrile
(Compound 50)

The title compound was prepared in a yield of 55% according to the same procedure as Example 46 except that 2-methoxy-ethoxymethyl bromide was used instead of methyl iodide.

$^1$H NMR(CDCl$_3$) δ(ppm) 2.15(3H, s), 2.31(2H, m), 3.30 (4H, br), 3.41(1H, br), 3.56(1H, br), 3.70(1H, br), 3.76(2H, t), 4.16(3H, m), 4.98(1H, d), 7.09(1H, s), 7.13(1H, s), 7.28(1H, m), 7.40(1H, t), 7.45–7.60(2H, m), 7.80(1H, d), 7.85–8.0(3H, m)

FAB Mass(M+H): 437

EXAMPLE 51

Synthesis of (3-{3-[3-(4-cyanobenzyl)-3H-imidazol-4-yl]-propyl}-5-methyl-5-naphthalen-1-yl-2,4-dioxo-imidazolidin-1-yl)-acetic acid ethyl ester
(Compound 51)

The title compound was prepared in a yield of 88% according to the same procedure as Example 1-1) to 1-2) except that 4-[5-(3-hydroxy-propyl)-imidazol-1-ylmethyl]-benzonitrile was used instead of 3-(1-triphenylmethyl-imidazol-4-yl)-propanol in Example 1-1).

1H NMR(CDCl$_3$) δ(ppm) 1.88(3H, s), 2.12(2H, m), 2.54 (2H, m), 3.80(2H, m), 4.10(1H, d), 4.39(1H d), 5.20(2H, s), 6.88(1H, s), 6.96(1H, t), 7.03–7.22(7H, m), 7.36(1H, t), 7.48–7.57(3H, m), 7.66(1H, d), 7.80(1H, d), 7.89(1H, d), 8.11(1H, br)

FAB Mass(M+H): 579

EXAMPLE 52

Synthesis of (3-{3-[3-(4-cyanobenzyl)-3H-imidazol-4-yl]-propyl}-5-methyl-5-naphthalen-1-yl-2,4-dioxo-imidazolidin-1-yl)-acetic acid lithium salt
(Compound 52)

The title compound was prepared in a yield of 81% according to the same procedure as Example 1-1) to 1-2) and Example 2 except that 4-[5-(3-hydroxy-propyl)-imidazol-1-ylmethyl]-benzonitrile was used instead of 3-(1-triphenylmethyl-imidazol-4-yl)-propanol in Example 1-1).

FAB Mass(M+H): 522

EXAMPLE 53

Synthesis of 4-(5-{3-[3-benzyl-4-methyl-4-naphthalen-1-yl-2,5-dioxo-imidazolidin-1-yl]-propyl}-imidazol-1-ylmethyl)-benzonitrile
(Compound 53)

The title compound was prepared in a yield of 81% according to the same procedure as Example 1-1) to 1-2) except that 4-[5-(3-hydroxy-propyl)-imidazol-1-ylmethyl]-benzonitrile was used instead of 3-(1-triphenylmethyl-imidazol-4-yl)-propanol in Example 1-1) and that benzyl bromide was used instead of ethyl bromoacetate in Example 1-2).

$^1$H NMR(CDCl$_3$) δ(ppm) 1.68(3H, s), 2.09(2H, t), 2.50 (2H, t), 3.76(3H, m), 4.75(1H, d), 5.23(2H, s), 6.90(2H, d), 7.06–7.22(8H, m), 7.38(1H, t), 7.45(3H, m), 7.59(1H, d), 7.85(1H, d), 7.90(1H, d), 8.46(1H, s)

FAB Mass(M+H): 554

EXAMPLE 54

Synthesis of 4-(5-{3-[3-(3-cyano-benzyl)-4-methyl-4-naphthalen-1-yl-2,5-dioxo-imidazolidin-1-yl]-propyl}-imidazol-1-ylmethyl)-benzonitrile
(Compound 54)

The title compound was prepared in a yield of 89% according to the same procedure as Example 1-1) to 1-2)

except that 4-[5-(3-hydroxy-propyl)-imidazol-1-ylmethyl]-benzonitrile was used instead of 3-(1-triphenylmethyl-imidazol-4-yl)-propanol in Example 1-1) and that 3bromomethyl benzonitrile was used instead of ethyl bromoacetate in Example 1-2).

$^1$H NMR(CDCl$_3$) δ(ppm) 1.88(3H, s), 2.12(2H, t), 2.54 (2H, m), 3.80(2H, m), 4.10(1H, d), 4.39(1H, d), 5.20(2H, s), 6.88(1H, s), 6.96(1H, t), 7.03–7.22(7H, m), 7.36(1H, t), 7.48–7.57(3H, d), 7.66(1H, d), 7.80(1H, d), 7.90(1H, d), 8.11(1H, br)

FAB Mass(M+H): 579

EXAMPLE 55

Synthesis of 4-{5-[3-(3-furan-2-ylmethyl-4-methyl-4-naphthalen-1-yl-2,5-dioxo-imidazolidin-1-yl)-propyl]-imidazol-1-ylmethyl}-benzonitrile (Compound 55)

The title compound was prepared in a yield of 89% according to the same procedure as Example 1-1) to 1-2) except that 4-[5-(3-hydroxy-propyl)-imidazol-1-ylmethyl]-benzonitrile was used instead of 3-(1-triphenylmethyl-imidazol-4-yl)-propanol in Example 1-1) and that 2-bromomethylfuran was used instead of ethyl bromoacetate in Example 1-2)

$^1$H NMR(CDCl$_3$) δ(ppm) 1.78(3H, s), 2.07(2H, m), 2.48 (2H, m), 3.76(3H, m), 4.58(1H, d), 5.16(2H, s), 5.84(1H, d), 6.08(1H, d), 7.03–7.22(6H, m), 7.32–7.52(5H, m), 7.65(1H, d), 7.90(2H, m), 8.23(1H, s)

FAB Mass(M+H): 544

EXAMPLE 56

Synthesis of 4-(5-{3-[3-(furan-2-carbonyl)-4-methyl-4-naphthalen-1-yl-2,5-dioxo-imidazolidin-1-yl]-propyl}-imidazol-1-ylmethyl)-benzonitrile Compound 56)

The title compound was prepared in a yield of 89% according to the same procedure as Example 1-1) to 1-2) except that 4-[5-(3-hydroxy-propyl)-imidazol-1-ylmethyl]-benzonitrile was used instead of 3-(1-triphenylmethyl-imidazol-4-yl)-propanol in Example 1-1) and that 2-furoyl chloride was used instead of ethyl bromoacetate in Example 1-2).

$^1$H NMR(CDCl$_3$) δ(ppm) 1.32(3H, t), 1.89(3H, s), 2.07 (2H, m), 2.51(2H, m), 3.76(2H, m), 4.06(1H, d), 4.26(2H, q), 4.43(1H, d), 5.96(1H, d), 6.73(1H, d), 7.10–7.22(5H, m), 7.38(1H, t), 7.50(3H, m), 7.67(1H, d), 7.84(1H, d), 7.88(1H, d), 8.80(1H s)

FAB Mass(M+H): 616

EXAMPLE 57

Synthesis of 2-[2-(3-{3-[3-(4-cyanobenzyl)-3H-imidazol-4-yl]-propyl}-5-methyl-5-naphthalen-1-yl-2,4-dioxo-imidazolidin-1-yl)acetylamino]-4-methylsulfanyl-butyric acid methyl ester(Compound 57)

The title compound was prepared in a yield of 60% according to the same procedure as Example 1-1) to 1-3) except that 4-[5-(3-hydroxy-propyl)-imidazol-1-ylmethyl]-benzonitrile was used instead of 3-(1-triphenylmethyl-imidazol-4-yl)-propanol in Example 1-1).

FAB Mass(M+H): 667

EXAMPLE 58

Synthesis of 2-[2-(3-{3-[3-(4-cyanobenzyl)-3H-imidazol-4-yl]-propyl}-5-methyl-5-naphthalen-1-yl-2,4-dioxo-imidazolidin-1-yl)-acetylamino]-4-methylsulfanyl-butyric acid lithium salt (Compound 58)

The same procedure as Example 1-1) to 1-3) was carried out except that 4-[5-(3-hydroxy-propyl)-imidazol-1-ylmethyl]-benzonitrile was used instead of 3-(1-triphenylmethyl-imidazol-4-yl)-propanol in Example 1-1), and then the resulting product was treated according to the same procedure as Example 2 to obtain the title compound in a yield of 70%.

FAB Mass(M+H): 652

EXAMPLE 59

Synthesis of 4-[5-(4-methyl-4-naphthalen-1-yl-2,5-dioxo-imidazolidin-1-yl methyl)-imidazol-1-ylmethyl]-benzonitrile(Compound 59)

The title compound was prepared in a yield of 70% according to the same procedure as Example 1-1) except that 4-(5-hydroxymethyl-imidazol-1-ylmethyl)-benzonitrile prepared in Preparation 7 was used instead of 3-(1-triphenylmethyl-imidazol-4-yl)-propanol in Example 1-1).

$^1$H NMR(CDCl$_3$) δ(ppm) 1.93(3H, s), 4.54(2H, dd), 5.33 (2H, dd), 7.00(3H, m), 7.25(2H, m), 7.40–7.55(6H, m), 7.83(2H, m)

FAB Mass(M+H): 434

EXAMPLE 60

Synthesis of 4-[5-(3-methyl-4-methyl-4-naphthalen-1-yl-2,5-dioxo-imidazolidin-1-ylmethyl)-imidazol-1-ylmethyl]-benzonitrile(Compound 60)

The title compound was prepared in a yield of 62% according to the same procedure as Example 1-1) to 1-2) except that 4-(5-hydroxymethyl-imidazol-1-ylmethyl)-benzonitrile was used instead of 3-(1-triphenylmethyl-imidazol-4-yl)-propanol in Example 1-1) and that methyl iodide was used instead of ethyl bromoacetate in Example 1-2).

$^1$H NMR(CDCl$_3$) δ(ppm) 1.92(3H, s), 2.58(3H, s), 4.65 (2H, dd), 5.44(2H, dd), 6.97(1H, d), 7.09(3H, m), 7.39(1H, s), 7.42(1H, d), 7.48(1H, t), 7.56(3H, m), 7.64(1H, d), 7.87(2H, m)

FAB Mass(M+H): 450

EXAMPLE 61

Synthesis of 4-[5-(3-ethyl-4-methyl-4-naphthalen-1-yl-2,5-dioxo-imidazolidin-1-ylmethyl)-imidazol-1-ylmethyl]-benzonitrile(Compound 61)

The title compound was prepared in a yield of 72% according to the same procedure as Example 1-6) to 1-2) except that 4-(5-hydroxymethyl-imidazol-1-ylmethyl)-benzonitrile was used instead of 3-(1-triphenylmethyl-imidazol-4-yl)-propanol in Example 1-1) and that ethyl iodide was used instead of ethyl bromoacetate in Example 1-2).

$^1$H NMR(CDCl$_3$) δ(ppm) 0.76(1H, t), 1.92(3H, s), 3.06 (2H, q), 4.63(2H, dd), 5.46(2H, dd), 6.93(1H, d), 7.09(3H, m), 7.39(2H, d), 7.46(1H, t), 7.54(3H, m), 7.64(1H, d), 7.85(2H, m)

FAB Mass(M+H): 464

EXAMPLE 62

Synthesis of {3-[3-(4-cyano-benzyl)-3H-imidazol-4-ylmethyl]-5-methyl-5-naphthalen-1-yl-2,4-dioxo-imidazolidin-1-yl)-acetic acid ethyl ester (Compound 62)

The title compound was prepared in a yield of 77% according to the same procedure as Example 1-1) to 1-2)

except that 4-(5-hydroxymethyl-imidazol-1-ylmethyl)-benzonitrile was used instead of 3-(1-triphenylmethyl-imidazol-4-yl)-propanol in Example 1-1).

1H NMR(CDCl$_3$) δ(ppm) 1.14(3H, t), 1.62(2H, s), 1.98 (3H, s), 4.04(2H, m), 4.70(2H, dd), 5.46(2H, dd), 6.93(1H, d), 7.07(1H, t), 7.12(2H, d), 7.41(2H, m), 7.48(1H, t), 7.55(1H, s), 7.58(2H, d), 7.65(1H, d), 7.85(1H, d), 7.89(1H, d)

FAB Mass(M+H): 522

EXAMPLE 63

Synthesis of 4-{4-[3-(3-cyanobenzyl)-4-methyl-4-naphthalen-1-yl -2,5 -dioxo-imidazolidin-1-ylmethyl]-imidazol-1-ylmethyl}-benzonitrile (Compound 63)

The title compound was prepared in a yield of 74% according to the same procedure as Example 1-1) to 1-2) except that 4-(5-hydroxymethyl-imidazol-1-ylmethyl)-benzonitrile was used instead of 3-(1-triphenylmethyl-imidazol-4-yl)-propanol in Example 1-1) and that 3-bromomethylbenzonitrile was used instead of ethyl bromoacetate in Example 1-2).

$^1$H NMR(CDCl$_3$) δ(ppm) 1.90(3H, s), 4.25(2H, dd), 4.72 (2H, dd), 5.55(2H, dd), 6.68(1H, d), 6.80(1H, s), 6.90–7.35 (6H, m), 7.40–7.90(8H, m), 8.10(1H, s)

FAB Mass(M+H): 551

EXAMPLE 64

Synthesis of 3-(3-imidazol-1-yl-propyl)-1-(4-methoxy-benzoyl)-5-methyl-5-naphthalen-1-yl-imidazolidin-2,4-dione(Compound 64)

The title compound was prepared in a yield of 80% according to the same procedure as Example 1-1) to 1-2) except that 3-(imidazol-1-yl)-propanol was used instead of 3-(1-triphenylmethyl-imidazol-4-yl)-propanol in Example 1-1) and that 4-methoxy-benzoyl chloride was used instead of ethyl bromoacetate in Example 1-2).

$^1$H NMR(CDCl$_3$) δ(ppm) 2.30(2H, m), 2.48(3H, s), 3.71–3.90(5H, m), 4.13(2H, t), 6.81(2H, d), 7.03(1H, s), 7.12(1H, s), 7.44–7.57(5H, m), 7.63(1H, d), 7.79(1H, s), 7.88(2H, t), 7.94(1H, d)

FAB Mass(M+H): 483

EXAMPLE 65

Synthesis of 3-(3-imidazol-1-yl-propyl)-5methyl-1-(morpholine-4-carbonyl)-5-naphthalen-1-yl-imidazolidin-2,4-dione(Compound 65)

The title compound was prepared in a yield of 61% according to the same procedure as Example 1-1) to 1-2) except that 3-(imidazol-1-yl)-propanol was used instead of 3-(1-triphenylmethyl-imidazol-4-yl)-propanol in Example 1-1) and that morpholine-4-carbonyl chloride was used instead of ethyl bromoacetate in Example 1-2).

$^1$H NMR(CDCl$_3$) δ(ppm) 2.30(2H, p), 2.44(3H, s), 3.07 (4H, br), 3.26(2H, br), 3.36(2H, br), 3.80(2H, m), 4.15(2H, t), 7.08(1H, s), 7.15(1H, s), 7.31(1H, d), 7.39(1H, t), 7.47 (1H, t), 7.54(1H, t), 7.86(2H, m), 7.94(2H, d)

FAB Mass(M+H): 462

EXAMPLE 66

Synthesis of 3-(3-imidazol-1-yl-propyl)-5-methyl-5-naphthalen-1-yl-2,4-dioxo-imidazolidin-1-carboxylic acid (3-cyano-phenyl)-amide(Compound 66)

The title compound was prepared in a yield of 58% according to the same procedure as Example 1-1) to 1-2) except that 3-(imidazol-1-yl)-propanol was used instead of 3-(1-triphenylmethyl-imidazol-4-yl)-propanol in Example 1-1) and that 3-isocyanatobenzonitrile was used instead of ethyl bromoacetate in Example 1-2).

$^1$H NMR(CDCl$_3$) δ(ppm) 2.35(5H, m), 3.84(2H, br), 4.20(2H, t), 7.10(1H, s), 7.20(1H, s), 7.32(3H, m), 7.40–7.55 (3H, m) 7.60(1H, t), 7.81(1H, s), 7.84–7.98(3H, m), 8.29(1H s), 10.21(1H, s)

FAB Mass(M+H): 493

EXAMPLE 67

Synthesis of N-(4-cyano-tetrahydropyran-4-yl)-2-[3-(3-imidazol-1yl-propyl)-5-methyl-5-naphthalen-1-yl-2,4-dioxo-imidazolidin-1-yl]-acetamide(Compound 67)

The title compound was prepared in a yield of 67% according to the same procedure as Example 1-1) to 1-3) except that 3-(imidazol-1-yl)-propanol was used instead of 3-(1-triphenylmethyl-imidazol-4-yl)-propanol in Example 1-1) and that 4-amino-tetrahydropyran-4-carbonitrile was used instead of methionine methyl ester in Example 1-3).

$^1$H NMR(CDCl$_3$) δ(ppm) 1.57(2H, m), 1.92–2.10(5H, m), 2.30(2H, m), 3.49–3.62(3H, m), 3.67–3.76(4H, m), 4.13(1H, d), 4.21(2H, t), 7.14(1H, s), 7.22(1H, s), 7.36(1H, d), 7.43 (1H, m), 7.46(1H, t), 7.51(1H, t), 7.72(1H, d), 7.90(1H, t), 7.98(1H, br), 8.30(1H, s)

FAB Mass(M+H): 515

EXAMPLE 68

Synthesis of 3-{3-[3-(4-bromo-benzyl)-3H-imidazol-4-yl]-propyl}-5-methyl-5-naphthalen-1-yl-imidazolidin-2,4-dione(Compound 68)

The title compound was prepared in a yield of 78% according to the same procedure as Example 1-1) except that 3-[3-(4-bromo-benzyl)-3H-imidazol-4-yl]-propanol was used instead of 3-(1-triphenylmethyl-imidazol-4-yl)-propanol.

$^1$H NMR(CDCl$_3$) δ(ppm) 1.86(2H, m), 1.93(3H, s), 2.28 (2H, m), 3.54(2H, t), 4.73(2H, s), 6.67(2H, d), 6.70(1H, s), 7.20–7.36(6H, m), 7.56(1H, d), 7.71(1H, d), 7.75(1H, d), 7.90(1H, d), 8.46(1H, s)

FAB Mass(M+H): 517

EXAMPLE 69

Synthesis of 3-{3-[3-(4-bromo-benzyl)-3H-imidazol-4-yl]-propyl}-1,5-di-methyl-5-naphthalen-1-yl-imidazolidin-2,4-dione(Compound 69)

The title compound was prepared in a yield of 70% according to the same procedure as Example 1-1) to 1-2) except that [3-(4-bromo-benzyl)-3H-imidazol4-yl]-propanol was used instead of 3-(1 -triphenylmethyl-imidazol-4-yl)-propanol in Example 1-1) and that methyl iodide was used instead of ethyl bromoacetate in Example 1-2).

$^1$H NMR(CDCl$_3$) δ(ppm) 1.89(3H, s), 2.05(2H, m), 2.47 (2H, m), 2.61(3H, s), 3.73(2H, t), 4.97(2H, m), 6.83(2H, d), 6.95(1H, s). 7.28(1H, d), 7.38(2H, d), 7.43(1H, t), 7.49(1H, t), 7.65(1H, d), 7.70(1H, s), 7.88(2H, t), 8.00(1H, s)

FAB Mass(M+H): 531

EXAMPLE 70

Synthesis of (3-{3-[3-(4-bromo-benzyl)-3H-imidazol-4-yl]-propyl}-5-methyl-5-naphthalen-1-yl-2,4-dioxo-imidazolidin-1-yl)-acetic acid ethyl ester (Compound 70)

The title compound was prepared in a yield of 60% according to the same procedure as Example 1-1) to 1-2)

except that [3-(4-bromo-benzyl)-3H-imidazol-4-yl]-propanol was used instead of 3-(1-triphenylmethyl-imidazol-4-yl)-propanol in Example 1-1).

$^1$H NMR(CDCl$_3$) δ(ppm) 1.24(3H, t), 1.95–2.15(5H, m), 2.51(2H, m), 3.68(2H, t), 4.11(4H, m), 5.23(2H, s), 6.43(1H, s), 6.98(2H, d), 7.38–7.55(5H, m), 7.65(1H, d), 7.86(1H, d), 7.91(2H, m), 9.25(1H, s)

FAB Mass(M+H): 603

EXAMPLE 71

Synthesis of 3-[3-(3-imidazol-1-yl-propyl)-5-methyl-5-phenyl-2,4-dioxo-imidazolidin-1-ylmethyl]-benzonitrile(Compound 71)

The title compound was prepared in a yield of 53% according to the same procedure as Preparation 1 and Example 1-1) to 1-2) except that acetophenone was used instead of acetonaphthone in Preparation 1 and 3-(imidazol-1-yl)-propanol was used instead of 3-(1-triphenylmethyl-imidazol-4-yl)-propanol in Example 1-1) and that 3-bromomethylbenzonitrile was used instead of ethyl bromoacetate in Example 1-2).

$^1$H NMR(CDCl$_3$) δ(ppm) 1.67(3H, s), 2.20(2H, m), 3.67 (2H, t), 4.00(2H, t), 4.05(1H, d), 4.78(1H, d), 6.98(1H, s), 7.06(1H, s), 7.18(2H, m), 7.39(5H, m), 7.46(1H, d), 7.53 (2H, m)

FAB Mass(M+H): 414

EXAMPLE 72

Synthesis of 4-[5-(3-naphthaten-1-yl-2,5-dioxo-imidazolidin-1-ylmethyl)-imidazol-1-ylmethyl]-benzonitrile(Compound 72)

0.053 g(0.24 mmol) of the compound prepared in Preparation 2, 0.051 g(0.24 mmol) of the compound prepared in Preparation 7 and 0.079 g(0.30 mmol) of triphenylphosphine were dissolved in 10 ml of tetrahydrofuran and 0.047 ml(0.30 mmol) of diethylazodicarboxylate was added thereto. The Solution was stirred for 24 hours and tetrahydrofuran was removed under reduced pressure. Column chromatography was performed on the residue using a solvent mixture of methanol and dichloromethanol(3:97) as an eluent to obtain 0.081 g, of the title compound(Yield 80%, MW 421.5).

$^1$H NMR(CDCl$_3$) δ(ppm) 4.31(2H, s), 4.64(2H, s), 5.57 (1H, s), 7.22(2H, d), 7.39(2H, m), 7.47(1H, t), 7.54(2H, m), 7.61(2H, d), 7.66(2H, m), 7.87–7.9(2H, m)

FAB Mass (M+H): 422

EXAMPLE 73

Synthesis of 3-[3-(4-chloro-benzyl)-3H-imidazol-4-ylmethyl]-1-naphthalen-1-yl-imidazolidin-2,4-dione (Compound 73)

73-1) Synthesis of 1-(4-chlorobenzyl)-5-hydroxymethyl-imidazole

The title compound was prepared according to the same procedure as Preparation 6 except that 4-chlorobenzylamine was used instead of 4-bromobenzylamine in 54% yield.

$^1$H NMR(CDCl$_3$) δ(ppm) 2.78(1H, br), 4.49(2H, s), 5.20 (2H, s), 6.93(1H, s), 7.07(2H, d), 7.32(2H, d), 7.45(1H, s)

FAB Mass (M+H): 223

73-2) Synthesis of 3-[3-(4-chloro-benzyl)-3H-imidazol-4-ylmethyl]-1-naphthalen-1-yl-imidazolidin-2,4-dione 0.07 g(Yield 85%, MW 430.9) of the title compound was prepared using 0.046 g(0.21 mmol) of the compound prepared in Example 73-1) and 0.043 g(0.19 mmol) of the compound prepared in Preparation 2 according to the same procedure as Example 72.

$^1$H NMR(CDCl$_3$) δ(ppm) 4.16(2H, s), 4.62(2H, s), 5.31 (2H, s), 7.22(2H, d), 7.39(2H, m), 7.47(1H, t), 7.54(2H, m), 7.61(2H, d), 7.66(2H, m), 7.87–7.93(2H, m)

FAB Mass (M+H): 431

EXAMPLE 74

Synthesis of 4-[5-(3-naphthalen-1-yl-2,5-dioxo-imidazolidin-1-ylmethyl)-imidazol-1-ylmethyl]-piperidine-1-carboxylic acid benzyl ester (Compound 74)

0.07 g(Yield 81%, MW 537.6) of the title compound was prepared using 0.090 g(0.23 mmol) of the compound prepared in Preparation 5 and 0.035 g(0.16 mmol) of the compound prepared in Preparation 2 according to the same procedure as Example 72.

$^1$H NMR(CDCl$_3$) δ(ppm) 1.30(2H, br), 1.62(2H, br), 1.92(1H, m), 2.72(2H, br), 4.05–4.29(4H, br), 4.40(1H, s), 4.80(1H, s), 5.09(1H, s), 7.28–7.38(6H, m), 7.45–7.59(4H, m), 7.72(1H, m), 7.84–7.96(3H, m)

FAB Mass (M+H): 538

EXAMPLE 75

Synthesis of 4-[5-(3-naphthalen-1-ylmethyl-2,5-dioxo-imidazolidin-1-ylmethyl)-imidazol-1-ylmethyl]-benzonitrile(Compound 75)

75-1) Synthesis of (naphthalen-1-ylmethyl-amino)-acetic acid ethyl ester

The title compound was prepared according to the same procedure as Preparation 2–1), except that 1-naphthyl methyl amine was used instead of 1-naphthylamine in 90% yield.

$^1$H NMR(CDCl$_3$) δ(ppm) 1.29(3H, t), 1.98(1H, br), 3.51 (2H, s), 4.22(2H, q), 4.26(2H, s), 7.43(1H, t), 7.46–7.52(2H, m), 7.55(1H, m), 7.78(1H, d), 7.86(1H, d), 8.23(1H, d)

FAB Mass (M+H): 244

75-2) Synthesis of 1-naphthalen-1-ylmethyl)-imidazolidin-2,4-dione

The title compound was prepared using the compound prepared in Example 75-1), according to the same procedure as Preparation 2-2) in 92% yield.

$^1$H NMR(CDCl$_3$) δ(ppm) 3.57(2H, s), 4.91(2H, s), 7.33 (1H, d), 7.38(1H, t), 7.45–7.54(2H, m), 7.79(1H, d), 7.83 (1H, d), 8.05(1H, d)

FAB Mass (M+H): 241

75-3) Synthesis of 4-[5-(3-naphthalen-1-ylmethyl-2,5-dioxo-imidazolidin-1-ylmethyl)-imidazol-1-ylmethyl]-benzonitrile 0.077 g of the title compound was prepared using 0.050 g(0.21 mmol) of the compound prepared in Example 75-2) and 0.047 g(0.22 mmol) of the compound prepared in Preparation 7 according to the same procedure as Example 72(Yield 84%, MW 435).

¹H NMR(CDCl₃) δ(ppm) 3.34(2H, s), 4.51(2H, s), 4.89 (2H, s), 5.41(2H, s), 7.02(2H, d), 7.27(1H, s), 7.32(1H, d), 7.43(3H, m), 7.48(1H, s), 7.54 (2H, m), 7.89(2H, m), 8.05(1H, d)

FAB Mass (M+H): 436

EXAMPLE 76

Synthesis of 4-[5-(3-naphthalen-1-ylmethyl-2,5-dioxo-imidazolidin-1-ylmethyl)-imidazol-1-ylmethyl]-piperidine-1-carboxylic acid benzyl ester (Compound 76)

0.10 g of the title compound was prepared using 0.050 g(0.21 mmol) of the compound prepared in Example 75-2) and 0.072 g(0.22 mmol) of the compound prepared in Preparation 5 according to the same procedure as Example 72(Yield 87%, MW 551).

¹H NMR(CDCl₃) δ(ppm) 1.24(2H, br), 1.75(3H, br), 2.71(2H, s), 3.57(2H, s), 3.99(2H, s), 4.22(1H, br), 4.64(2H, s), 4.99(2H, s), 5.12(2H, s), 7.17 (1H, s), 7.34–7.39(7H, m), 7.44(1H, t), 7.54(2H, m), 7.87(2H, m), 8.07(1H, d)

FAB Mass (M+H): 552

EXAMPLE 77

Synthesis of {1-[3-(4-cyano-benzyl)-3H-imidazol-4-ylmethyl]-3-naphthalen-1-ylmethyl-2,5-dioxo-imidazolidin-4-yl}-acetic acid ethyl ester (Compound 77)

1.58 g(Yield 90%, MW 521) of the title compound was prepared using 1.10 g(3.37 mmol) of the compound prepared in Preparation 3 and 0.86 g(4.06 mmol) of the compound prepared in Preparation 7 according to the same procedure as Example 72.

¹H NMR(CDCl₃) δ(ppm) 1.01(3H, t), 2.61(2H, m), 3.59 (1H, m), 3.67(1H, m), 3.80(1H, m), 4.55(2H, dd), 4.76(1H, d), 5.13(1H, d), 5.42(2H, dd), 7.11 (2H, d), 7.30(1H, s), 7.34(1H, d), 7.41(1H, d), 7.49–7.54(5H, m), 7.87(2H, m), 8.03(1H, m)

FAB Mass (M+H): 552

EXAMPLE 78

Synthesis of {1-[3-(4-cyano-benzyl)-3H-imidazol-4-ylmethyl]-3-naphthalen-1-ylmethyl-2,5-dioxo-imidazolidin-4-yl}-acetic acid(Compound 78)

0.7 g(1.34 mmol) of the compound prepared in Example 77 was dissolved in a solvent mixture of tetrahydrofuran, methanol and water(3:2:1). 0.12 g (2.68 mmol) of lithium hydroxide monohydrate was added thereto and the solution was stirred for 1 hour. The solvents were removed under reduced pressure to obtain 0.66 g of the title compound (Yield 95%, MW 516).

FAB Mass (M+H): 517

EXAMPLE 79

Synthesis of {1-[3-(4-cyano-benzyl)-3H-imidazol-4-ylmethyl]-3-naphthalen-1-ylmethyl-2,5-dioxo-imidazolidin-(4S)-yl}-acetic acid methyl ester (Compound 79)

0.364 g(Yield 78%, MW 507) of the title compound was prepared using 0.287 g(0.920 mmol) of the compound prepared in Preparation 4 and 0.215 g(1.01 mmol) of the compound prepared in Preparation 7 according to the same procedure as Example 72.

¹H NMR(CDCl₃) δ(ppm) 2.46(1H, dd), 2.63(1H, dd), 3.19(3H, s), 3.60(1H, m), 4.52(2H, s), 4.90(2H, dd), 5.40 (2H, dd), 7.09(2H, d), 7.25(1H, s), 7.30 (1H, d), 7.37(1H, t), 7.45–7.49(4H, m), 7.53(1H, s), 7.79–7.85(2H, m), 8.00 (1H, d)

FAB Mass (M+H): 508

EXAMPLE 80

Synthesis of 4-{5-[4-(2-morpholin-4-yl-2-oxo-ethyl)-3-naphthalen-1-ylmethyl-2,5dioxo-imidazolidin-1-ylmethyl]-imidazol-1-ylmethyl}-benzonitrile(Compound 80)

0.073 g(0.14 mmol) of the compound prepared in Example 78, 0.018 ml (0.21 mmol) of morpholine and 0.038 g(0.28 mmol) of N-hydroxybenzotriazole were dissolved in 10 ml of dimethylformamide. 0.04 g (0.21 mmol) of 1-ethyl-3-(3-dimethylaminopropyl)carbodiimide was added thereto. The solution was stirred for 2 hours and dimethylformamide was removed under reduced pressure. 20 ml of ethylacetate was added to the residue and the organic layer was washed with water and saturated sodium bicarbonate solution. Then, ethylacetate was removed under reduced pressure. Column chromatography was performed using a solvent mixture of methanol and dichloromethane(3:97) as an eluent to obtain 0.061 g of the title compound(Yield 78%, MW 562).

¹H NMR(CDCl₃) δ(ppm) 2.36(2H, m), 2.55(1H, m), 2.71(1H, m), 2.86(1H, m), 3.14(1H, m), 3.29(1H, m), 3.88 (1H, t), 4.62(3H, m), 5.25(1H, d), 5.46 (2H, dd), 7.13(2H, d), 7.30(1H, s), 7.32(1H, d), 7.40(1H, t), 7.50–7.57(5H, m), 7.87(2H, m), 8.07 (1H, m)

FAB Mass (M+H): 563

EXAMPLE 81

Synthesis of 4-{(5S)-[4-(2-morpholin-4-yl-2-oxo-ethyl)-3-naphthalen-1-ylmethyl-2,5-dioxo-imidazolidin-1-ylmethyl]-imidazol-1-ylmethyl}-benzonitrile(Compound 81)

The same procedure as Example 78 was carried out using 0.071 g(0.14 mmol) of the compound prepared in Example 79 and the resulting product was treated according to the same procedure as Example 80 to obtain 0.059 g of the title compound(Yield 75%, MW 562).

¹H NMR(CDCl₃) δ(ppm) 2.32(1H, dd), 2.43–2.55(2H, m), 2.70(1H, m), 2.79 (1H, m), 3.16(1H, m), 3.20–3.36(4H, m), 3.96(1H, t), 4.60–4.70(3H, m), 5.27 (1H, d), 5.58(2H, dd), 7.29(2H, d), 7.35(1H, d), 7.39(1H, d), 7.42(1H, s), 7.52–7.55(2H, m), 7.60(2H, d), 7.85(1H, d), 7.88(1H, m), 8.06(1H, m), 8.28 (1H, s)

FAB Mass (M+H): 563

EXAMPLE 82

Synthesis of 2-{1-[3-(4-cyano-benzyl)-3H-imidazol-4-ylmethyl]-3-naphthalen-1-ylmethyl-2,5-dioxo-imidazolidin-4-yl}-N-(2-(N,N-dimethylamino)-ethyl)-acetamide(Compound 82)

0.060 g(Yield 78%, MW 550) of the title compound was prepared using 0.073 g(0.14 mmol) of the compound prepared in Example 78 and 0.016 ml(0.18 mmol) of 2-(N,N-dimethylamino)ethylamine according to the same procedure as Example 80.

¹H NMR(CDCl₃) δ(ppm) 2.34–2.60(2H, m), 2.91(1H, m), 3.05(1H, m), 3.20 (2H, m), 3.27(3H, s), 3.68(1H, t), 4.57

(2H, dd), 4.90(1H, d), 5.03(1H, d), 5.26(1H, s), 5.44(2H, dd), 7.12(2H, d), 7.29(1H, s), 7.36(1H, d), 7.42(1H, t), 7.48–7.53(5H, m), 7.87(2H, m), 8.09(1 H, m)

FAB Mass (M+H): 551

EXAMPLE 83

Synthesis of 2-{1-[3-(4-bromo-benzyl)-3H-imidazol-4-ylmethyl]-3-naphthalen-1-ylmethyl-2,5dioxo-imidazolidin-4-yl}-N-(2-methoxy-ethyl)-N-methyl-acetamide(Compound 83)

83-1) Synthesis of 2-{1-[3-(4-bromo-benzyl)-3H-imidazol-4-ylmethyl]-3-naphthalen-1-ylmethyl-2,5-dioxo-imidazolidin-4-yl}-acetic acid The title compound was prepared using the compounds prepared in Preparations 6 and 3 according to the same procedures as Examples 72 and 78 in 83% yield.

FAB Mass (M+H): 547

83-2) Synthesis of 2-{1-[3-(4-bromo-benzyl)-3H-imidazol-4-ylmethyl]-3-naphthalen-1-ylmethyl-2,5-dioxo-imidazolidin-4-yl}-N-(2-methoxy-ethyl)-N-methyl-acetamide 0.045 g(Yield 73%, MW 617) of the title compound was prepared using 0.055 g(0.10 mmol) of the compound prepared in Example 83-1) and 0.011 g(0.12 mmol) of N-methyl-2-methoxyethylamine according to the same procedure as Example 80.

$^1$H NMR(CDCl$_3$) δ(ppm) 2.36(1.5H, s), 2.44(1H, m), 2.58(1.5H, s), 2.65 (0.5H, dd), 2.80(0.5H, m), 2.89(1H, m), 3.00–3.14(1H, m), 3.16(1H, t), 3.21 (1.5H, s), 3.25(1.5H, m), 3.63(1H, m), 3.84(0.5H, t), 4.65(2H, d), 4.74(1H, dd), 5.09(1H, dd), 5.37(2H, s), 6.98(2H, t), 7.32–7.55(8H, m), 7.77–7.88(2H, m), 8.08(1H, m)

FAB Mass (M+H): 618

EXAMPLE 84

Synthesis of 4-((5S)-{4-[2-(4-methyl-piperazin-1-yl)-2-oxo-ethyl]-3-naphthalen-1-ylmethyl-2,5-dioxo-imidazolidin-1-ylmethyl}-imidazol-1-ylmethyl)-benzonitrile(Compound 84)

The same procedure as Example 78 was carried out using 0.14 g(0.28 mmol) of the compound prepared in Example 79 and the resulting product was reacted with 0.044 ml(0.40 mmol) of N-methyl-piperazine according to the same procedure as Example 80 to obtain 0.11 g of the title compound (Yield 71%, MW 575.7).

$^1$H NMR(CDCl$_3$) δ(ppm) 2.15(2H, br), 2.22(3H, s), 2.39 (2H, m), 2.73(1H, br), 2.84(1H, br), 2.97(1H, br), 3.28(1H, br), 3.87(1H, t), 4.58(2H, d), 4.68 (1H, d), 5.17(1H, d), 5.44(2H, dd), 7.12(2H, d), 7.27(1H, s), 7.11(2H, d), 7.39 (1H, t), 7.48–7.56(5H, m), 7.84(1H, d), 7.87(1H, m), 8.05 (2H, m)

FAB Mass (M+H): 576

EXAMPLE 85

Synthesis of (2S)-(2-{1-[3-(4-cyano-benzyl)-3H-imidazol-4-ylmethyl]-3-naphthalen-1-ylmethyl-2,5-dioxo-imidazolidin-4-yl}-acetamino)-4-methylsulfanyl-butyric acid methyl ester(Compound 85)

0.17 g(Yield 84%, MW 638) of the title compound was prepared using 0.16 g(0.31 mmol) of the compound prepared in Example 78 and 0.066 g(0.35 mmol) of (L)-methionine methyl ester hydrochloride according to the same procedure as Example 80.

$^1$H NMR(CDCl$_3$) δ(ppm) 1.80(1H, br), 1.96(3H, m), 2.05(3H, d), 2.32(1H, m), 2.38(1H, t), 2.52(1H, m), 2.65 (1H, m), 3.73(41H, m), 4.29–4.40(1H, m), 4.55(2H, dd), 4.74(1H, m), 5.24(1H, t), 5.44(2H, m), 6.04(1H, s), 7.11(2H, t), 7.27(1H, d), 7.37(1H, d), 7.42(1H, t), 7.47–7.53(51H, m), 7.87(2H, m), 8.06(1H, m)

FAB Mass (M+H): 639

EXAMPLE 86

Synthesis of (2S)-(2-{1-[3-(4-cyano-benzyl)-3H-imidazol-ylmethyl]-3 -naphthalen-1-ylmethyl-2,5-dioxo-imidazolidin-4-yl}-acetamino)4-methylsulfanyl-butyric acid(Compound 86)

The title compound was prepared using the compound prepared in Example 85 according to the same procedure as Example 78 in 95% yield.

FAB Mass (M+H): 625

EXAMPLE 87

Synthesis of 3-(3-imidazol-1-yl-propyl)-1-naphthalen-1-yl-imidazolidin-2,4-dione(Compound 87)

0.13 g(Yield 91%, MW 334) of the title compound was prepared using 0.10 g(0.44 mmol) of the compound prepared in Preparation 2 and 0.055 g(0.44 mmol) of the compound prepared in Preparation 8 according to the same procedure as Example 72.

$^1$H NMR(CDCl$_3$) δ(ppm) 2.18(2H, m), 3.66(2H, t), 3.99 (2H, t), 4.31(2H, s), 6.95(1H, s), 7.02(1H, s), 7.17(1H, s), 7.42(1H, t), 7.50(2H, m), 7.65 (1H, d), 7.85(1H, d), 7.92(2H, m)

FAB Mass (M+H): 335

As mentioned above, compounds according to the present invention have an inhibitory activity against farnesyl transferase. In order to determine such inhibitory activity of the compounds, following experiments were performed.

Experimental Example 1

Analysis of Ras Farnesyl Transferase Inhibiting Activity

In the present experiment, Ras farnesyl transferase produced by genetic recombination techniques by the improved Pompliano's method(Pompliano et al.; Biochemistry, 1992, 31, 3800) was used, Ras substrate (Ras-CVLS) protein was used by purifying by the known method(Chung et al., Biochemicia et Biophysica Act. 1992, 278, 1129).

The enzyme reaction was performed in 50 μl of 50 mM Sodium HEPES buffer solution containing 25 mmol of potassium chloride. 25 mmol of magnesium chloride, 10 mmol of DTT and 50 μmol of zinc chloride. 1.5 μmol of Ras substrate protein, 0.15 μmol of tritium-farnesylpyrophosphate and 4.5 nmol of farnesyl transferase were used.

More specifically, in the initial step, farnesyl transferase was added to the above buffer solution, reaction was maintained for 30 minutes at 37° C. and then the reaction was stopped by adding 1 ml of ethanol solution containing 1M HCl. The formed precipitates were adsorbed to GF/B filter using Hopper harvestor(Hopper #225V) for filter-binding, washed with ethanol, and then radioactivity of the dried filter was measured using LKB β counter. Enzyme titer was measured in the unsaturated state of substrate where the concentrations of Ras substrate protein and farnesyl transferase have quantitative relationship. Enzyme inhibiting activity was measured using less than 5% of total reaction solution of the compound according to the present invention dissolved in dimethylsulfoxide(DMSO) solution as a reagent. Enzyme inhibiting activity was represented by percentage of the amount of the farnesyl incorporated with the reagent to that without the reagent. $IC_{50}$ of the reagent was defined as the concentration inhibiting the enzyme activity by 50%.

To evaluate the selective enzyme inhibiting activity of the compound according to the present invention, inhibiting activity on geranylgeranyl transferase was measured. Geranylgeranyl transferase was purified from bovine brain with the method modified from Schber's method(Schber et al., J. Biol. Chem. 1990, 265, 14701). and substantially the same experiment as that of farnesyl transferase was performed using geranylgeranyl pyrophosphate and Ras-CVIL substrate protein under the similar condition to farnesyl transferase reaction.

Experimental Example 2

Analysis of Intracellular Ras Farnesyl Transferase Inhibiting Activity

In the present experiment, Rat2 cell line which expresses C-Harvey-Ras protein having transforming activity and Rat2 cell line(Korean patent application No. 97-14409) which is transformed with fused protein of H-Ras substituted with polybasic lysine domain at C-terminus of K-Ras were used. The experiment was performed by the modified Declue's method(Declue. J. E. et al., Cancer Research, 1991. 51, 712). Hereinafter, the experimental method will be described in more detail.

$3 \times 10^5$ cells of transformed Rat2 fibroblast cell line were sprayed on 60 mm cell cultivation dish and cultivated for 48 hours in a cell incubator at 37° C. and after 50% or more of density was reached, it was treated with a reagent. The compound according to the present invention dissolved in dimethylsulfoxide(DMSO) was used as the reagent. 1% of dimethylsulfoxide was used in both control and experimental groups. After 4 hours from the treatment of the reagent, methionine labeled with 150 μCi of radioactive isotope, $^{35}$S per 1 ml of medium, was added and after cultivating for 20 hours, the cells were washed with physiological saline water. The cells were lysed using 1 ml of cool cell lysis buffer solution(50 mM of Sodium Herpiss buffer solution containing 5 mmol of magnesium chloride. 1 mmol of DTT, 1% NP 40, 1 mmol of EDTA, 1 mmol of PMSF, 2 μmol of leupeptin, 2 μmol of pepstatin A and 2 μmol of antipain) and the supernatant was obtained by high-velocity centrifugation of 12,000 g×5 minutes. The amount of the labeled radioisotope of the supernatent was measured and standardized to obtain a quantitative result in immunoprecipitation reaction and then. Y13-259, monoclonal antiboby specifically binding to Ras protein(Furth, M. E. et al., J. Virol, 1982, 43, 294) was added and reacted for 15 hours at 4° C. Protein A bound to goat anti-murine Immunoglobulin antibody-agarose suspension was added to the solution and reacted for 1 hour at 4° C. and then, to remove unspecific binding product, immunoprecipitates were washed with buffer solution(50 mM Tris chloride buffer solution containing 50 mmol of sodium chloride, 0.5% of sodium dioxycolate, 0.5% of NP 40 and 0.1% of SDS). The precipitates were boiled in reagent buffer solution for electrophoresis and then, electrophoresis was performed using 13.5% of SDS polyacrylamide gel. After electrophoresis, the gel was fixed and dried. Then, the gel was exposed to X-ray film, developed and printed. From the result of the experiment, intensities of band of protein with and without farnesyl of Ras protein were measured, and the concentration of reagent inhibiting 50% of farnesyl binding was defined as $CIC_{50}$, an intracellular Ras farnesyl transferase inhibiting activity.

For the compound according to the present invention, from the results of the experiment according to the above Experimental Examples 1 and 2, $IC_{50}$ was 50 μM or less and $CIC_{50}$ was 100 μM or less. The results are shown in the below table 2a to 2d.

TABLE 2a

| Compound No. | Ftase | | GGtase |
|---|---|---|---|
| | $IC_{50}$ (nM) | $CIC_{50}$ (μM) | $IC_{50}$ (μM) |
| 1 | 500 | 1 | >10 |
| 2 | 0.8 | 5 | 3.4 |
| 3 | 2500 | 5 | >10 |
| 4 | 4.8 | 10 | 0.7 |
| 5 | 190000 | 10 | >10 |
| 6 | 61 | 7.3 | >10 |
| 7 | 180 | <20 | >10 |
| 8 | 14 | <20 | >10 |
| 9 | 15 | <1 | 80 |
| 10 | >50000 | <20 | >10 |
| 11 | >50000 | <20 | >10 |
| 12 | 5500 | <20 | >10 |
| 13 | 1.5 | <20 | >10 |
| 14 | 1 | <20 | >10 |
| 15 | 2 | <20 | >10 |
| 16 | 2500 | <20 | >10 |
| 17 | 1500 | <20 | >10 |
| 18 | 600 | <20 | >10 |
| 19 | 240 | <20 | >10 |
| 20 | 300 | <20 | >10 |
| 21 | 150 | <20 | >10 |
| 22 | 1700 | <20 | >10 |
| 23 | 3000 | <20 | >10 |

TABLE 2b

| Compound No. | Ftase | | GGtase |
|---|---|---|---|
| | $IC_{50}$ (nM) | $CIC_{50}$ (μM) | $IC_{50}$ (μM) |
| 24 | 750 | <20 | >10 |
| 25 | 720 | <20 | >10 |
| 26 | 700 | <20 | >10 |
| 27 | 210 | <20 | >10 |
| 28 | 1100 | <20 | >10 |
| 29 | 80 | <20 | >10 |
| 30 | 725 | <20 | >10 |
| 31 | 900 | <20 | >10 |
| 32 | 92 | <20 | >10 |
| 33 | 1300 | <20 | >10 |
| 34 | 2100 | <20 | >10 |
| 35 | 500 | <20 | >10 |
| 36 | 1200 | <20 | >10 |
| 37 | 350 | <20 | >10 |
| 38 | 250 | <20 | >10 |
| 39 | 200 | <20 | >10 |
| 40 | 1400 | <20 | >10 |
| 41 | 530 | <20 | >10 |
| 42 | 1000 | <20 | >10 |
| 43 | 5000 | <20 | >10 |
| 44 | 8000 | <20 | >10 |

TABLE 2b-continued

| | Ftase | | GGtase |
|---|---|---|---|
| Compound No. | IC$_{50}$ (nM) | CIC$_{50}$ ($\mu$M) | IC$_{50}$ ($\mu$M) |
| 45 | 5500 | <20 | >10 |
| 46 | 44 | <20 | >10 |

TABLE 2c

| | Ftase | | GGtase |
|---|---|---|---|
| Compound No. | IC$_{50}$ (nM) | CIC$_{50}$ ($\mu$M) | IC$_{50}$ ($\mu$M) |
| 47 | 18 | <20 | >10 |
| 48 | 40 | <20 | >10 |
| 49 | 55 | <20 | >10 |
| 50 | 55 | <20 | >10 |
| 51 | 19 | <20 | >10 |
| 52 | 19 | <20 | >10 |
| 53 | 65 | <20 | >10 |
| 54 | 50 | <20 | >10 |
| 55 | 45 | <20 | >10 |
| 56 | 80 | <20 | >10 |
| 57 | 16 | 400 | >10 |
| 58 | 14 | <20 | >10 |
| 59 | 440 | <20 | >10 |
| 60 | 160 | <20 | >10 |
| 61 | 160 | <20 | >10 |
| 62 | 50 | <20 | >10 |
| 63 | 50 | <20 | >10 |
| 64 | 700 | <20 | >10 |
| 65 | 4500 | <20 | >10 |
| 66 | 200 | <20 | >10 |
| 67 | 3600 | <20 | >10 |
| 68 | 5000 | <20 | >10 |
| 69 | 300 | <20 | >10 |

TABLE 2d

| | Ftase | | GGtase |
|---|---|---|---|
| Compound No. | IC$_{50}$ (nM) | CIC$_{50}$ ($\mu$M) | IC$_{50}$ ($\mu$M) |
| 70 | 5000 | <20 | >10 |
| 71 | 7000 | <20 | >10 |
| 72 | 20 | <20 | >10 |
| 73 | 800 | <10 | >10 |
| 74 | 4000 | <50 | >10 |
| 75 | 30 | >50 | >10 |
| 76 | 5000 | >50 | >10 |
| 77 | 50 | <10 | >10 |
| 78 | 100 | <20 | >10 |
| 79 | 40 | <10 | >10 |
| 80 | 90 | <10 | >10 |
| 81 | 110 | <20 | >10 |
| 82 | 150 | <20 | >10 |
| 83 | 1500 | >50 | >10 |
| 84 | 120 | <20 | >10 |
| 85 | 200 | <50 | >10 |
| 86 | 50 | <10 | >10 |
| 87 | 5000 | >50 | >10 |

As can be seen from the above results((IC$_{50}$≦50 $\mu$M, CIC$_{50}$≧100 $\mu$M), the novel hydantoin derivative according to the present invention effectively inhibits the activity of farnesyl transferase in trasfering farnesyl group of Ras protein. Thus, the compound of formula (I) can be advantageously used as an anti-cancer agent.

What is claimed is:
1. A hydantoin compound represented by the following formula (I):

[Formula I]

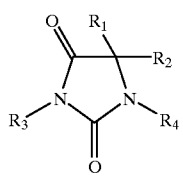

or pharmaceutically acceptable salt thereof in which
R$_1$ and R$_2$ independently of one another represent hydrogen; lower alkyl; monocyclic or bicyclic aryl group which is unsubstituted or substituted by lower alkyl or halogen; heterocyclic group containing hetero atoms selected from a group consisting of nitrogen and sulfur as ring member; or a radical having the following formula:

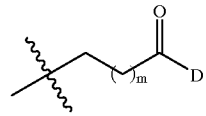

(wherein D represents alkoxy; hydroxy; amino acid residue; morpholine; thiomorpholine; piperazine, alkoxyalkylamine or aryloxyalkylamine each of which is substituted or unsubstituted by lower alkyl, and m is selected from 0 to 2),
R$_3$ represents amino acid residue; or a radical having the following formula,

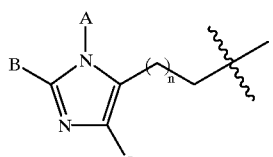

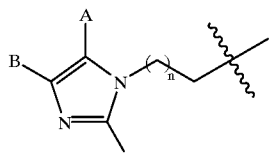

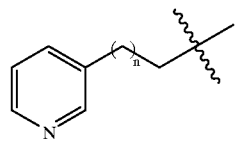 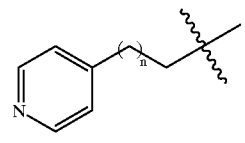

wherein
A represents hydrogen; lower alkyl; aryl group which is substituted by substituents selected from a group consisting of halogen, cyano(CN), nitro(NO$_2$), carboxy (COOH), amide, thioamide, SR and lower alkyl; heterocyclic group containing hetero atoms selected from a group consisting of nitrogen and sulfur as ring member, which is substituted by substituents selected from a group consisting of halogen, cyano, nitro, COOR, amide, thioamide, SR and lower alkyl; lower alkyl substituted by the substituted aryl or heterocyclic group as mentioned above; or a radical having the following formula:

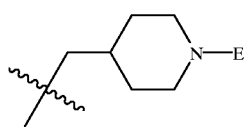
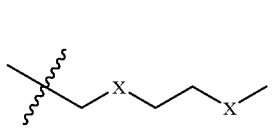 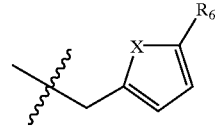

(in the definition for the substituent A, R represents hydrogen or lower alkyl, and E represents hydrogen or —F—G wherein F represents $CH_2$, C=O, $SO_2$, and G represents hydrogen; lower alkyl substituted or unsubstituted by phenyl or biphenyl; lower alkoxy; phenyl; benzyl; benzyloxy; amine substituted or unsubstituted by lower alkyl, phenyl, benzyl, cycloalkyl or phenoxy alkyl), B and C independently of one another represent hydrogen, halogen or lower alkyl, n denotes an integer of 0 to 4, $R_4$ represents hydrogen; aromatic group substituted or unsubstituted by lower alkyl or halogen; bicyclic aromatic group; heteroaromatic group containing hetero atoms selected from a group consisting of nitrogen and sulfur as ring member; or a radical having the following formula:

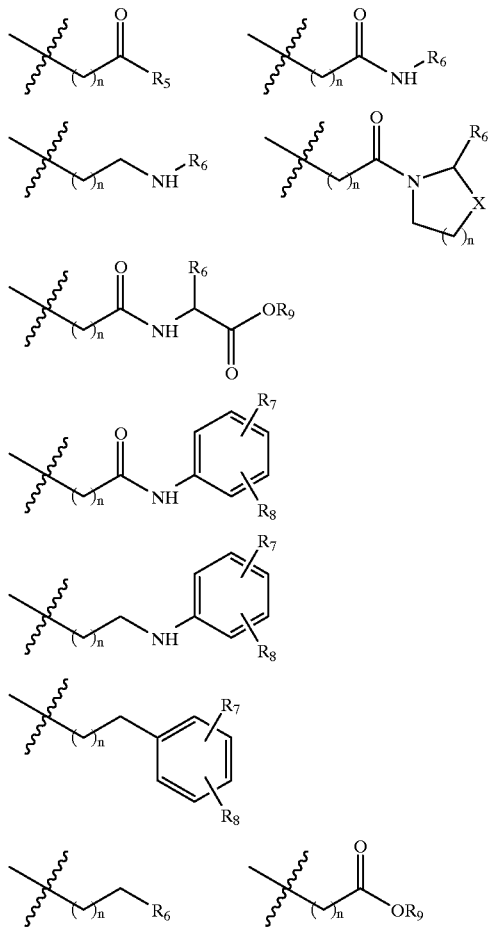

wherein $R_5$ represents aryl group substituted by lower alkoxy; or heterocyclic group containing hetero atoms selected from a group consisting of nitrogen, oxygen and sulfur as ring member, $R_6$ represents hydrogen; lower alkyl; lower alkyl which is substituted by substituents selected from a group consisting of halogen, cyano, hydroxy, COOR, amide, thioamide, SR and $SO_2R$; lower alkyl substituted by an aryl group which is substituted by substituents selected from a group consisting of halogen, cyano, COOR, amide, thioamide, SR, $SO_2R$ and lower alkyl; heterocyclic group containing hetero atoms selected from a group consisting of nitrogen and sulfur as ring member; heterocyclic group which is substituted by substituents selected from a group consisting of halogen, cyano, COOR, amide, thioamide, SR, $SO_2R$ and lower alkyl and which contains hetero atoms selected from a group consisting of nitrogen and sulfur as ring member, wherein R represents lower alkyl, $R_7$ and $R_8$ independently of one another represent hydrogen, halogen, halogenoalkyl, cyano, amide, thioamide, alkoxy or phenoxy, or represent a radical having the following formula,

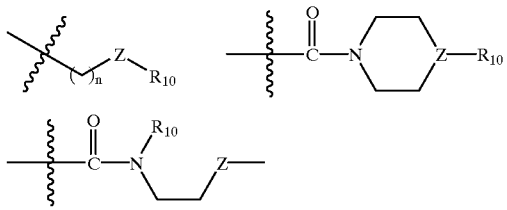

wherein

Z represents $CH_2$, CO, O, S, $SO_2$, $NR_9$, $NHSO_2$ or NHCOO, $R_{10}$ represents hydrogen, lower alkyl, halogenoalkyl, alkoxy, hydroxy, benzyloxycarbonyl or benzyl, $R_9$ represents hydrogen or lower alkyl or lower alkyl substituted by aromatic group, X represents $CH_2$, CO, O, S or $SO_2$, and n denotes an integer of 0 to 4.

2. The compound of claim 1 wherein $R_1$ represents hydrogen; monocyclic or bicyclic aryl group which is unsubstituted or substituted by lower alkyl or halogen; or a radical having the following formula:

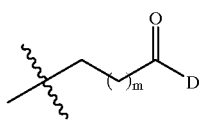

(wherein D represents alkoxy; hydroxy; amino acid residue; morpholine; thiomorpholine; piperazine or alkoxyalkylamine each of which is substituted or unsubstituted by lower alkyl, and m is selected from 0 to 1), R₂ represents hydrogen; lower alkyl; or a radical having the following formula:

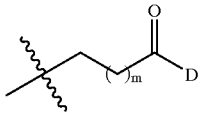

(wherein D represents alkoxy; hydroxy; amino acid residue; morpholine; thiomorpholine; piperazine or alkoxyalkylamine each of which is substituted or unsubstituted by lower alkyl, and m is selected from 0 to 1), R₃ represents a radical having the following formula,

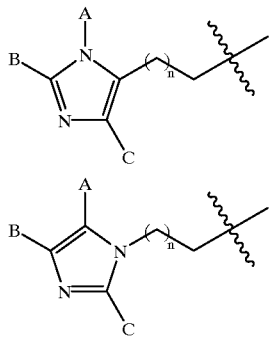

wherein

A represents hydrogen; aryl group which is substituted by substituents selected from a group consisting of halogen, cyano(CN), nitro(NO₂), carboxy(COOH), amide, thioamide, SR and lower alkyl; or a radical having the following formula:

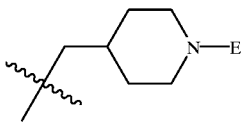

(in the definition for the substituent A, R represents hydrogen or lower alkyl, and E represents hydrogen or —F—G wherein F represents C=O, and G represents benzyloxy, lower alkoxy, or lower alkyl substituted or unsubstituted by phenyl), B and C independently of one another represent hydrogen, n denotes an integer of 1 to 3, R₄ represents hydrogen; aromatic group substituted or unsubstituted by halogen; bicyclic aromatic group; heteroaromatic group containing hetero atoms selected from a group consisting of nitrogen and sulfur as ring member; or a radical having the following formula:

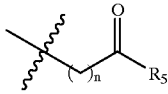 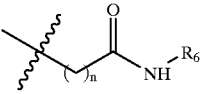

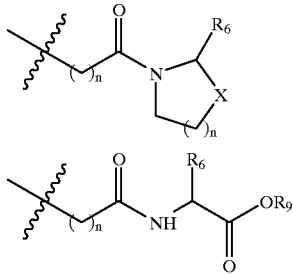

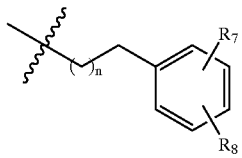

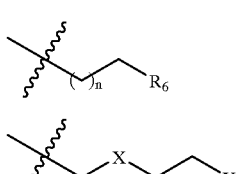

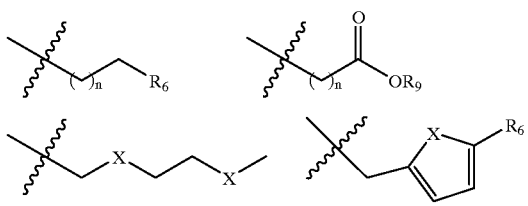

wherein

R₅ represents aryl group substituted by lower alkoxy; or heterocyclic group containing hetero atoms selected from a group consisting of nitrogen, oxygen and sulfur as ring member, R₆ represents hydrogen; lower alkyl; lower alkyl which is substituted by substituents selected from a group consisting of halogen, cyano, hydroxy, COOR, amide, thioamide, SR and SO₂R; lower alkyl substituted by an aryl group which is substituted by substituents selected from a group consisting of halogen, cyano, COOR, amide, thioamide, SR, SO₂R and lower alkyl; or heterocyclic group containing hetero atoms selected from a group consisting of nitrogen and sulfur as ring member; heterocyclic group which is substituted by substituents selected from a group consisting of halogen, cyano, COOR, amide, thioamide, SR, SO₂R and lower alkyl and which contains hetero atoms selected from a group consisting of nitrogen and sulfur as ring member, wherein R represents lower alkyl, R₇ and R₈ independently of one another represent hydrogen, halogen, halogenoalkyl, cyano or phenoxy, or represent a radical having the following formula,

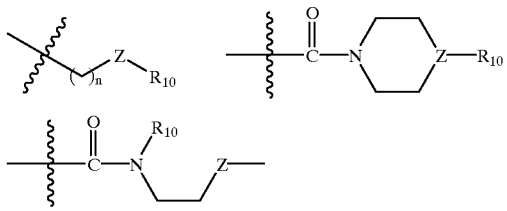

wherein

Z represents O, S, SO₂, NR₉, NHSO₂ or NHCOO,

R₁₀ represents hydrogen, lower alkyl, halogenoalkyl, alkoxy, hydroxy or benzyloxycarbonyl, R₉ represents hydrogen or lower alkyl, X represents O, S or SO₂, and n denotes an integer of 1 to 3.

3. The compound of claim 2 which is selected from a group consisting of:

2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid methyl ester, 2-(2-{3-[3-(1H-imidazol-4-yl)-propyl]-5-methyl-5-naphthalen-1-yl-2,4-dioxo-imidazolidin-1-yl}-acetylamino)-4-methylsulfanyl-butyric acid, 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid methyl ester, 2-(2-{3-[2-(1H-imidazol-4-yl)-ethyl]-5-methyl-5-naphthalen-1-yl-2,4-dioxo-imidazolidin-1-yl}-acetylamino)-4-methylsulfanyl-butyric acid, 2-{2-[3-(3H-imidazol-4-yl-methyl)-5-methyl-5-naphthalen-1-yl-2,4-dioxo-imidazolidin-1-yl]-acetylamino}-4-methylsulfanyl-butyric acid methyl ester, 2-{2-[3-(3H-imidazol-4-yl-methyl)-5-methyl-5-naphthalen-1-yl-2,4-dioxo-imidazolidin-1-yl]-acetylamino}-4-methylsulfanyl-butyric acid, 2-(2-{3-[3-(4-cyano-benzyl)-imidazol-4-yl-methyl]-5-methyl-5-naphthalen-1-yl-2,4-dioxo-imidazolidin-1-yl}-acetylamino)-4-methylsulfanyl-butyric acid methyl ester, 2-(2-{3-[3-(4-cyano-benzyl)-imidazol-4-yl-methyl]-5-methyl-5-naphthalen-1-yl-2,4-dioxo-imidazolidin-1-yl}-acetylamino)-4-methylsulfanyl-butyric acid, 2-(2-{3-[3-(3H-imidazol-4-yl)-propyl]-5-methyl-5-naphthalen-1-yl-2,4 -dioxo-imidazolidin-1-yl}-acetylamino)-3-thiophen-2-yl-propionic acid, 3-[3-(3H-imidazol-4-yl)-propyl]-5-methyl-5-naphthalen-1-yl-1-(2-oxo-2-thiazolidin-3-yl-ethyl)-imidazolidin-2,4-dione, 1-[2-(1,1-dioxo-thiazolidin-3-yl)-3-(3H-imidazol-4-yl)-propyl]-5-methyl-5-naphthalen-1-yl-imidazolidin-2,4-dione, 3-[3-(3H-imidazol-4-yl)-propyl]-5-methyl-1-{2-[2-(2-methylsulfanyl-ethyl)-thiazolidin-3-yl]-2-oxo-ethyl}-5-naphthalen-1-yl-imidazolidin-2,4-dione, 2-(2-{3-[3-(3H-imidazol-4-yl)-propyl]-5-methyl-5-naphthalen-1-yl-2,4-dioxo-imidazolidin-1-yl}-acetylamino)-4-methylsulfonyl-butyric acid, 2-{2-[3-(3-imidazol-1-yl-propyl)-5-methyl-5-naphthalen-1-yl-2,4-dioxo-imidazolidin-1-yl]-acetylamino}-4-methylsulfanyl-butyric acid, 2-{2-[3-(2-imidazol-1-yl-ethyl)-5-methyl-5-naphthalen-1-yl-2,4-dioxo-imidazolidin-1-yl]-acetylamino}-4-methylsulfanyl-butyric acid, 1-benzyl-3-(3-imidazol-1-yl-propyl)-5-methyl-5-naphthalen-1-yl-imidazolidin-2,4-dione, 1-(pentafluoro-benzyl)-3-(3-imidazol-1-yl-propyl)-5-methyl-5-naphthalen-1-yl-imidazolidin-2,4-dione, 1-(3-pyridylmethyl)-3-(3-imidazol-1-yl-propyl)-5-methyl-5-naphthalen-1-yl-imidazolidin-2,4-dione, 1-(3-chloro-benzyl)-3-(3-imidazol-1-yl-propyl)-5-methyl-5-naphthalen-1-yl-imidazolidin-2,4-dione, 1-(3-bromo-benzyl)-3-(3-imidazol-1-yl-propyl)-5-methyl-5-naphthalen-1-yl-imidazolidin-2,4-dione, 1-(4-bromo-benzyl)-3-(3-imidazol-1-yl-propyl)-5-methyl-5-naphthalen-1-yl-imidazolidin-2,4-dione, 1-(3-trifluoromethyl-benzyl)-3-(3-imidazol-1-yl-propyl)-5-methyl-5-naphthalen-1-yl-imidazolidin-2,4-dione, 1-(3-trifluoromethoxy-benzyl)-3-(3-imidazol-1-yl-propyl)-5-methyl-5-naphthalen-1-yl-imidazolidin-2,4-dione, 3-(3-imidazol-1-yl-propyl)-5-methyl-5-naphthalen-1-yl-1-(4 -phenoxy-benzyl)-imidazolidin-2,4-dione, 3-(3-imidazol-1-yl-propyl)-5-methyl-5-naphthalen-1-yl-1-(3-phenoxy-benzyl)-imidazolidin-2,4-dione, 3-(3-imidazol-1-yl-propyl)-1-(4-methylsulfanyl-benzyl)-5-methyl-5-naphthalen -1-yl-imidazolidin-2,4-dione, 3-(3-imidazol-1-yl-propyl)-5-methyl-1-(4-methylsulfanylmethyl-benzyl)-5-naphthalen-1-yl-imidazolidin-2,4-dione, 3-(3-imidazol-1-yl-propyl)-5-methyl-1-(4-methylsulfonyl-benzyl)-5-naphthalen-1-yl-imidazolidin-2,4-dione, 5-[3-(3-imidazol-1-yl-propyl)-5-methyl-5-naphthalen-1-yl-2,4-dioxo-imidazolidin-1-ylmethyl]-2-methylsulfanyl-benzonitrile, 5-[3-(3-imidazol-1-yl-propyl)-5-methyl-5-naphthalen-1-yl-2,4-dioxo-imidazolidin-1-ylmethyl]-2-methylsulfonyl-benzonitrile, 2-[3-(3-imidazol-1-yl-propyl)-5-methyl-5-naphthalen-1-yl-2,4-dioxo-imidazolidin-1-ylmethyl]-benzonitrile, 3-[3-(3-imidazol-1-yl-propyl)-5-methyl-5-naphthalen-1-yl-2,4-dioxo-imidazolidin-1-ylmethyl]-benzonitrile, 4-[3-(3-imidazol-1-yl-propyl)-5-methyl-5-naphthalen-1-yl-2,4-dioxo-imidazolidin-1-ylmethyl]-benzonitrile, 1-(4-aminomethyl-benzyl)-3-(3-imidazol-1-yl-propyl)-5-methyl-5-naphthalen-1-yl-imidazolidin-2,4-dione, N-{2-[3-(3-imidazol-1-yl-propyl)-5-methyl-5-naphthalen-1-yl-2,4-dioxo-imidazolidin-1-ylmethyl]-benzyl}-methanesulfonamide, N-{3-[3-(3-imidazol-1-yl-propyl)-5-methyl-5-naphthalen-1-yl-2,4-dioxo-imidazolidin-1-ylmethyl]-benzyl}-methanesulfonamide, N-{4-[3-(3-imidazol-1-yl-propyl)-5-methyl-5-naphthalen-1-yl-2,4-dioxo-imidazolidin-1-ylmethyl]-benzyl}-methanesulfonamide, 4-[3-(3-imidazol-1-yl-propyl)-5-methyl-5-naphthalen-1-yl-2,4-dioxo-imidazolidin-1-ylmethyl]-benzoic acid methyl ester, 4-[3-(3-imidazol-1-yl-propyl)-5-methyl-5-naphthalen-1-yl-2,4 -dioxo-imidazolidin-1-ylmethyl]-benzoic acid, 3-(3-imidazol-1-yl-propyl)-1-[3-(morpholine-4-carbonyl)-benzyl]-5-methyl-5-naphthalen-1-yl-imidazolidin-2,4-dione, 4-[3-(3-imidazol-1-yl-propyl)-5-methyl-5-naphthalen-1-yl-2,4-dioxo-imidazolidin-1-ylmethyl]-N-(2-methoxy-ethyl)-benzamide, 4-[3-(3-imidazol-1-yl-propyl)-5-methyl-5-naphthalen-1-yl-2,4-dioxo-imidazolidin-1-ylmethyl]-N-(2-methoxy-ethyl)-N-methyl-benzamide, 4-{4-[3-(3-imidazol-1-yl-propyl)-5-methyl-5-naphthalen-1-yl-2,4-dioxo-imidazolidin-1-ylmethyl]-benzoyl}-piperazine-1-carboxylic acid benzyl ester, 3-(3-imidazol-1-yl-propyl)-1-[3-(thiomorpholine-4-carbonyl)-benzyl]-5-methyl-5-naphthalen-1-yl-imidazolidin-2,4-dione, 4-{5-[3-(4-methyl-4-naphthalen-1-yl-2,5-dioxo-imidazolidin-1-yl)-propyl]-imidazol-1-ylmethyl}benzonitrile, 4-{5-[3-(3-methyl-4-methyl-4-naphthalen-1-yl-2,5-dioxo-imidazolidin-1-yl)-propyl]-imidazol-1-ylmethyl}-benzonitrile, 4-{5-[3-(3-ethyl-4-methyl-4-naphthalen-1-yl-2,5-dioxo-imidazolidin-1-yl)-propyl]-imidazol-1-ylmethyl}-benzonitrile, 4-{5-[3-(3-propyl-4-methyl-4-naphthalen-1-yl-2,5-dioxo-imidazolidin-1-propyl]-imidazol-1-ylmethyl}benzonitrile, 4-{5-[3-(3-butyl-4-methyl-4-naphthalen-1-yl-2,5-dioxo-imidazolidin-1-yl)-propyl]-imidazol-1-ylmethyl}benzonitrile, 4-(5-{3-[3-(2-methoxy-ethoxymethyl)-4-methyl-4-naphthalen-1-yl-2,5-dioxo-imidazolidin-1-yl]-propyl}-imidazol-1-ylmethyl)-benzonitrile, (3-{3-[3-(4-cyanobenzyl)-3H-imidazol-4-yl]-propyl}-5-methyl-5-naphthalen-1-yl-2,4-dioxo-imidazolidin-1-yl)-acetic acid ethyl ester, (3-{3-[3-(4-cyanobenzyl)-3H-imidazol-4-yl]-propyl}-5-methyl-5-naphthalen-1-yl-2,4-dioxo-imidazolidin-1-yl)-acetic acid, 4-(5-{3-[3-benzyl-4-methyl-4-naphthalen-1-yl-2,5-dioxo-imidazolidin-1-yl]-propyl}-imidazol-1-ylmethyl)-benzonitrile, 4-(5-{3-[3-(3-cyano-benzyl)-4-methyl-4-naphthalen-1-yl-2,5-dioxo-imidazolidin-1-yl]-propyl}-imidazol-1-ylmethyl)-benzonitrile, 4-{5-[3-(3-furan-2-ylmethyl-4-methyl-4-naphthalen-1-yl-2,5-dioxo-imidazolidin-1-yl)-propyl]-imidazol-1-ylmethyl}-benzonitrile, 4-(5-{3-[3-(furan-2-carbonyl)-4-methyl-4-naphthalen-1-yl-2,5-dioxo-imidazolidin-1-yl]-propyl}-imidazol-1-ylmethyl)-benzonitrile, 2-[2-(3-){3-[3-(4-cyano-benzyl)-3H-imidazol-4-yl]-propyl}-5-methyl-5-naphthalen-1-yl-2,4-dioxo-imidazolidin-1-yl)-acetylamino]-4-methylsulfanyl-butyric acid methyl ester, 2-[2-(3-{3-[3-(4-cyano-benzyl)-3H-imidazol-4-yl]-propyl}-5-methyl-5-naphthalen-1-yl-2,4-dioxo-imidazolidin-1yl)-acetylamino]-4-methylsulfanyl-butyric acid, 4-[5-(4-methyl-4-naphthalen-1-yl-2,5-dioxo-imidazolidin-1-ylmethyl)-imidazol-1-ylmethyl]-benzonitrile, 4-[5-(3-methyl-4-methyl-4-naphthalen-1-yl-2,5-dioxo-imidazolidin-1-ylmethyl)-imidazol-1-ylmethyl]-benzonitrile, 4-[5-(3-ethyl-4-methyl-4-naphthalen-1-yl-2,5-dioxo-imidazolidin-1-ylmethyl)-imidazol-1-ylmethyl]-benzonitrile, {3-[3-(4-cyano-benzyl)-3H-imidazol-4-ylmethyl]-5-methyl-5-naphthalen-1-yl-2,4-dioxo-imidazolidin-1-yl)-acetic acid ethyl ester, 4-{5-[3-(3-cyanobenzyl)-4-methyl-4-naphthalen-1-yl-2,5-dioxo-imidazolidin-1-ylmethyl]-imidazol-1-ylmethyl}-benzonitrile, 3-(3-imidazol-1-yl-propyl)-1-(4-methoxy-benzoyl)-5-methyl-5-naphthalen-1-yl-imidazolidin-2,4-dione, 3-(3-imidazol-1-yl-propyl)-5-methyl-1-(morpholine-4-carbonyl)-5-naphthalen-1-yl-imidazolidin-2,4-dione, 3-(3-imidazol-1-yl-propyl)-5-methyl-5-naphthalen-1-yl-2,4-dioxo-imidazolidine-1-carboxylic acid (3-cyanophenyl)-amide, N-(4-cyano-tetrahydropyran-4-yl)-2-[3-(3-imidazol-1-yl-propyl)-5-methyl-5-naphthalen-1-yl-2,4-dioxo-imidazolidin-1-yl]-acetamide, 3-{3-[3-(4-bromo-benzyl)-3H-imidazol-4-yl]-propyl}-5-methyl-5-naphthalen-1-yl-imidazolidin-2,4-dione, 3-{3-[3-(4-bromo-benzyl)-3H-imidazol-4-yl]-propyl}-1,5-dimethyl-5-naphthalen-1-yl-imidazolidin-2,4-dione, (3-{3-[3-(4-bromo-benzyl)-3H-imidazol-4-yl]-propyl}-5-methyl-5-naphthalen-1-yl-2,4-dioxo-imidazolidin-1-yl)-acetic acid ethyl ester, 3-[3-(3-imidazol-1-yl-propyl)-5-methyl-5-phenyl-2,4-dioxo-imidazolidin-1-ylmethyl]-benzonitrile, 4-[5-(3-naphthalen-1-yl-2,5-dioxo-imidazolidin-1-ylmethyl)-imidazol-1-ylmethyl]-benzonitrile, 3-[3-(4-chloro-benzyl)-3H-imidazol-4-ylmethyl]-1-naphthalen-1-yl-imidazolidin-2,4-dione, 4-[5-(3-naphthalen-1-yl-2,5-dioxo-imidazolidin-1-ylmethyl)-imidazol-1-ylmethyl]-piperidine-1-carboxylic acid benzyl ester, 4-[5-(3-naphthalen-1-ylmethyl-2,5-dioxo-imidazolidin-1-ylmethyl)-imidazol-1-ylmethyl]-benzonitrile, 4-[5-(3-naphthalen-1-ylmethyl-2,5-dioxo-imidazolidin-1-ylmethyl)-imidazol-1-ylmethyl]-piperidine-1-carboxylic acid benzyl ester, {1-[3-(4-cyano-benzyl)-3H-imidazol-4-ylmethyl]-3-naphthalen-1-ylmethyl-2,5-dioxo-imidazolidin-4-yl}-acetic acid ethyl ester, {1-[3-(4-cyano-benzyl)-3H-imidazol-4-ylmethyl]-3-naphthalen-1-ylmethyl-2,5-dioxo-imidazolidin-4-yl}-acetic acid, {1-[3-(4-cyano-benzyl)-3H-imidazol-4-ylmethyl]-3-naphthalen-1-ylmethyl-2,5-dioxo-imidazolidin-(4S)-yl}-acetic acid methyl ester, 4-{5-[4-(2-morpholin-4-yl-2-oxo-ethyl)-3-naphthalen-1-ylmethyl-2,5-dioxo-imidazolidin-1-ylmethyl]-imidazol-1-ylmethyl}-benzonitrile, 4-{(5S)-[4-(2-morpholin-4-yl-2-oxo-ethyl)-3-naphthalen-1-ylmethyl-2,5-dioxo-imidazolidin-1-ylmethyl]-imidazol-1-ylmethyl}-benzonitrile, 2-{1-[3-(4-cyano-benzyl)-3H-imidazol-4-ylmethyl]-3-naphthalen-1-ylmethyl-2,5-dioxo-imidazolidin-4-yl}-N-(2-(N,N-dimethylamino)-ethyl)-acetamide, 2-{1-[3-(4-bromo-benzyl)-3H-imidazol-4-ylmethyl]-3-naphthalen-1-ylmethyl-2,5-dioxo-imidazolidin-4-yl}-N-(2-methoxy-ethyl)-N-methyl-acetamide, 4-(5S)-{4-[2-(4-methyl-piperazin-1-yl)-2-oxo-ethyl]-3-naphthalen-1-ylmethyl-2,5-dioxo-imidazolidin-1-ylmethyl}-imidazol-1-ylmethyl)-benzonitrile, (2S)-(2-{-[3-(4-cyano-benzyl)-3H-imidazol-4-ylmethyl]-3-naphthalen-1-ylmethyl-2,5-dioxo-imidazolidin-4-yl}-acetylamino)-4-methylsulfanyl-butyric acid methyl ester, (2S)-(2-{1-[3-(4-cyano-benzyl)-3H-imidazol-4-ylmethyl]-3-naphthalen-1-ylmethyl-2,5-dioxo-imidazolidin-4-yl}-acetylamino)-4-methylsulfanyl-butyric acid, and 3-(3-imidazol-1-yl-propyl)-1-naphthalen-1-yl-imidazolidin-2,4-dione.

4. A process for preparing a hydantoin compound of formula (I) as defined in claim 1 characterized in that 1) a compound represented by the following formula (II):

[Formula II]

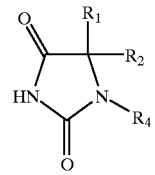

wherein $R_1$, $R_2$ and $R_4$ are defined as in claim 1, is reacted under Mitsunobu reaction condition with a compound represented by the following formula (III):

$R_3$—OH      [Formula III]

wherein $R_3$ is defined as in claim 1, or 2) a compound represented by the following formula (IIa):

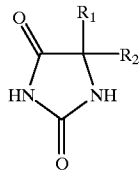

[Formula IIa]

wherein $R_1$ and $R_2$ are defined as previously described, is reacted with the compound of formula (III) under Mitsunobu reaction condition to produce a compound represented by the following formula (Ia):

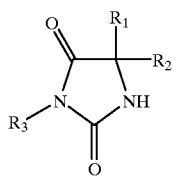

[Formula Ia]

wherein $R_1$, $R_2$ and $R_3$ are defined as previously described, and then $R_4'$—X is reacted with the resulting compound of formula (Ia) to produce a compound represented by the following formula (Ib):

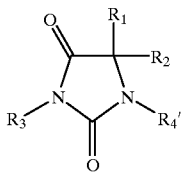

[Formula Ib]

wherein $R_1$, $R_2$ and $R_3$ are defined as previously described and $R_4'$ is the same as $R_4$ except that $R_4'$ is not hydrogen.

5. A composition for inhibiting farnesyl transferase comprising the compound of formula (I) as defined in claim 1 or a pharmaceutically acceptable salt thereof as an active ingredient together with a pharmaceutically acceptable carrier.

\* \* \* \* \*